(12) United States Patent
Hazlebeck et al.

(10) Patent No.: US 11,680,242 B2
(45) Date of Patent: *Jun. 20, 2023

(54) BIOLOGICAL AND ALGAE HARVESTING AND CULTIVATION SYSTEMS AND METHODS

(71) Applicant: Global Algae Technology, LLC, Santee, CA (US)

(72) Inventors: David A. Hazlebeck, El Cajon, CA (US); William Rickman, Lebanon, TN (US)

(73) Assignee: Global Algae Technology, LLC, Santee, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/853,549

(22) Filed: Apr. 20, 2020

(65) Prior Publication Data

US 2020/0248134 A1    Aug. 6, 2020

Related U.S. Application Data

(62) Division of application No. 15/273,552, filed on Sep. 22, 2016, now abandoned.

(Continued)

(51) Int. Cl.
*B01D 61/14* (2006.01)
*B01D 61/22* (2006.01)
(Continued)

(52) U.S. Cl.
CPC ............. *C12N 1/12* (2013.01); *B01D 61/146* (2022.08); *B01D 61/22* (2013.01); *B01D 63/02* (2013.01);
(Continued)

(58) Field of Classification Search
CPC .......... B01D 2317/02; B01D 2317/022; B01D 2317/06; B01D 2317/08; B01D 2319/02;
(Continued)

(56) References Cited

U.S. PATENT DOCUMENTS 2,658,310 A    11/1953  Cook
2,732,661 A     1/1956  Spoehr et al.
(Continued)

FOREIGN PATENT DOCUMENTS

CN    103789195 A     5/2014
EP      0336966 A1   10/1989
(Continued)

OTHER PUBLICATIONS

English language machine translation of CN 103789195, 4 Pages, No Date.*

(Continued)

*Primary Examiner* — Pranav N Patel
(74) *Attorney, Agent, or Firm* — Quarles & Brady LLP

(57) ABSTRACT

Algae harvesting and cultivating systems and methods for producing high concentrations of algae product with minimal energy. In an embodiment, a dead-end filtration system and method includes at least one tank and a plurality hollow fiber membranes positioned in the at least one tank. An algae medium is pulled through the hollow fiber membranes such that a retentate and a permeate are produced.

22 Claims, 16 Drawing Sheets

Related U.S. Application Data

(60) Provisional application No. 62/333,674, filed on May 9, 2016, provisional application No. 62/333,681, filed on May 9, 2016, provisional application No. 62/333,688, filed on May 9, 2016, provisional application No. 62/333,691, filed on May 9, 2016, provisional application No. 62/333,696, filed on May 9, 2016, provisional application No. 62/333,702, filed on May 9, 2016, provisional application No. 62/333,705, filed on May 9, 2016.

(51) Int. Cl.

| | |
|---|---|
| *B01D 65/02* | (2006.01) |
| *C12N 1/12* | (2006.01) |
| *C12M 1/00* | (2006.01) |
| *C12N 1/02* | (2006.01) |
| *B01D 63/02* | (2006.01) |
| *B01D 63/04* | (2006.01) |
| *C12M 1/26* | (2006.01) |
| *C12M 1/34* | (2006.01) |
| *C12M 1/36* | (2006.01) |

(52) U.S. Cl.
CPC .......... *B01D 63/04* (2013.01); *B01D 63/046* (2013.01); *B01D 65/02* (2013.01); *C12M 21/02* (2013.01); *C12M 29/04* (2013.01); *C12M 29/16* (2013.01); *C12M 29/18* (2013.01); *C12M 29/20* (2013.01); *C12M 33/14* (2013.01); *C12M 41/32* (2013.01); *C12M 41/44* (2013.01); *C12M 41/48* (2013.01); *C12M 45/00* (2013.01); *C12M 47/02* (2013.01); *C12N 1/02* (2013.01); *B01D 2311/04* (2013.01); *B01D 2311/06* (2013.01); *B01D 2311/2626* (2013.01); *B01D 2311/2688* (2013.01); *B01D 2313/18* (2013.01); *B01D 2313/26* (2013.01); *B01D 2313/50* (2013.01); *B01D 2315/06* (2013.01); *B01D 2315/08* (2013.01); *B01D 2317/02* (2013.01); *B01D 2317/022* (2013.01); *B01D 2321/04* (2013.01); *B01D 2321/18* (2013.01); *B01D 2321/185* (2013.01); *B01D 2321/40* (2013.01)

(58) Field of Classification Search
CPC .......... B01D 2319/022; B01D 2319/06; B01D 2311/08; B01D 2201/188; B01D 63/02; B01D 63/04; B01D 63/046; B01D 61/146; B01D 61/22; B01D 65/02; B01D 2311/04; B01D 2311/06; B01D 2311/2626; B01D 2311/2688; B01D 2313/18; B01D 2313/26; B01D 2313/50; B01D 2315/06; B01D 2315/08; B01D 2321/04; B01D 2321/18; B01D 2321/185; B01D 2321/40; C02F 1/001; C02F 1/44; C02F 1/441; C02F 1/442; C02F 1/444; C02F 3/06; C02F 3/322; C02F 2301/08; C12N 1/12; C12N 1/02; C12M 21/02; C12M 29/04; C12M 29/16; C12M 29/18; C12M 29/20; C12M 33/14; C12M 41/32; C12M 41/44; C12M 41/48; C12M 45/00; C12M 47/02

See application file for complete search history.

(56) References Cited

U.S. PATENT DOCUMENTS

| | | |
|---|---|---|
| 3,780,471 A | 12/1973 | Ort |
| 3,958,364 A | 5/1976 | Schenck et al. |
| 3,969,844 A | 7/1976 | Fogel et al. |
| 4,087,936 A | 5/1978 | Savins et al. |
| 4,115,949 A | 9/1978 | Avron et al. |
| 4,199,895 A | 4/1980 | Avron et al. |
| 4,236,349 A | 12/1980 | Ramus |
| 4,253,271 A | 3/1981 | Raymond |
| 4,267,038 A | 5/1981 | Thompson |
| 4,324,067 A | 4/1982 | Kessler |
| 4,341,038 A | 7/1982 | Bloch et al. |
| 4,438,591 A | 3/1984 | Kessler |
| 4,473,970 A | 10/1984 | Hills |
| 4,767,539 A | 8/1988 | Ford |
| 4,876,006 A | 10/1989 | Ohkubo et al. |
| 5,151,191 A | 9/1992 | Sunaoka et al. |
| 5,166,067 A | 11/1992 | Ishida et al. |
| 5,248,424 A | 9/1993 | Cote et al. |
| 5,288,399 A | 2/1994 | Schulz |
| 5,393,433 A | 2/1995 | Espenan et al. |
| 5,403,479 A | 4/1995 | Smith et al. |
| 5,480,533 A | 1/1996 | Yoshida |
| 5,541,056 A | 7/1996 | Huntley et al. |
| 5,639,373 A | 6/1997 | Mahendran et al. |
| 5,783,083 A | 7/1998 | Henshaw et al. |
| 5,944,997 A | 8/1999 | Pedersen et al. |
| 5,958,243 A | 9/1999 | Lawrence et al. |
| 6,027,649 A | 2/2000 | Benedek et al. |
| 6,120,688 A | 9/2000 | Daly et al. |
| 6,156,200 A | 12/2000 | Zha et al. |
| 6,193,890 B1 | 2/2001 | Pedersen et al. |
| 6,214,231 B1 | 4/2001 | Cote et al. |
| 6,245,239 B1 | 6/2001 | Cote et al. |
| 6,303,035 B1 | 10/2001 | Cote et al. |
| 6,319,411 B1 | 11/2001 | Cote |
| 6,375,848 B1 | 4/2002 | Cote et al. |
| 6,547,968 B1 | 4/2003 | Rabie et al. |
| 6,550,747 B2 | 4/2003 | Rabie et al. |
| 6,616,843 B1 | 9/2003 | Behmann et al. |
| 6,682,652 B2 | 1/2004 | Mahendran et al. |
| 6,706,189 B2 | 3/2004 | Rabie et al. |
| 6,814,861 B2 | 11/2004 | Husain et al. |
| 6,881,343 B2 | 4/2005 | Rabie et al. |
| 6,899,812 B2 | 5/2005 | Cote et al. |
| 6,964,741 B2 | 11/2005 | Mahendran et al. |
| 7,014,173 B2 | 3/2006 | Rabie et al. |
| 7,025,885 B2 | 4/2006 | Cote et al. |
| 7,063,788 B2 | 6/2006 | Mahendran et al. |
| 7,122,121 B1 | 10/2006 | Ji |
| 7,186,343 B2 | 3/2007 | Rabie et al. |
| 7,198,721 B2 | 4/2007 | Cote et al. |
| 7,378,024 B2 | 5/2008 | Bartels et al. |
| 7,476,322 B2 | 1/2009 | Dimitriou et al. |
| 7,625,157 B2 | 12/2009 | Prichard et al. |
| 7,687,261 B2 | 3/2010 | Hazlebeck et al. |
| 7,820,050 B2 | 10/2010 | Cote et al. |
| 7,879,229 B2 | 2/2011 | Phagoo et al. |
| 7,922,910 B2 | 4/2011 | Cote et al. |
| 8,114,293 B2 | 2/2012 | Phagoo et al. |
| 8,652,331 B2 | 2/2014 | Zha et al. |
| 8,926,844 B2 | 1/2015 | Parsheh et al. |
| 9,181,523 B1 | 11/2015 | Ganuza et al. |
| 9,894,856 B2 | 2/2018 | Javan et al. |
| 10,123,495 B2 | 11/2018 | Ordway et al. |
| 10,501,721 B2 | 12/2019 | Hazlebeck et al. |
| 2002/0034817 A1 | 3/2002 | Henry et al. |
| 2003/0042184 A1 | 3/2003 | McGowan |
| 2005/0061725 A1 | 3/2005 | Liu et al. |
| 2005/0082227 A1 | 4/2005 | Cote et al. |
| 2005/0161388 A1 | 7/2005 | Williams et al. |
| 2006/0008865 A1* | 1/2006 | Cote ............... B01D 65/08 210/295 |
| 2007/0039888 A1 | 2/2007 | Ginzburg et al. |
| 2007/0048859 A1 | 3/2007 | Sears |
| 2007/0075021 A1* | 4/2007 | Johnson ............ B01D 61/18 210/636 |
| 2007/0138070 A1 | 6/2007 | Dimitriou et al. |
| 2008/0009055 A1 | 1/2008 | Lewnard |
| 2008/0086937 A1 | 4/2008 | Hazlebeck et al. |
| 2008/0086938 A1 | 4/2008 | Hazlebeck et al. |
| 2008/0160593 A1 | 7/2008 | Oyler |

(56) References Cited

U.S. PATENT DOCUMENTS

| | | |
|---|---|---|
| 2009/0104098 A1 | 4/2009 | Singh |
| 2009/0166276 A1 | 7/2009 | Abe et al. |
| 2009/0298159 A1 | 12/2009 | Wu et al. |
| 2010/0162620 A1 | 7/2010 | McCaffrey et al. |
| 2010/0190227 A1 | 7/2010 | Dauth et al. |
| 2010/0236137 A1 | 9/2010 | Wu et al. |
| 2011/0049038 A1 | 3/2011 | Aerts et al. |
| 2011/0139715 A1 | 6/2011 | Zha et al. |
| 2011/0247977 A1 | 10/2011 | Song et al. |
| 2011/0309038 A1 | 12/2011 | Inoue |
| 2012/0094361 A1 | 4/2012 | Hu et al. |
| 2012/0125846 A1 | 5/2012 | Suzumura et al. |
| 2012/0231528 A1 | 9/2012 | Muller-Feuga et al. |
| 2013/0146548 A1* | 6/2013 | Cote ............... C02F 3/223 210/791 |
| 2013/0213887 A1 | 8/2013 | Morikawa et al. |
| 2013/0217082 A1 | 8/2013 | Hazlebeck |
| 2013/0228227 A1 | 9/2013 | Kempson et al. |
| 2014/0042074 A1 | 2/2014 | Noh et al. |
| 2014/0065701 A1 | 3/2014 | Kabakian |
| 2014/0206072 A1 | 7/2014 | Severino Do Rosario De Quintanilha Dos Santos et al. |
| 2014/0259896 A1 | 9/2014 | Oney |
| 2015/0315534 A1 | 11/2015 | Vargas, Jr. et al. |
| 2015/0353396 A1 | 12/2015 | Takabatake et al. |
| 2018/0093908 A1 | 4/2018 | Chidambaran et al. |
| 2018/0221825 A1 | 8/2018 | Imamura |

FOREIGN PATENT DOCUMENTS

| | | |
|---|---|---|
| JP | H0623245 A | 2/1994 |
| JP | 2013027378 A | 2/2013 |
| WO | 2014159439 A1 | 10/2014 |

OTHER PUBLICATIONS

P. Srijaroonrat, E. Julien, Y. Aurelle, Unstable secondary oil/water emulsion treatment using ultrafiltration: fouling control by backflushing, Journal of Membrane Science 159 (1999) 11-20. (Year: 1999).*
Extended European Search Report, EP16901893.4, dated Feb. 11, 2020, 4 pages.
International Search Report and Written Opinion, International Application No. PCT/US2016/053203, dated Jan. 30, 2017.
International Searching Authority Invitation to Pay Additional Fees for related International Application No. PCT/US2016/053203 dated Nov. 16, 2016.
Akhondi et al., Evaluation of Fouling Deposition, Fouling Reversibility and Energy Consumption of Submerged Hollow Fiber Membrane Systems with Periodic Backwash, J. Membr. Sci. 452 (2014) pp. 319-333.
Albasi et al., Filtration of Biological Sludge by Immersed Hollow-Fiber Membranes: Influence of Initial Permeability Choice of Operating Conditions, Desalination 146 (2002) pp. 427-431.
Bhave et al., Membrane-Based Energy Efficient Dewatering of Microalgae in Biofuels Production and Recovery of Value Added Co-Products, Environ. Sci. Technol. 46 (2012) pp. 5599-5606.
Bohutskyi et al. Mineral and non-carbon nutrient utilization and recovery during sequential phototrophic-heterotrophic growth of lipid-rich algae. Appl Microbial Biotechnol (2014) 98:5261-5273. (Year 2014).
Buzatu et al., Permeability and Clogging in an Immersed Hollow Fibre Membrane Bioreactor, J. Membr. Sci. 421-422 2012) pp. 342-348.
Current Environmental Issues and Challenges; G. Cao; Roberto Orru, Dept. of Mechanical, Chemical and Materials Engineering, University of Cagliari, Caliari, Italy; Springer Science+Business Media Dordrecht (2014).
Danquah et al., Microalgal Growth Characteristics and Subsequent Influence on Dewatering Efficiency, Chem. Eng. J. 151 (2009) pp. 73-78.
Entech, Control Valve Dynamic Specification, Ver. 3.0, Nov. 1998.
Hendricks, Waler Treatment Unit Processes, CRC Press, Boca Ralon (2011) pp. 539, 560.
Hillis et al., Effects of Backwash Conditions on Out-lo-in Membrane Microfillralion, Desalination 118 (1998) pp. 197-204.
Itokowa et al., Design and Operating Experiences of Municipal MBRS in Europe, Waler Sci. Technol. 58(12) (2008) p. 2319-2327.
Ivanovic et al., Impact of Aeration Rates on Particle Colloidal Fraction in the Biofilm Membrane Bioreactor (BF-MBR), Desalination 231 (2008) pp. 182-190.
Jiang et al., Optimising the Operation of a MBR Pilot Plant by Quantitative Analysis of the Membrane Fouling Mechanism, Waler Sci. Technol. 51 No. 6-7 (2005) pp. 19-25.
Katuri et al., A Novel Anaerobic Electrochemical Membrane Bioreactor (AnEMBR) With Conductive Hollow-fiber Membrane for Treatment of Low-Organic Strength Solutions, Environ. Sci Technol 48 (2014) pp. 12833-12841.
Khirani et al., Effect of Periodic Backwash in the Submerged Membrane Adsorption Hybrid System (SMAHS) for Wastewater Treatment, Desalination 191 (2006) pp. 27-34.
Lee et al., Chilosan Coagulalion—Membrane Filtration of Chlorella Vulgaris, Inl'l J. Hydrogen Energy 37 (2012) pp. 15643-15647.
Pinnekamp et al., Design and Operation of Membrane Bioreactors in Europe (2012).
Prasenjit Mondall; Ajay K. Dalai; Sustainable Utilization of Natural Resources; (2017) Taylor & Francis Group, LLC, Boca Raton, Florida, US.
Raffin et al., Influence of Backwashing, Flux and Temperature on Microfiltration for Wastewater Reuse, Sep. Purif. Technol. 96 (2012) pp. 147-153.
Schoeberl et al., Optimization of Operational Parameters for a Submerged Membrane Bioreactor Treating Dyehouse Wastewater, Sep. Purif. Technol. 44 (2005) pp. 61-68.
Serra et al., Use of Air Sparging to Improve Backwash Efficiency in Hollow-Fiber Modules, J. Membr. Sci. 161 (1999) pp. 95-113.
Smith et al., Design of a Genetic Control System for Optimising Back Flush Durations in a Submerged Membrane Hybrid Reactor, J. Membr. Sci. (2005) pp. 99-106.
Smith et al., A New Approach to Backwash Initiation in Membrane Systems, J. Membr. Sci. 278 (2006) pp. 381-389.
Wu et al., Effects of Relaxation and Backwashing Conditions on Fouling in Membrane Bioreactor, J. Membr. Sci. 324 (2008) pp. 26-32.
Wu et al., Novel Filtration Mode for Fouling Limitation in Membrane Bioreactors, Waler Res. 42 (2008) pp. 3677-3684.
Yigit et al., Effects of Various Backwash Scenarios on Membrane Fouling in a Membrane Bioreactor, Desalination 237 (2009) pp. 346-356.
Zsirai et al., Efficacy of Relation, Backflushing, Chemical Cleaning and Clogging Removal for an Immersed Hollow Fibre Membrane Bioreactor, Waler Res. 46 (2012) pp. 4499-4507.
International Search Report of International Application No. PCT/US21/36608, dated Sep. 15, 2021, 2 pages.
Written Opinion of International Application No. PCT/US21/36608, dated Sep. 15, 2021, 3 pages.
Extended European Search Report of EP Application No. 21202229.7, dated Feb. 2, 2022, 8 pages.

* cited by examiner

BIOLOGICAL AND ALGAE HARVESTING AND CULTIVATION SYSTEMS AND METHODS

CROSS-REFERENCE TO RELATED APPLICATION(S)

This application is a divisional of U.S. patent application Ser. No. 15/273,552, filed Sep. 22, 2016, and titled "Biological and Algae Harvesting and Cultivation Systems and Methods," which claims the benefit of priority to U.S. provisional application Nos. 62/333,674, 62/333,681, 62/333,688, 62/333,691, 62/333,696, 62/333,702 and 62/333,705, filed on May 9, 2016, each of which is incorporated by reference herein and relied upon in its entirety.

STATEMENT OF FEDERALLY SPONSORED RESEARCH OR DEVELOPMENT

This invention was made with government support under award # DE-EE0006314 awarded by the Department of Energy ("DOE"), and under sub-recipient #06-S140633 of prime award # W911NF-14-2-0017 awarded by the Defense Advanced Research Projects Agency ("DARPA"). The government has certain rights in the invention.

BACKGROUND OF THE DISCLOSURE

This present disclosure relates generally to systems and methods for solid or biological slurry filtration, harvesting and cultivation, and more specifically to algae harvesting and cultivation systems and methods.

It has long been recognized that algae harvesting is a major deterrent to realizing practical and economical unicellular algae production. Algae is typically cultivated at 0.02% to 0.5% solid concentration, so large amounts of water must be removed from algae mediums to recover algae product having a high algae concentration (e.g., 3% to 20% solids content). Commercial algae harvesting facilities typically use a centrifuge or a dissolved air floatation system followed by centrifugation to harvest and dewater algae. Centrifuges, however, have high capital and operating costs, and dissolved air floatation systems typically require an addition of a coagulant or flocculent, which increases operating costs. Electrocoagulation, cross flow filtration, biofloc-culation, vibrating membrane filtration and ultrasonic harvesting have been proposed as alternatives to centrifuges and air flotation systems, but an algae harvesting system having low operating costs and minimal energy requirements has remained elusive.

One approach to general solid separation has been outside-in hollow-fiber dead-end filtration in an atmospheric pressure system. These systems include multiple porous hollow fibers, which can be grouped or arranged into modules. The modules can be grouped into cassettes having multiple modules, and the cassettes can be grouped into banks of multiple cassettes. The hollow fibers are immersed in a liquid suspension, and filtrate or permeate can be drawn through walls of the fibers and out of the fiber lumens. A concentrate or retentate with the retained solids remains outside of the hollow fibers. The fibers can be arranged vertically, horizontally, or at an intermediate angle in the liquid suspension. In large hollow-fiber dead-end filtration systems, modules are typically contained in concrete basins or tanks made of metal or plastic to minimize the amount of extra fluid in the system, attain higher concentrations of solids, and reduce the amount of fluid required for membrane washing and cleaning. For large filtration systems, very high volumetric flows are used, resulting in high costs for concrete basins or tanks to contain the hollow-fiber membranes.

Membrane fouling is a significant problem with these hollow fiber dead-end filtration systems. In general, membrane fouling occurs when a solution or particle gets deposited on a surface or in the pores of a membrane causing the membrane's filtration performance to be degraded. Typical methods to reduce membrane fouling with hollow fiber membranes include introduction of air bubbles around the hollow fibers of the membrane, moving the hollow fibers within the liquid suspension, periodic backwashing (also called back-pulsing or backflushing), periodic chemical cleaning, and periodic draining of the liquid suspension. Backwashing is a process in which a fluid is forced through the fibers of the modules typically at a flow rate that is greater than the rate at which permeate is withdrawn. Fibers may be backwashed with a liquid such as water, or a gas (e.g., air) or a mixture of gas and liquid. When water or a liquid permeate is used for the backwashing, the backwash is essentially a recycling process in which the solids production rate is sacrificed during the backwash and during the time it takes to re-filter the water or permeate that was used for the backwash. A water or permeate based backwash system is therefore justified primarily when the cleaning effect is significant. In hollow-fiber dead filtration at atmospheric pressure, the maximum delta or change in pressure for backwashing or permeate flow is typically about eight pounds per square inch (psi), so controls are needed on the pumps to prevent over-pressurizing the membranes and to control the variation in pressure when the permeate and backwash valves are opened and closed.

Periodic backwashing is typically utilized several times per hour in solid filtration systems, e.g. backwash intervals of 15-30 minutes. The backwash offline period is typically 30-120 second and can include the time to open and close valves, the time for the backwash fluid to flow, and the time for any pulsing or adjusting of any pump or compressor during the backwash flow. When water or permeate is used for the backwash, the backwash process is essentially a recycling process in which the solid production rate is sacrificed during the backwash off-line period and during the time to re-filter the water or the permeate that was used in the backwash. Backwashing is therefore justified to the extent that the cleaning effect is significant. Attempts to optimize backwashing in hollow fiber dead-end filtration systems have indicated that as suspended solids concentration is increased, the backwash off-line period is typically increased to allow for a longer time for backwash flow.

Pumps are typically used to provide a permeate or liquid backwash. Systems utilizing pumps, however, can be very complex and costly, and often utilize variable frequency drive ("VFD") pumps. For these systems to work without over-pressure, multiple valves typically need to be open and closed virtually simultaneously. Air pressure has been proposed as an alternative to liquid backwash, but the cost of pressurizing air is much greater than liquid, and introducing air into permeate channels can cause problems.

Unlike ceramic or metallic filtering membranes, the backwash pressure in hollow fiber membranes is limited to avoid damaging the fiber membranes. The backwash pressure used in hollow fiber membrane systems is typically well below the maximum to avoid membrane damage from spikes or transients when the backwash is started and stopped. Complicated controls are required to minimize these transients and pressure spikes. Furthermore, the low-pressure tolerance of hollow fibers prevents the use of short, high-pressure back-pulses that are used in ceramic or metallic membrane systems to remove fouling by a pressure shock.

Biological slurries such as algae or activated sludge are typically more difficult to filter to high suspended solids concentrations than inorganic slurries. Natural or synthetic flocculants are typically required to attain greater than 1% suspended solids. The addition of flocculent, however, is costly and can negatively impact the processing or value of the algae product. Activated sludge is a consortium of microbes in which natural bioflocculation is attained, so hollow fiber dead-end filtration can be used for activated sludge. However, the maximum concentration of suspended solids with naturally flocculated activated sludge is typically about 3% to 4.5% when dead-end hollow fiber filtration is used for activated sludge.

Non-flocculent, cross-flow membrane filtration systems have been used in an attempt to attain a high concentration of algae product. Cross-flow filtration systems, however, have higher energy requirements and higher operating costs than dead-end filtration systems. For example, typical cross-flow filtration systems can require 0.4 to 7 kWh/m3 of energy to operate. Cross-flow filtration systems are therefore less economical than dead-end hollow fiber systems. In addition, cross-flow systems have higher shear stress and have recirculation in the cross flow pump loop, which can damage algae cells.

Most hollow-fiber liquid filtration systems are single stage. Multistage hollow fiber solid filtrations systems have been used with constant flux in each stage to achieve higher average flux. These constant flux and constant area multistage systems typically produce low solid concentration (e.g., less than 1% suspended solids), and require active transmembrane pressure control and active fluid flowrate control for each stage, which increases the cost and complexity of such systems.

Production of algal products is often enhanced by two-stage cultivation in which algae is pretreated before entering a second stage or the algae media is altered in the second stage. In some cases, stress from media changes, such as nitrogen deprivation, salinity, or pH is used to induce formation of a product. In other cases, exposure to stress such as shear, ozone, bleach, or high light is used to induce formation of a product. If the media is changed, then recovery and recycle of the media for cultivation is prevented because salts or other dissolved solids are added to the media, and high operating costs are incurred because chemicals must be added to each batch to modify the media. If exposure to stress is used, then the amount of chemicals or size of the second stage pretreatment system is large because the algae are cultivated under dilute conditions.

Aquaculture facilities often require live feeds to feed fish, shellfish, and larva of fish or shellfish. These algae could be produced more economically in centralized facilities, but shipment of dilute cultures is expensive, and algae harvesting processes damage the algae or require flocculants, so concentrated algae cultures are not available. Dead algae products are centrally produced and shipped for use in aquaculture facilities, but these products are not as effective as live algae. Thus, typical aquaculture facilities must cultivate algae for feed in addition to cultivating fish or shellfish.

Concentrated algae slurries attained in harvesting and dewatering contain extra-cellular media, and the algae slurry is often dried to obtain an algae product. The dissolved solids in the extra-cellular media increase the ash content of the dried algae product and can add undesirable compounds such as metal salts to the product. In some cases, algae slurries are processed to lyse the cells or extract a product. In many of these processes, the lysis or extraction is more effective with a particular ionic composition, pH, or osmotic strength in the extra cellular media. Adjustment of the media is difficult because it typically involves re-suspension in a new media followed by another expensive and energy-intensive harvesting step.

In view of the above, it should be appreciated that new and improved algae harvesting and cultivation systems and methods are needed.

SUMMARY OF THE DISCLOSURE

In one aspect of the present disclosure, an algae harvesting system provides at least one treatment tank and at least one membrane filtration module positioned inside the at least one treatment tank. The filtration module includes a plurality of hollow fiber membranes defining lumens. The system is configured to perform dead-end filtration of an algae slurry contained in the treatment tank by pulling a substantially algae-free permeate through pores of the plurality of hollow fiber membranes so that the permeate flows inside the lumens of the hollow fiber membranes and a retentate of the algae slurry is produced outside the lumens of the hollow fiber membranes. The system is further configured to perform a backwash sequence in which a backwash fluid flows inside the lumens of the hollow fiber membranes and is pushed through the pores of the hollow fiber membranes to remove any foulants that have accumulated on the hollow fiber membrane. The backwash sequence includes an off-line period of less than about twelve seconds.

In another aspect of the present disclosure, an algae harvesting system provides at least one treatment tank and at least one membrane filtration module positioned inside the treatment tank. The filtration module includes a plurality of hollow fiber membranes defining lumens. The system is configured to perform dead-end filtration of an algae slurry contained in the treatment tank by pulling a substantially algae-free permeate through pores of the hollow fiber membranes so that the permeate flows inside the lumens of the hollow fiber membranes and a retentate of the algae slurry is produced outside the lumens of the hollow fiber membranes. The system is further configured to perform a backwash sequence in which a backwash fluid flows inside the lumens of the hollow fiber membranes and is pushed through the pores of the hollow fiber membranes to remove any foulants that have accumulated on the plurality of hollow fiber membranes. The backwash sequence includes an interval of less than about three minutes, and the interval includes the time between the start of one backwash cycle and the start of a next backwash cycle.

In an additional aspect of the present disclosure, an algae harvesting method includes, in a dead end filtration process, pulling a substantially algae-free permeate from an algae slurry through pores of a plurality of hollow fiber membranes positioned inside the treatment tank so that the permeate flows inside lumens of the hollow fiber membranes and a retentate of the algae slurry is produced outside the lumens of the plurality of hollow fiber membranes. The method further includes, in a backwash sequence, pushing a backwash fluid through pores of the hollow fiber membranes to remove any foulants that have accumulated on the plurality of hollow fiber membranes. The backwash sequence includes an interval of less than about three minutes and an off-line period of less than about twelve seconds.

In yet another aspect of the present disclosure, an algae harvesting system provides at least one treatment tank defining a plurality of filtration stages including a first filtration stage and a second filtration stage. The first filtration stage includes a first membrane filtration module positioned inside the treatment tank. The first membrane filtration module includes a first plurality of hollow fiber membranes having a first total outside filtration area and defining lumens. The first module also includes a retentate outlet, and a permeate outlet. The second filtration stages includes a second at membrane filtration module positioned inside the treatment tank. The second membrane filtration module includes a second plurality of hollow fiber membranes having a second total outside filtration area and defining lumens. The second module also includes an inlet coupled fluidly to the retentate outlet of the first filtration stage, a retentate outlet, and a permeate outlet. The system is configured to perform dead-end filtration of an algae slurry in the treatment tank by pulling permeate through pores of the first hollow fiber membranes at a first flux so that the permeate flows inside the lumens of the first hollow fiber membranes and a first retentate is produced outside the lumens of the first hollow fiber membranes, allowing at least a portion of the first retentate to flow from the retentate outlet of the first filtration stage to the inlet of the second filtration stage, and (iii) pulling permeate through pores of the second hollow fiber membranes at a second different flux so that the permeate flows inside the lumens of the second hollow fiber membranes and a second retentate is produced outside the lumens of the second hollow fiber membranes.

In still another aspect of the present disclosure, an algae harvesting method is provided for performing dead-end filtration in an algae harvesting system having at least one treatment tank defining a plurality of filtration stages including at least a first filtration stage and a second filtration stage, wherein the first filtration stage has a first plurality of hollow fiber membranes positioned inside the at least one treatment tank and the second filtration stage has a second plurality of hollow fiber membranes positioned inside the at least one treatment tank. The method includes in a dead-end filtration process, pulling permeate at the first filtration stage from an algae slurry through pores of the first hollow fiber membranes at a first flux so that the permeate flows inside the lumens of the first a plurality of hollow fiber membranes and a first retentate is produced outside the lumens of the first hollow fiber membranes and flowing the first retentate from the first filtration stage to the second filtration stage. The method additionally includes, in a dead-end filtration process and in fluid parallel with the pulling in the first filtration stage, pulling at the second filtration stage a permeate from the algae slurry through pores of the second plurality of hollow fiber membranes at a second different flux so that a second retentate is produced outside the lumens of the second plurality of hollow fiber membranes.

In another aspect of the present disclosure an algae harvesting system provides at least one treatment tank having an algae slurry feed inlet, and a retentate outlet. The system further includes (i) at least one membrane filtration module positioned inside the treatment tank, wherein the membrane filtration module includes a plurality of hollow fiber membranes defining lumens (ii) a permeate tank positioned such that a level of permeate fluid contained in the permeate tank is below a level of algae slurry contained in the at least one treatment tank; (iii) at least one permeate conduit coupled fluidly to the permeate tank and to the plurality of hollow fiber membranes; and (iii) a gas purge conduit coupled fluidly to the at least one permeate conduit such that a pressure increase in the at least one permeate conduit also increases a pressure in the at least one purge conduit so that any gas that has accumulated in the at least one permeate conduit can be pushed through the gas purge conduit. The system is configured to perform dead-end filtration of the algae slurry contained in the treatment tank by siphoning a substantially algae-free permeate through pores of the plurality of hollow fiber membranes so that the permeate flows inside the lumens of the hollow fiber membranes, through the permeate conduit to the permeate tank, and a retentate of the algae slurry is produced outside the lumens of the hollow fiber membranes. The system is further configured to perform a backwash sequence in which (a) a backwash fluid flows inside the lumens of the hollow fiber membranes and is pushed through the pores of the hollow fiber membranes to remove any foulants that have accumulated on the hollow fiber membranes, and (b) any gas in the at least one permeate conduit is pushed through the gas purge conduit.

Another aspect of the present disclosure provides an algae harvesting system including (i) at least one treatment tank for an algae slurry, (ii) at least one membrane filtration module positioned inside the treatment tank, the membrane filtration module including a plurality of hollow fiber membranes defining lumens; (iii) a backwash tank positioned such that a level of backwash fluid contained in the backwash tank is above a level of the algae slurry in the treatment tank, and (iv) at least one backwash conduit coupled fluidly to the backwash tank and to the hollow fiber membranes. The system is configured to perform dead-end filtration of the algae slurry in the treatment tank by pulling a substantially algae-free permeate through pores of the plurality of hollow fiber membranes so that the permeate flows inside the lumens of the plurality of hollow fiber membranes and a retentate of the algae slurry is produced outside the lumens of the hollow fiber membranes. The system is further configured to perform a backwash sequence in which the backwash liquid (a) gravity flows from the backwash tank, through the backwash conduit, to inside the lumens of the plurality of hollow fiber membranes, and (b) is pushed through the pores of the plurality of hollow fiber membranes to remove any foulants that have accumulated on the plurality of hollow fiber membranes.

In a further aspect of the present disclosure, an algae harvesting system provides (i) at least one treatment tank, (ii) a cassette positioned inside the at least one treatment tank, wherein the cassette includes a plurality of membrane filtration modules coupled fluidly in parallel via a cassette header, wherein each of the filtration modules has hollow fiber membranes defining lumens, and wherein the total outside surface area of all of the hollow fiber membranes of the cassette is about 500 m$^2$ to 2200 m$^2$, (iii) a single permeate valve coupled fluidly to the header; and (iv) a single backwash valve coupled fluidly to the header. The system is configured to perform dead-end filtration of an algae slurry contained in the treatment tank by pulling permeate through pores of the hollow fiber membranes so that the permeate flows inside the lumens of the hollow fiber membranes and retentate is produced outside the lumens of the hollow fiber membranes. The system is further configured to perform a backwash sequence in which a backwash fluid flows inside the lumens of the hollow fiber membranes and is pushed through the pores of the hollow fiber membranes so as to remove any foulants that have accumulated on the hollow fiber membranes, wherein the actuation time for the single backwash valve and the single permeate valve is about three seconds or less, and the actuation time includes the time to (i) open the single backwash valve and the single permeate valve or (ii) close the single backwash valve and the single permeate valve.

In another aspect of the present disclosure, an algae harvesting system provides (i) at least one treatment tank; (ii) a bank positioned inside the at treatment tank, wherein the bank includes a first cassette and a second cassette, wherein the first cassette and the second cassette are coupled fluidly in parallel via a bank header, wherein the first cassette includes a first plurality of membrane filtration modules coupled fluidly in parallel via a first cassette header and the second cassette includes a second plurality of membrane filtration modules coupled fluidly in parallel via a second cassette header, wherein each of the first and second plurality of membrane filtration modules has hollow fiber membranes defining lumens, and wherein the total outside surface area of all of the hollow fiber membranes of the bank is about 500 $m^2$ to 10,000 $m^2$; (iii) a single permeate valve coupled fluidly to the bank header; and (iv) a single backwash valve coupled fluidly to the bank header. The system is configured to perform dead-end filtration of an algae slurry in the treatment tank by pulling permeate through pores of the hollow fiber membranes so that the permeate flows inside the lumens of the hollow fiber membranes and a retentate is produced outside the lumens of the hollow fiber membranes. The system is further configured to perform a backwash sequence in which a backwash fluid flows inside the lumens of the hollow fiber membranes and is pushed through the pores of the hollow fiber membranes so as to remove any foulants that have accumulated on the hollow fiber membranes, wherein the actuation time for the single backwash valve and the single permeate valve is about three seconds or less, and the actuation time includes the time to (i) open the single backwash valve and the single permeate valve or (ii) close the single backwash valve and the single permeate valve.

In yet an additional aspect of the present disclosure, an algae harvesting system provides a first lined earthen treatment tank defining a first filtration stage and a second treatment tank defining a second filtration stage. The first filtration stage includes (i) a first at least one membrane filtration module positioned inside the earthen treatment tank, wherein the first filtration module includes first hollow fiber membranes having a first total outside filtration area and defining lumens, (ii) a retentate outlet, and (iii) a permeate outlet. The second filtration stage includes (i) a second at least one membrane filtration module positioned inside the second treatment tank, wherein second filtration module includes second hollow fiber membranes having a second total outside filtration area and defining lumens, (ii) an inlet coupled fluidly with the retentate outlet of the first filtration stage, (iii) a retentate outlet, and (iv) a permeate outlet. The system is configured to perform dead-end filtration of an algae slurry contained in the earthen treatment tank and the second treatment tank by pulling permeate through pores of the first and second plurality of hollow fiber membranes so that retentate is produced outside the lumens of the first and second plurality of hollow fiber membranes.

In still another aspect of the present disclosure, an algae harvesting and cultivation system provides a first algae cultivator defining a first cultivation stage, wherein the first cultivation stage includes a first at least one cultivation device having a first algae cultivation media for cultivating algae. The algae harvesting and cultivation system further provides a first dead-end filtration system in fluid communication with the first cultivation stage such that the first dead-end filtration system receives at least a portion of the algae cultivated from the first cultivation stage, wherein the first dead-end filtration system has a first plurality of hollow fiber membranes and is configured to dead-end filter the algae received from the first cultivation stage through the first plurality of hollow fiber membranes so as to produce a first retentate and a first permeate. The algae harvesting and cultivation system is constructed and arranged such that the first permeate flows back to the first cultivation stage. The algae harvesting and cultivation system further includes a second algae cultivator defining a second cultivation stage, wherein the second cultivation stage is in fluid communication with the first dead-end filtration system such that the second cultivation stage receives the first retentate, wherein the second cultivation stage includes a second at least one cultivation device having a second media for cultivating additional algae using the first retentate. The algae harvesting and cultivation system further includes a second dead-end filtration system in fluid communication with the second cultivation stage such that the second dead-end filtration system receives at least a portion of the additional algae cultivated in the second cultivation stage, wherein the second dead-end filtration system has a second plurality of hollow fiber membranes and configured to dead-end filter the additional algae received from the second cultivation stage so as to produce a second permeate and a second retentate. The algae harvesting and cultivation system is further constructed and arranged such that the second permeate flows back to the second cultivation stage.

In a further aspect of the present disclosure, an algae harvesting and cultivation system includes (i) an algae cultivator having at least one cultivation device having a cultivation media for growing algae to produce an algae slurry, and (ii) at least one treatment tank defining a plurality of filtration stages including at least a first filtration stage and a second filtration stage, wherein the first filtration stage is in fluid communication with the algae cultivator such that the first filtration stage receives the algae slurry. The first filtration stage includes (a) a first at least one membrane filtration module positioned inside the treatment tank, wherein the first membrane filtration module includes a first plurality of hollow fiber membranes having a first total outside filtration area and defining lumens, (b) a retentate outlet, and (c) a permeate outlet. The second filtration stage includes (a) a second at least one membrane filtration module positioned inside the treatment tank, wherein the second membrane filtration module includes a second plurality of hollow fiber membranes having a second total outside filtration area and defining lumens, (b) an inlet coupled fluidly to the retentate outlet of the first filtration stage, (c) a retentate outlet, and (d) a permeate outlet. The algae harvesting and cultivation system is configured to cultivate algae and perform dead-end filtration of the algae slurry by allowing the algae slurry to flow from the algae cultivator to the first filtration stage, pulling permeate through pores of the first hollow fiber membranes at a first flux so that a first retentate is produced outside the lumens of the first hollow fiber membranes, allowing at least a portion of the first retentate to flow from the first filtration stage retentate outlet to the second filtration stage retentate inlet, and pulling permeate through pores of the second hollow fiber membranes at a second flux so that a second retentate is produced outside the lumens of the second plurality of hollow fiber membranes, and) allowing the permeate from the first and second filtration stages to flow back to the algae cultivator for use in the cultivation media for growing algae.

In another aspect of the present disclosure, an algae harvesting system provides (i) at least one treatment tank having a rinse fluid inlet and (ii) a retentate outlet, (iii) at least one membrane filtration module positioned inside the treatment tank, wherein the membrane filtration module includes a plurality of hollow fiber membranes defining lumens; (iv) a source of algae slurry in a media, the source of algae slurry coupled fluidly to the at least one treatment tank such that the at least one treatment tank can receive the algae slurry; (v) a source of rinse fluid, the source of rinse fluid coupled fluidly to the rinse fluid inlet of the at least one treatment tank such that the at least one treatment tank can receive the rinse fluid; and (vi) a media sensor configured to sense the concentration of media in the algae slurry. The system is configured to (a) perform dead-end filtration of the algae slurry received in the treatment tank by pulling a substantially algae-free permeate through pores of the hollow fiber membranes so that the permeate flows inside the lumens of the hollow fiber membranes and a retentate of the algae slurry is produced outside the lumens of the hollow fiber membranes, (b) perform a backwash sequence in which a backwash liquid flows inside the lumens of the hollow fiber membranes and is pushed through the pores of the hollow fiber membranes to remove any foulants that have accumulated on the plurality of hollow fiber membranes, and (c) perform a rinse sequence in which (i) the treatment tank stops receiving the algae slurry from the source of algae slurry, and (ii) the treatment tank receives the rinse fluid from the source of rinse fluid through the rinse fluid inlet until the at least one media sensor senses that at least ninety percent of the media has been replaced with the rinse fluid.

In yet an additional aspect of the present disclosure, an algae harvesting system provides at least one treatment tank defining a plurality of filtration stages including at least a first filtration stage and a second filtration stage. The first filtration stage includes (i) a first at least one membrane filtration module positioned inside the at treatment tank, wherein the first membrane filtration module includes a first plurality of hollow fiber membranes having a first total outside filtration area and defining lumens, (ii) a retentate outlet, and (iii) a permeate outlet. The second filtration stage includes (i) a second at least one membrane filtration module positioned inside the treatment tank, wherein the second membrane filtration module includes a second plurality of hollow fiber membranes having a second total outside filtration area and defining lumens, (ii) a retentate inlet coupled fluidly to the retentate outlet of the first filtration stage, (ii) a rinse fluid inlet, (iii) a retentate outlet, and (iv) a permeate outlet. The algae harvesting system further provides a media sensor configured to sense a concentration of media in an algae slurry in the at least one treatment tank. The system is configured to perform dead-end filtration of the algae slurry contained in the treatment tank by (i) pulling permeate through pores of the first hollow fiber membranes at a first flux so that the permeate flows inside the lumens of the first hollow fiber membranes and a first retentate is produced outside the lumens of the first hollow fiber membranes, (ii) allowing at least a portion of the first retentate to flow through the retentate outlet of the first filtration stage to the inlet of the second filtration stage, and (iii) pulling permeate through pores of the second hollow fiber membranes at a second flux so that the permeate flows inside the lumens of the second hollow fiber membranes and a second retentate is produced outside the lumens of the second hollow fiber membranes. The system is further configured to perform a backwash sequence in which a backwash liquid flows (i) inside the lumens of the first plurality of hollow fiber membranes and is pushed through the pores of the first plurality of hollow fiber membranes to remove any foulants that have accumulated on the first plurality of hollow fiber membranes, and (ii) inside the lumens of the second plurality of hollow fiber membranes and is pushed through the pores of the second plurality of hollow fiber membranes to remove any foulants that have accumulated on the second plurality of hollow fiber membranes. The system is additionally configured to perform a rinse sequence in which (i) the first retentate stops flowing from the first filtration stage to the second filtration stage, and (ii) the rinse fluid flows to the second filtration stage through the rinse fluid inlet until the media sensor senses that that at least ninety percent of the media has been replaced with the rinse fluid.

In still another aspect of the present disclosure, an algae harvesting and cultivation system provides (a) an algae cultivator including at least one cultivation device having a cultivation media for growing algae to produce an algae slurry, and (b) at least one treatment tank defining a plurality of filtration stages including at least a first filtration stage and a second filtration stage, wherein the first filtration stage is in fluid communication with the algae cultivator such that the first filtration stage receives the algae slurry. The first filtration stage includes (i) a first at least one membrane filtration module positioned inside the treatment tank, wherein the first membrane filtration module includes a first plurality of hollow fiber membranes having a first total outside filtration area and defining lumens, (ii) a retentate outlet, and (iii) a permeate outlet. The second filtration stage includes (i) a second at least one membrane filtration module positioned inside the treatment tank, wherein the second membrane filtration module includes a second plurality of hollow fiber membranes having a second total outside filtration area and defining lumens, (ii) an inlet coupled fluidly to the retentate outlet of the first filtration stage, (iii) a retentate outlet, and (iv) a permeate outlet. The algae harvesting and cultivation system further provides a live algae container coupled fluidly to the second filtration stage to receive the second retentate. The system is configured to cultivate algae and perform dead-end filtration of the algae slurry by: (i) allowing the algae slurry to flow from the algae cultivator to the first filtration stage, (ii) pulling permeate through pores of the first plurality of hollow fiber membranes at a first flux so that a first retentate is produced outside the lumens of the first plurality of hollow fiber membranes, (iii) allowing at least a portion of the first retentate to flow from the first filtration stage retentate outlet to the second filtration stage retentate inlet, (iv) pulling permeate through pores of the second plurality of hollow fiber membranes at a second flux so that a second retentate is produced outside the lumens of the second plurality of hollow fiber membranes, (v) allowing the permeate from the first and second filtration stages to flow back to the algae cultivator for use in the cultivation media for growing algae, and (vii) flowing live algae in the second retentate from the second filtration stage to the live algae container.

One advantage of the present disclosure is to provide algae harvesting systems and methods that reduce backwashing periods and/or intervals while producing high concentrations of algae product.

It is also an advantage of the present disclosure to provide systems and methods for harvesting algae that are low cost and low energy input.

It is yet another advantage of the present disclosure to provide dead-end, hollow fiber membrane filtration systems and methods for algae harvesting.

It is yet another advantage of the present invention to provide a high algae concentration product from a dead-end, hollow fiber membrane system.

It is additionally an advantage of the present disclosure to provide systems and methods that attain concentrations of algae greater than 3% using hollow fiber dead-end filtration systems without the addition of flocculants or coagulants.

It is another advantage of the present disclosure to provide hollow fiber dead-end filtration systems that obtain concentration ratios between the inlet algae slurry suspended solids and outlet algae slurry suspended solids of greater than 50:1 without the addition of flocculants or coagulants.

It is still another advantage of the present disclosure to provide gravity backwash systems so as to reduce the complexity and cost of hollow fiber dead-end filtration systems and to enable shorter backwash off-line periods.

It is still another advantage of the present disclosure to provide a gravity backwash systems to eliminate the need to size banks so that one is always in backwash, or the need to provide separate systems for variable backwash intervals in different cassettes or banks.

It is yet an additional advantage of the present disclosure to reduce the cost and complexity of hollow-fiber filtration systems through a gravity-driven siphon system to pull permeate through a hollow-fiber membranes.

It is additionally an additional advantage of the present disclosure to provide a gravity-driven siphon system to pull permeate through a hollow-fiber membranes with variable permeate flow.

It is another advantage of the present disclosure to provide a gravity-driven siphon system that enables a higher flux or lower energy use in a hollow-fiber filtration system.

It is yet an additional advantage of the present disclosure to provide gravity backwash systems that allow operation at maximum backwash pressures due to the pressure being inherently limited by the height of the backwash systems and no pressure spikes existing from transients while pumps or control valves are being adjusted.

It is therefore an additional advantage of the present disclosure to reduce the cost and complexity of backwash systems for hollow fiber dead-end filtration systems and methods.

It is another advantage of the present disclosure to provide membrane filtration systems and methods that enable shorter backwash off-line periods, to provide higher backwash pressure without potential damage from transients, and to enable variable backwash intervals in a multistage filtration plant without separate backwash systems.

It is a further advantage of the present disclosure to provide hollow fiber membrane filtration systems and methods with optimal sizing of banks and cassettes so that the systems and method operate economically.

It is another advantage of the present disclosure to provide hollow fiber membrane filtration systems and methods with more valves with shorter actuation times so as to increase the average flux of the system, which can reduce the cost per amount of permeate removed by increasing the number of valves to attain a shorter backwash off-line period.

It is yet an additional advantage of the present disclosure to provide hollow fiber membrane filtration systems and methods having modules grouped into cassettes and banks such that the cost for filtration is reduced.

Yet another advantage of the present disclosure is to provide multistage hollow fiber dead-end filtration systems having variable flux in each stage (and in certain embodiments decreasing area in each stage) to increase the average flux per module.

It is therefore an additional advantage of the present disclosure to provide multistage hollow fiber dead-end filtration systems that obtain higher flux and lower cost.

Still further, an advantage of the present disclosure is to provide shorter valve opening and/or closing times, thereby increasing the overall system flux and enabling shorter backwash periods and/or intervals.

A further advantage of the present disclosure is to produce concentrated algae slurries by harvesting and dewatering the algae in dead-end filtration systems and then re-cultivating by dilution with the same growth media or a different growth media and the live algae slurries can be stored before re-cultivation.

Another advantage of the present disclosure therefore is that live algae slurries can be used to retain a concentrated inoculum for recovery from system upsets the concentrated slurries represent and the concentrated algae slurries produced by harvesting and dewatering in dead-end filtration systems slurries can be stored and re-cultivated and a 50 to 400-fold reduction in volume is achieved relative to the cultivation system thereby enabling concentrated algae slurries to be efficiently shipped to another location.

An advantage of the present disclosure is therefore to utilize hollow fiber dead-end filtration systems and methods to produce concentrated live algae slurries that can be stored for use at a later time, and to utilize hollow fiber dead-end filtration to produce concentrated live algae slurries that can be shipped for use at another location.

It is therefore an additional advantage of the present disclosure to utilize hollow fiber dead-end filtration to produce concentrated live algae slurries of greater than 1% suspended solids.

It is still another advantage of the present disclosure to provide hollow fiber dead-end filtration systems that are used to separate an algae cultivation media and to replace the cultivation media with a second cultivation media for continued cultivation under different conditions.

A further advantage of the present disclosure is to provide hollow fiber dead-end filtration systems and methods for algae harvesting that reduce energy use so that inclusion of rinses and media adjustments at an intermediate or final filtration stage results in minimal energy penalty, and to recover most or all of the dissolved solids in a permeate flow during algae harvesting and dewatering with hollow fiber dead-end filtration.

Further, it is an advantage of the present disclosure to provide multistage hollow fiber membrane algae harvesting systems and methods that utilize a rinse liquid such as water at an intermediate and/or final stage so that extracellular water can be diluted by the rinse water and dissolved solids concentration can become very low.

Yet further, it is an advantage of the present disclosure to provide multistage hollow fiber membrane algae harvesting systems and methods that utilize a rinse liquid such as water near the end of the filtration so that the amount of rinse water required is relatively small (e.g., small relative to pond volume) and/or the rinse water can replace a portion of any evaporative losses resulting from pond cultivation.

It is yet another advantage of the present disclosure to reduce the dissolved solids content in the concentrated algae slurry obtained in harvesting and dewatering with hollow fiber dead-end filtration, and to alter the dissolved solids content of the concentrated algae slurry obtained in harvesting and dewatering with hollow fiber dead-end filtration.

It is still a further advantage of the present disclosure to utilize one or more low cost lined ponds in a dead-end multistage hollow fiber filtration system instead of just concrete, metal, and/or plastic tank(s), and to use such earthen lined ponds as the containment tank for the early stages of the multistage system.

It should be appreciated that utilizing such lined earthen ponds in earlier stages of a multi-stage system while later or final stage(s) are contained in a concrete, metal and or plastic basin reduces the overall cost of the systems and methods of the present disclosure.

Further still, it is an advantage of the present disclosure to provide algae harvesting systems and methods that reduce complexity, decreases costs and improves efficiency and yields.

Additional features and advantages of the present invention are described in, and will be apparent from, the following Brief Description of the Drawings & Detailed Description of the Invention.

DETAILED DESCRIPTION

The following describes one or more example embodiments of the present disclosure, as shown in the accompanying drawings described briefly above.

Figure 1:
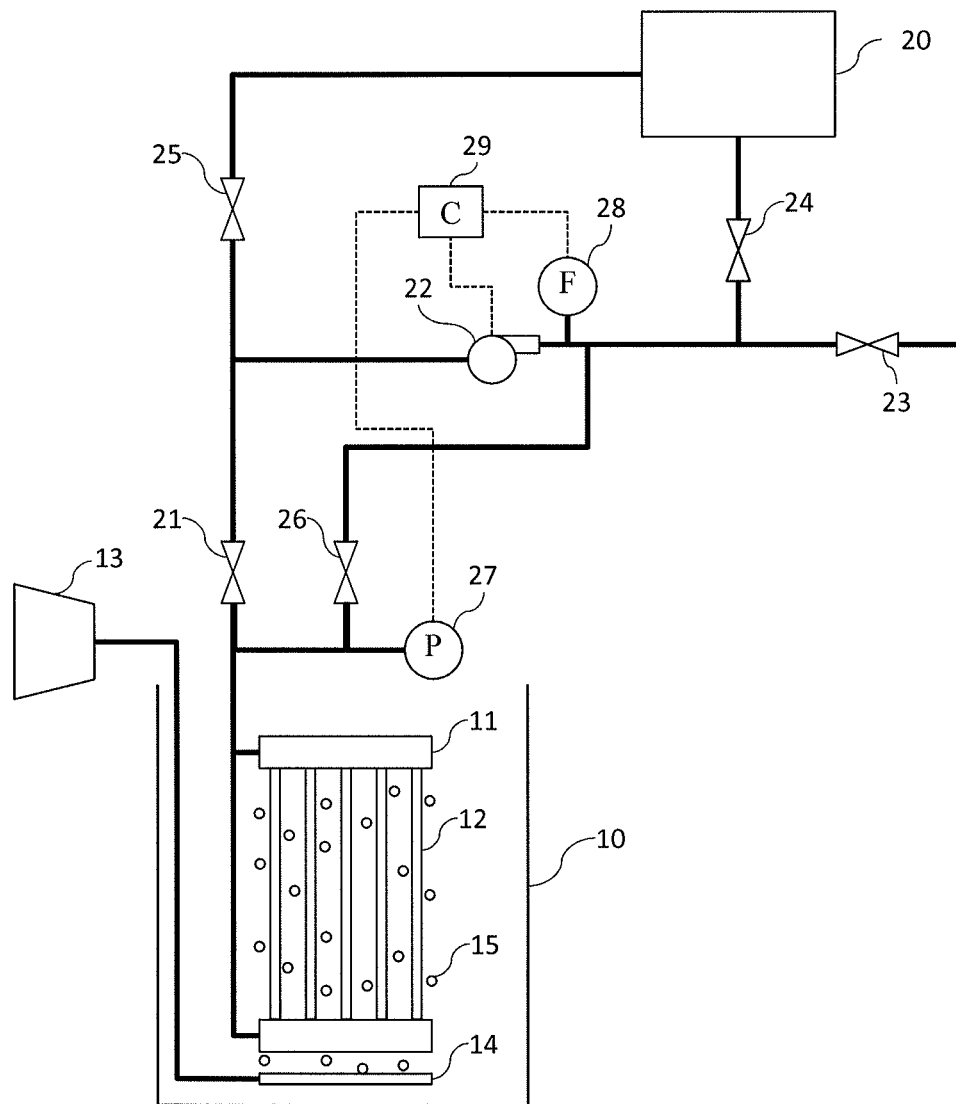
FIG. 1 is a schematic diagram illustrating an embodiment of a hollow fiber dead-end filtration system of the present disclosure having a single permeate pump.

FIG. 1 illustrates one non-limiting embodiment of a hollow-fiber dead-end filtration system of the present disclosure. The system includes a treatment tank 10 structured and arranged to receive and treat a liquid feed containing suspended solids (e.g., a biological slurry or algae slurry/feed received, for example, from an algae source or container that is in fluid communication with tank 10 via at least one conduit operating with an in-feed valve) to produce a filtered permeate substantially free of suspended solids and a retentate with a higher suspended solids content than the liquid feed. A plurality of submerged hollow fiber membranes 12 are contained or positioned within treatment tank 10. In some embodiments, the submerged hollow fiber membranes 12 can be arranged into one or more module 11 that is contained, supported or held in treatment tank 10. The outer surface of the hollow fiber membranes 12 is in contact with the liquid feed and retentate. The one or more module 11 can also be arranged into one or more cassette. The one or more module 11 in the illustrated embodiment can include headers attached to each hollow fiber membrane 12 so as to create a watertight connection between the outside of the membranes 12 and a permeate channel in the header.

To perform dead-end filtration, permeate is pumped or pulled through pores of the hollow fiber membranes so that permeate is withdrawn through the inside of the lumens of the hollow fiber membranes and retentate is produced outside the lumens of the hollow fiber membranes (e.g., inside the treatment tank). A blower 13 can push air through a conduit and a distributer 14 to create air bubbles 15 that are released below the hollow fibers to create fluid movement and movement of the hollow fibers, which aids in reducing fouling and improving backwash efficiency. The air bubbles can be released continuously, intermittently, or only during the backwash cycles.

During the filtration, valves 21 and 23 are open, valves 25 and 26 are closed, and permeate is withdrawn through at least one conduit via pump 22. Valve 24 is opened and valve 23 is closed intermittently to maintain the fluid level in a permeate holding tank 20. A controller 29 (e.g., a programmable logic controller) controls permeate pump 22 based upon the permeate flow rate measured by flow meter 28 and the suction or negative pressure measured via pressure transducer 27.

A backwashing sequence is initiated by opening valve 25, closing valve 21, closing valves 24 and 23, and opening valve 26. Permeate pump 22 pumps permeate from permeate holding tank 20 through at least one conduit to the inside of the lumens defined by hollow fiber membranes 12 of module 11. Controller 29 (e.g., a programmable logic controller) controls the flow rate of pump 22 to maintain a desired backwash pressure, as measured by pressure transducer 27. Once the backwash flow time is complete, withdrawal of the permeate is resumed by opening valves 21 and 23, and closing valves 25 and 26. It should be appreciated that in certain embodiments, multiple modules 11 can be connected in parallel in a cassette so that the entire cassette can be backwashed at the same time. Certain embodiments can also include multiple cassettes connected in parallel in a bank so that the multiple cassettes can be backwashed at the same time.

In one non-limiting embodiment of the system of FIG. 1, the backwash off-line period includes the time between stopping permeate flow from module 11 and restarting permeate flow from module 11. In various embodiments, the backwash off-line period includes one or more of: (i) the time to open and close valves 21, 23, 24, 25, and 26 for backwash; (ii) the time to reach the backwash pressure; (iii) the time for the backwash flow, (iv) the time to open and close valves 21, 23, 24, 25, and 26 for permeate flow; (v) the time to lower the pressure in the permeate lines to resume the permeate flow. In one particular non-limiting embodiment, the backwash off-line period for the system of FIG. 1 includes the time for each of (i) to (v) above. The backwash interval in an embodiment includes the time between the start of one backwash cycle and the start of a next backwash cycle.

It should be appreciated that controller 29 can in various embodiments include one or more controller, which can be programmed or configured to operate with one or more of the valves, the blower, the pressure transducer, the flow meter, the pump, any sensors and/or any other system components so as to perform various functions of the system including valving, pumping, backwashing, rinsing, filtration, permeate flow, chemical cleaning or any other system functions. In an embodiment, the one or more controller can include at least one processor and at least one memory device which stores instructions, which when executed by the at least one processor, cause the at least one processor to operate with one or more of the valves, the blower, the pressure transducer, the flow meter, any sensors, and/or the pump to perform operations of the filtration system. It should additionally be appreciated that certain embodiments of the FIG. 1 system can include at least one input device and/or at least one display device, and the one or more controller can be programmed or configured to operate with the at least at least one input device and/or at least one display device.

Figure 2:
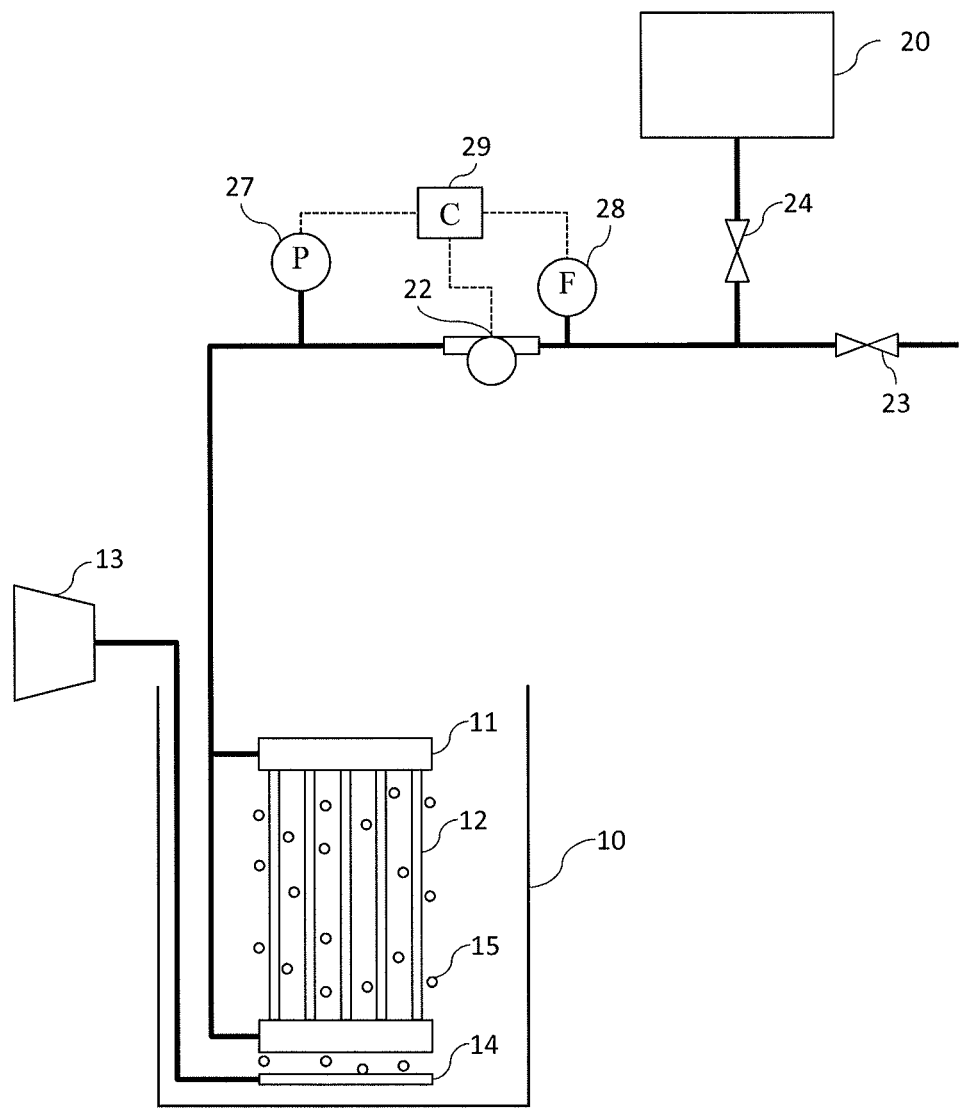
FIG. 2 is a schematic diagram illustrating an embodiment of a hollow fiber dead-end filtration system of the present disclosure having a reversible permeate flow and backwash pump.

FIG. 2 illustrates another non-limiting embodiment of a hollow-fiber dead-end filtration system of the present disclosure. The system of FIG. 2 includes many of the same components described above in connection with FIG. 1. Those components in FIG. 2 are marked with the same or similar element numbers as used in FIG. 1. The description of those elements including each of the alternatives discussed above in connection with FIGS. 1 and 2 apply in many respect to like element numbers in FIG. 2. Pump 22 in the system of FIG. 2 is a reversible pump that performs filtration or permeate flow as well as backwash flow. The system of FIG. 2, like the system of FIG. 1, includes a treatment tank 10 structured and arranged to receive and treat a liquid feed containing suspended solids (e.g., a biological slurry or algae slurry/feed received, for example, from an algae source or container that is in fluid communication with tank 10 via at least one conduit operating with an in-feed valve) to produce filtered permeate substantially free of suspended solids and a retentate with a suspended solids content higher than the liquid feed. A plurality of submerged hollow fiber membranes 12 are contained or held within treatment tank 10. In some embodiments, the submerged hollow fiber membranes 12 can be arranged into one or more module 11 that is contained in treatment tank 10. The one or more module 11 can also be arranged into one or more cassette. The hollow fiber membrane module 11 can include headers attached to each hollow fiber membrane 12 so as to create a watertight connection between the outside of the membranes 12 and a permeate channel of the header. The outer surface of the hollow fiber membranes 12 is in contact with the liquid feed and retentate.

To perform dead-end filtration, permeate is pumped or pulled through pores of the hollow fiber membranes so that the permeate is withdrawn through the inside of the lumens of the hollow fibers and retentate is produced outside the lumens of the hollow fibers (e.g., inside the permeate tank). A blower 13 can push air through at least one conduit and distributer 14 to create air bubbles 15 that are released below the hollow fibers to create fluid movement and movement of the hollow fibers, which aids in reducing fouling and improving backwash efficiency. The air bubbles can be released continuously, intermittently, or only during the backwash cycles.

During the filtration, permeate is withdrawn from the lumens of the hollow fiber membranes through at least one conduit via permeate pump 22, valve 24 is opened and valve 23 is closed intermittently to maintain the fluid level in permeate holding tank 20. A controller 29 (e.g., a programmable logic controller) controls permeate pump 22 based upon the permeate flow rate measured by flow meter 28 and the suction or negative pressure measured by the pressure transducer 27.

A backwashing sequence is initiated by opening valve 24, closing valve 23, and reversing the flow in pump 22 so that permeate can be withdrawn from permeate holding tank 20 (through the same at least one conduit as the conduit for filtration) and the retentate is pushed through the pores of the hollow fiber membranes into treatment tank 10. The flow rate of pump 22 is controlled by at least one controller 29 (e.g., a programmable logic controller) to maintain the desired backwash pressure as measured by pressure transducer 27. Once the backwash flow time is complete, withdrawal of permeate is resumed by reversing the flow in pump 22 so that the pump 22 is withdrawing permeate from the hollow fiber lumens through at least one conduit. It should be appreciated that in certain embodiments, multiple modules 11 can be connected in parallel in a cassette so that the entire cassette can be backwashed at the same time. Certain embodiments can also include multiple cassettes connected in parallel in a bank so that the multiple cassettes can be backwashed at the same time.

In one non-limiting embodiment of the system of FIG. 2, the backwash off-line period includes the time between stopping permeate flow from module 11 and restarting permeate flow from module 11. In various embodiments, the backwash off-line period includes one or more of: (i) the time to ramp pump 22 down and accelerate the pump in the opposite flow direction for backwash flow; (ii) the time to reach the backwash pressure; (iii) the time for the backwash flow; (iv) the time to ramp pump 22 down and accelerate the pump 22 in the opposite flow direction for permeate flow; and (v) the time to lower the pressure in the permeate lines to resume the permeate flow. In one particular non-limiting embodiment of the system of FIG. 2, the backwash off-line period includes the time for each of (i) to (v) above. The backwash interval in an embodiment includes the time between the start of one backwash cycle and the start of the next backwash cycle.

It should be appreciated that controller 29 in the system of FIG. 2 can in various embodiments include one or more controller, which can be programmed or configured to operate with one or more of the valves, the blower, the pressure transducer, the flow meter, the pump, any sensors and/or any other system components so as to perform various functions of the system including valving, pumping, backwashing, rinsing, filtration, permeate flow, chemical cleaning or any other system functions. In an embodiment, the one or more controller can include at least one processor and at least one memory device which stores instructions, which when executed by the at least one processor, cause the at least one processor to operate with one or more of the valves, the pressure transducer, the flow meter, any sensors, and the pump to perform operations of the filtration system. It should additionally be appreciated that certain embodiments of the FIG. 2 system can include at least one input device and/or at least one display device, and the one or more controller can be programmed or configured to operate with the at least at least one input device and/or at least one display device.

Figure 3:
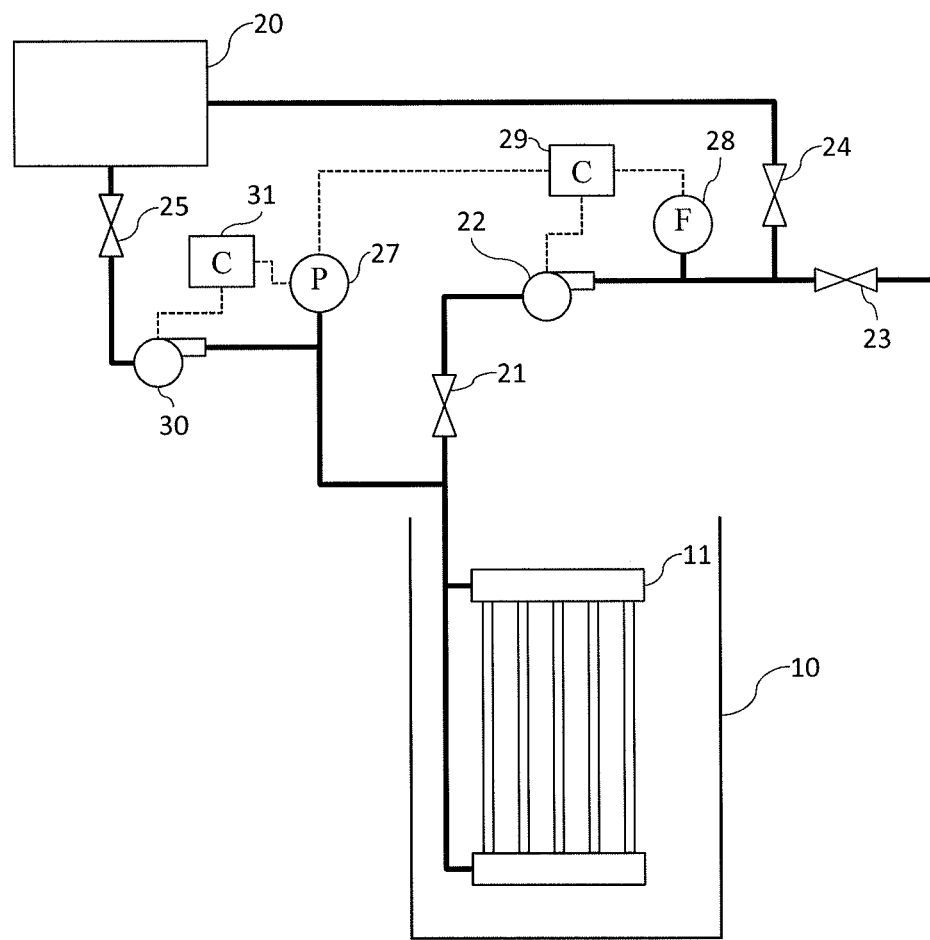
FIG. 3 is a schematic diagram illustrating a typical hollow fiber dead-end filtration system of the present disclosure having separate permeate and backwash pumps.

Referring now to FIG. 3, an additional non-limiting embodiment of a hollow-fiber dead-end filtration system of the present disclosure is illustrated in which separate permeate and backwash pumps are utilized. The system of FIG. 3 includes many of the same components described above in connection with FIGS. 1 and 2. Those components in FIG. 3 are marked with the same or similar element numbers as used in FIGS. 1 and 2. The description of those elements including each of the alternatives discussed above in connection with FIGS. 1 and 2 apply in many respects to like element numbers in FIG. 3. The system of FIG. 3 again includes a treatment tank 10 structured and arranged to receive and treat a liquid feed containing suspended solids (e.g., an algae feed received, for example, from an algae source or container that is in fluid communication with tank 10 via at least one conduit operating with an in-feed valve) to produce filtered permeate substantially free of suspended solids and retentate with a higher suspended solids content than the liquid feed. The treatment tank 10 contains submerged hollow fiber membranes 12 arranged into one or more module 11. In some embodiments, the one or more module 11 can also be arranged into one or more cassette. The one or more module 11 in an embodiment includes headers attached to the hollow fiber membranes 12 to create a watertight connection between the outside of the membranes 12 and a permeate channel of the header. The outer surface of the hollow fiber membranes 12 is in contact with the liquid feed and retentate.

To perform dead-end filtration, the permeate is pulled or pumped through pores of the hollow fiber membranes 12 so that the permeate is withdrawn through the inside of the lumens of the hollow fibers and retentate is produced outside the lumens of the hollow fibers (e.g., inside the treatment tank). During the filtration, valves 21 and 23 are open, valve 25 is closed, and permeate is withdrawn through at least one conduit by pump 22. Valve 24 is opened and valve 23 is closed intermittently to maintain the fluid level in the permeate holding tank 20. The permeate pump 22 is controlled by one or more controller 29 (e.g., a programmable logic controller) based upon the permeate flow rate measured by flow meter 28 and the suction pressure measured by the pressure transducer 27.

A backwash sequence is initiated by closing valve 21, stopping pump 22, opening valve 25 and starting pump 30 so that backwash or permeate fluid flows through at least one conduit to module 11. The flow rate of pump 30 is controlled by a controller 31 (e.g., a programmable logic controller) to maintain the desired backwash pressure as measured by pressure transducer 27. The flow rate of pump 30 can additionally or alternatively be controlled by the same controller that controls permeate pump 22. Once the backwash flow time is complete, withdrawal of permeate is resumed by stopping pump 30, closing valve 25, opening valve 21, and starting pump 22. It should be appreciated that in certain embodiments, multiple modules 11 can be connected in parallel in a cassette so that the entire cassette can be backwashed at the same time. Certain embodiments can also include multiple cassettes connected in parallel in a bank so that the multiple cassettes can be backwashed at the same time.

In an embodiment of the system of FIG. 3, the backwash off-line period includes the time between stopping permeate flow from module 11 and restarting permeate flow from module. In various embodiments, the backwash off-line period includes one or more of: (i) the time to open and close valves 21 and 25 for backwash flow; (ii) the time to ramp up pump 30; (iii) the time for the backwash flow; (iv) the time to ramp down pump 30, (v) the time open and close valves 21 and 25 to resume permeate flow for filtration; and (vi) the time to ramp up pump 22 to lower the pressure in the permeate lines to resume the permeate flow. In one particular non-limiting embodiment, the backwash off-line period for the system of FIG. 3 includes each of (i) to (vi) above. The backwash interval in an embodiment includes the time between the start of one backwash cycle and the start of the next backwash cycle.

It should be appreciated that controllers 29, 31 in the system of FIG. 3 can in various embodiments include one controller alone or multiple controllers including more than two controllers. Either the single controller or multiple controllers can be programmed or configured to operate with one or more of the valves, the pressure transducer, the flow meter, the pumps, any sensors and/or any other system components so as to perform various functions of the system including valving, pumping, backwashing, rinsing, permeate flow, chemical cleaning or any other system functions. In an embodiment, the one or more controller can include at least one processor and at least one memory device which stores instructions, which when executed by the at least one processor, cause the at least one processor to operate with one or more of the valves, the pressure transducer, the flow meter, any sensors, and pumps to perform system operations. It should additionally be appreciated that certain embodiments of the FIG. 3 system can include at least one input device and/or at least one display device, and the one or more controller can be programmed or configured to operate with the at least at least one input device and/or at least one display device.

Figure 4:
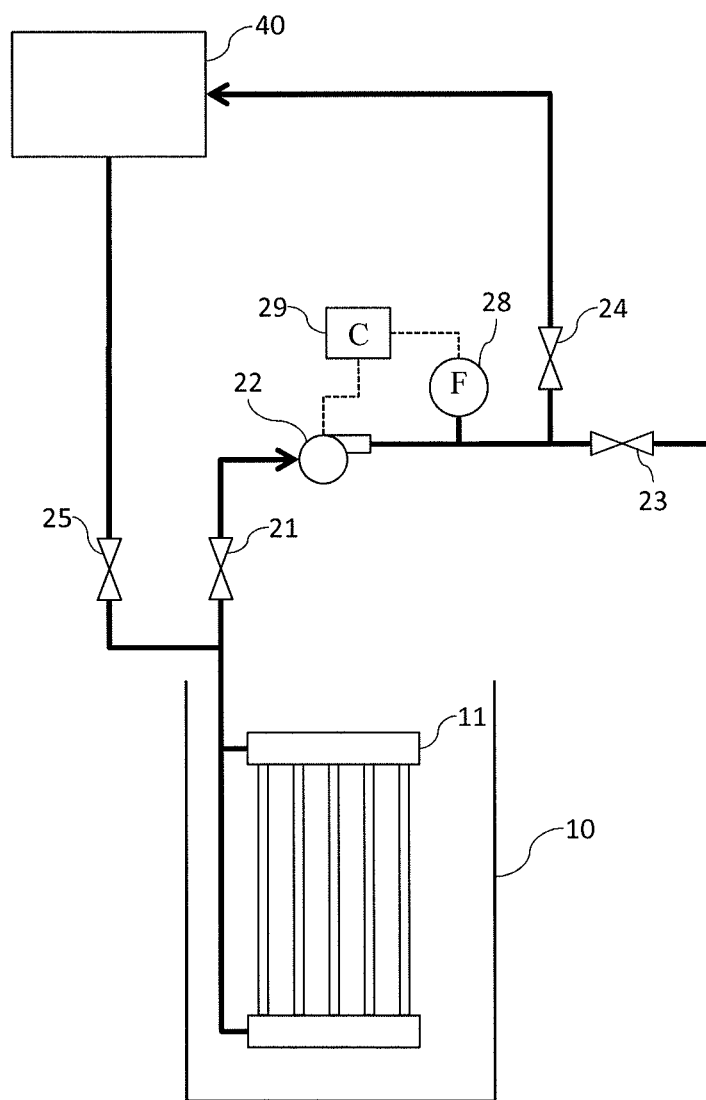
FIG. 4 is a schematic diagram illustrating an embodiment of a hollow fiber dead-end filtration system of the present disclosure having a permeate pump and a gravity fed backwash.

Referring to FIG. 4, another non-limiting hollow fiber membrane filtration system of the present disclosure is illustrated in which backwash is performed via gravity. The system of FIG. 4 also includes many of the same components described above in connection with FIGS. 1 to 3. Those components in FIG. 4 are marked with the same or similar element numbers as used in FIGS. 1 to 3. The description of those elements including each of the alternatives discussed above in connection with FIGS. 1 to 3 apply in many respects to like element numbers in FIG. 3. The system of FIG. 4, like the systems of FIGS. 1 to 3, includes a treatment tank 10 structured and arranged to receive and treat a liquid feed containing suspended solids (e.g., an algae feed received, for example, from an algae source or container that is in fluid communication with tank 10 via at least one conduit operating with an in-feed valve) to produce a filtered permeate substantially free of suspended solids and a retentate with a higher suspended solids content than the liquid feed. The treatment tank 10 contains submerged hollow fiber membranes 12 arranged into one or more module 11, which can be arranged into one or more cassette. In the illustrated embodiment, the submerged hollow fiber membranes 12 are arranged into a single module 11 that is contained in treatment tank 10. Then one or more module 11 can include headers attached to each hollow fiber membrane 12 to create a watertight connection between the outside of the membranes 12 and a permeate channel of the header. The outer surface of the hollow fiber membranes is in contact with the liquid feed and retentate.

To perform dead-end filtration, permeate is pumped or pulled through pores of the hollow fiber membranes so that the permeate is withdrawn through the inside of the lumens of the hollow fibers and a retentate is produced outside the lumens of the hollows fibers of the membrane. During the filtration, valves 21 and 23 are open, valve 25 is closed, and permeate is withdrawn through at least one conduit by pump 22. Valve 24 is opened and valve 23 is closed intermittently to maintain the fluid level in an elevated permeate gravity feed tank 40. At least one controller 29 (e.g., a programmable logic controller) controls permeate pump 22 based upon the permeate flow rate measured by flow meter 28.

A backwashing sequence is initiated by closing valve 21, stopping pump 22, and opening valve 25 so that backwash or permeate fluid can flow through at least one conduit to module 11. The backwash pressure is controlled by a difference in height between the permeate gravity feed tank 40 and the liquid level in treatment tank 10. Once the backwash flow time is complete, withdrawal of permeate is resumed by closing valve 25, opening valve 21, and starting pump 22. It should be appreciated that in certain embodiments, multiple modules 11 can be connected in parallel in a cassette so that the entire cassette can be backwashed at the same time. Certain embodiments can also include multiple cassettes connected in parallel in a bank so that the multiple cassettes can be backwashed at the same time.

In one non-limiting embodiment of the system of FIG. 4, the backwash off-line period includes the time between stopping permeate flow from module 11 and restarting permeate flow from module 11. In various embodiments, the backwash off-line period includes one or more of: (i) the time to open and close valves 21 and 25 to stop permeate flow from module 11 and to start backwash flow to module 11; (ii) the time for the backwash flow; (iii) the time open and close valves 21 and 25 to stop backwash flow and resume permeate flow for filtration; and (iv) the time to ramp up pump 22 to lower the pressure in the permeate lines to resume the permeate flow. In one particular non-limiting embodiment of the system of FIG. 4, the backwash off-line period includes the time for each of (i) to (iv) above. The backwash interval in an embodiment includes the time between the start of one backwash cycle and the start of the next backwash cycle.

It should be appreciated that controller 29 in the system of FIG. 4 can in various embodiments include one or more controller, which can be programmed or configured to operate with one or more of the valves, the flow meter, the pump, any sensors, and/or any other system components so as to perform various functions of the system including valving, pumping, backwashing, rinsing, filtration, permeate flow, chemical cleaning or any other system functions. In an embodiment, the one or more controller can include at least one processor and at least one memory device which stores instructions, which when executed by the at least one processor, cause the at least one processor to operate with one or more of the valves, the flow meter, any sensors, and the pump to perform operations of the filtration system. It should additionally be appreciated that certain embodiments of the FIG. 4 system can include at least one input device and/or at least one display device, and the one or more controller can be programmed or configured to operate with the at least at least one input device and/or at least one display device.

Figure 5:
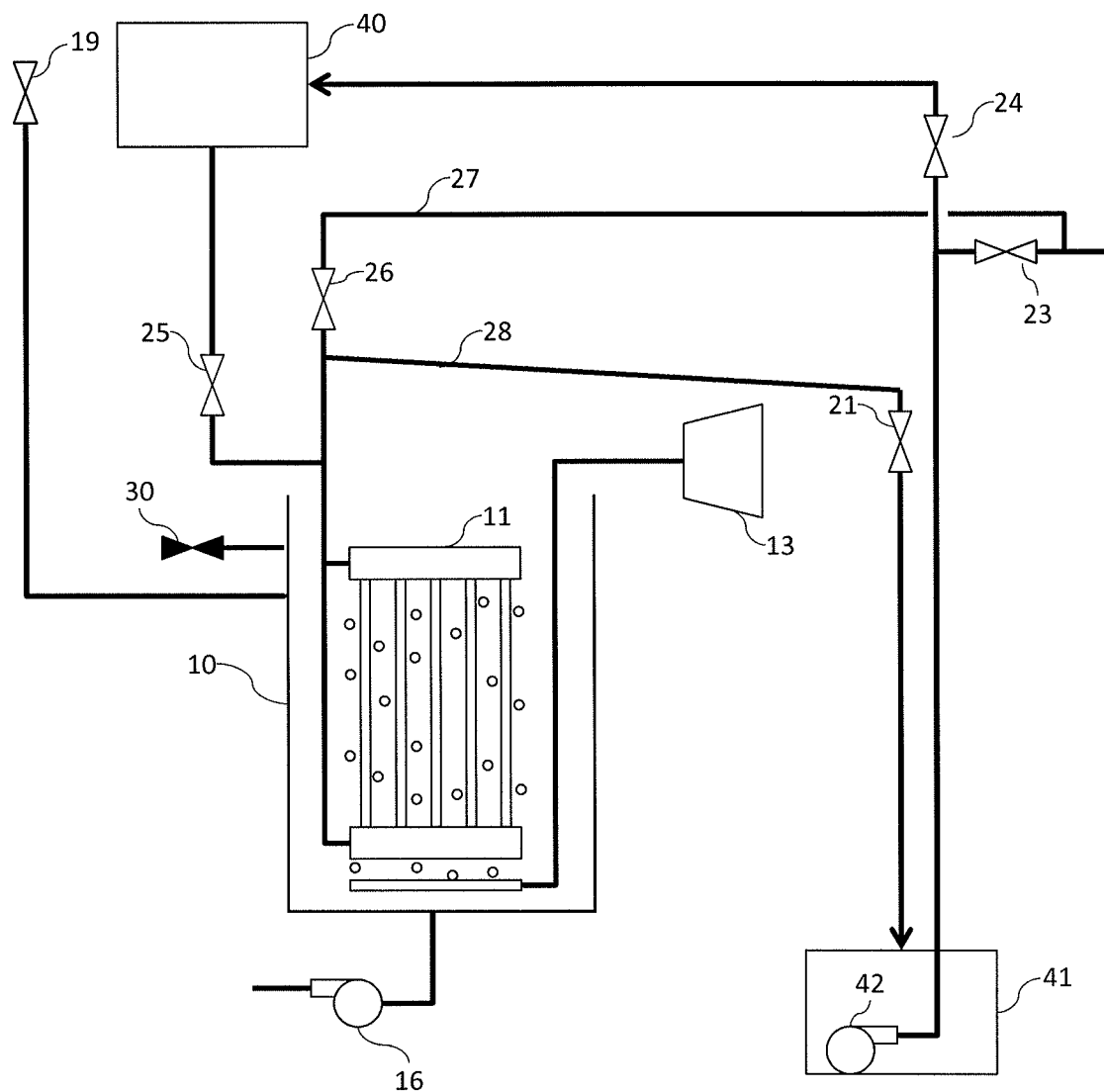
FIG. 5 is a schematic diagram illustrating an embodiment of a hollow fiber dead-end filtration system of the present disclosure having permeate siphoning and gravity fed backwash.

Referring to FIG. 5, another non-limiting embodiment of a hollow fiber filtration system is illustrated in which backwash is performed via gravity and siphoning or a siphoning system is used to pull the permeate for filtration. Pumps are typically used in hollow fiber membrane filtration systems to reduce pressure in the permeate lines so that the permeate inside the lines can be pulled through the hollow-fibers of the membranes. Gravity driven siphon systems according to the present disclosure (e.g., FIGS. 5, 6 and 7) eliminate the need for such a pump and instead pull permeate via siphoning through hollow fiber membranes in a dead-end filtration operation. That is, the siphoning feature or systems of the present disclosure utilize the fact that pressure lower than atmospheric pressure allows fluid to be pulled through the hollow fiber membranes. One problem with siphoning systems, however, is that air can enter the system in various ways. For example, air can enter from leaks, from air bubbles being pulled through the hollow-fiber membrane to reduce fouling, or from dissolution of air in the permeate system as a result of the permeate being saturated at atmospheric pressure and the pressure in the siphon lines being less than atmospheric pressure. The effectiveness of siphoning or siphon systems can be reduced by air accumulation in the siphon lines. The diameter of the siphon lines can therefore be selected so that flux is high enough to pull the air through the line. Alternatively, a high point located in the siphon line can be used to collect the air and a vacuum pump can be used to remove the air. An additional pump and gas level monitoring and vacuum pump controls can be necessary with this approach to ensure that permeate does not enter the vacuum pump.

The system of FIG. 5 includes many of the same components described above in connection with FIGS. 1 to 4. Those components in FIG. 5 are marked with the same or similar element numbers as used in FIGS. 1 to 4. The description of those elements including each of the alternatives discussed above in connection with FIGS. 1 to 4 apply in many respects to like element numbers in FIG. 5. The system of FIG. 5, like the systems of FIGS. 1 to 4, includes a treatment tank 10 structured and arranged to receive and treat a liquid feed containing suspended solids (e.g., an algae feed received, for example, from an algae source or container that is in fluid communication with tank 10 via at least one conduit operating with an in-feed valve 19) to produce a filtered permeate substantially free of suspended solids and a retentate with a higher suspended solids content than the liquid feed. Treatment tank 10 contains submerged hollow fiber membranes 12 arranged into one or more modules 11, which can be arranged into one or more cassette. In the illustrated embodiment, the submerged hollow fiber membranes 12 are arranged into a single module that is contained in treatment tank 10. The one or more modules 11 can include headers attached to each hollow fiber membrane 12 so as to create a watertight connection between the outside of the membranes 12 and a permeate channel of the header. The outer surface of the hollow fiber membranes is in contact with the liquid feed and retentate.

To perform dead-end filtration, permeate is withdrawn or pulled through pores of the hollow fiber membranes so that the permeate is withdrawn through the inside of the lumens of the hollow fibers and a retentate is produced outside the lumens of the hollow fibers. The liquid level in treatment tank 10 is controlled by intermittent opening of the feed valve 19. During the filtration, valves 21 and 23 are open, valves 25 and 26 are closed, and permeate is pulled or withdrawn by siphon through at least one permeate or siphon conduit 28 into the permeate siphon tank 41. The suction pressure of the siphon is controlled by the difference in height between the liquid in treatment tank 10 and permeate level in permeate siphon tank 41. Pump 42 can be operated intermittently to maintain the level in siphon tank 41. Valve 24 can be opened and valve 23 can be closed intermittently to maintain the fluid level in elevated permeate gravity feed tank 40. It should be appreciated that in various embodiments, the suction, pulling or siphon process of permeate withdrawal can begin, for example, by bleeding air from the fluid conduit or line on which valve 21 operates (e.g., conduit 28) and/or by adding a liquid such as water into that same conduit. Likewise, in each of the embodiments described herein which permeate withdrawal occurs via siphoning, the process of permeate withdrawal can being, for example, via bleeding air from the lines or conduits in which one or more of valves 25 operate (e.g., valves 25a, 25b, or 25c discussed below) and/or by adding a liquid such as water into the same lines or conduits. It should additionally be appreciated that at least one liquid level sensor can be included in tank 10 to sense and control the level of liquid in treatment tank 10.

A backwash sequence in the system of FIG. 5 can be initiated by (i) closing valve 21 and opening valve 25 so that backwash or permeate fluid can flow through at least one conduit to module 11, and (ii) controlling the backwash pressure by a difference in height between the permeate gravity feed tank 40 and the liquid level in treatment tank 10. A purge valve 26 can be coupled to a purge conduit 27 at a high point in the permeate or siphon conduit 28 where gas can accumulate. During the backwash sequence, a purge valve 26 can be opened to purge any gas that has accumulated in the siphon or permeate conduit 28. Gas discharge line or conduit 27 is much smaller in diameter than permeate or siphon line 28, so that when purge valve 26 is opened there is only a small reduction in backwash flow while the gas is being purged. Purge valve 26 is closed before or when the backwash flow time is complete. Once the backwash flow time is complete, withdrawal of permeate is resumed closing valves 25 and 26 and opening valve 21. It should be appreciated that multiple purge conduits 27 and valves 26 could be utilized instead of a single purge conduit. It should also be appreciated that one or more purge conduits can be coupled to the at least one permeate conduits in any of the multi-stage harvesting systems described herein.

In one non-limiting embodiment of the system of FIG. 5, the backwash off-line period includes the time between stopping permeate flow from module 11 and restarting permeate flow from module 11. In various embodiments, the backwash off-line period includes one or more of: (i) the time to open and close valves 21 and 25 to stop permeate flow from module 11 and to start backwash flow to module 11; (ii) the time for the backwash flow; and (iii) the time to open and close valves 21 and 25 to stop backwash flow and resume permeate flow for filtration. In one particular non-limiting embodiment of the system of FIG. 5, the backwash off-line period includes the time for each of (i) to (iii) above. The backwash interval in an embodiment includes the time between the start of one backwash cycle and the start of the next backwash cycle. It should be appreciated that in certain embodiments, multiple modules 11 can connected in parallel in a cassette so that the entire cassette can be backwashed at the same time. Certain embodiments can also include multiple cassettes connected in parallel in a bank so that the multiple cassettes can be backwashed at the same time.

In an alternative non-limiting embodiment, once a desired or predetermined suspended concentration level has been attained, treatment tank 10 can be emptied, and optionally rinsed. To empty the tank, filtration can be stopped by closing valves 25, 21 and 19. The treatment tank 10 can then be emptied via operation of pump 16. After treatment tank 10 is emptied, a rinse can optionally be performed prior to restarting the filtration process for tank 10. To perform a rinse, treatment tank 10 is filled with water or a suitable cleaning solution, and cleaning valve 30 is opened so that water or a cleaning solution can be added to tank 10 (e.g., water or cleaning solution held in a rinsing solution source or container flowing through a conduit coupled to the source and to tank 10). Once treatment tank 10 is filled and optionally mixed via air bubbles from air supplied via blower 13, the rinse water or cleaning solution can be removed from treatment tank 10 via operation of pump 16. In some embodiments, the water used for the rinse can also contain cleaning chemicals to aid in rinsing the tank or cleaning the membranes. The water or solution can be emptied from treatment tank through one or more outlet or conduit via operation of pump 16 (and opening a valve on the conduit in some embodiments), after which valve 19 can be opened so as to refill treatment tank 10 with in-feed and the system can utilize valves 25 and 21 to perform filtration and backwash with no retentate discharge until the desired solid concentration level is attained again. This cycle of emptying the retentate and optionally rinsing the treatment tank 10 can be repeated one or more times. It should be appreciated that in an embodiment, one or more algae concentration sensor can again be utilized to determine when the desired solid algae concentration has been reached. Such one or more sensor can be located, for example, in treatment tank 10 or in any other suitable location. Alternatively or additionally, the system can be configured to determine the solid concentration level attainment based upon volumetric control, which can utilize, for example, a flow meter or any known flow and/or volumetric parameters.

In another non-limiting embodiment, once the desired or predetermined suspended concentration level has been attained, feed valve 19 can be closed and the liquid level in treatment tank 10 can be controlled by intermittent opening of valve 30 to add water or any other suitable replacement solution to replace the original media of the algae slurry. The water or replacement solution entering treatment tank 10 dilutes the original media and eventually replaces at least most of the media. The media replacement level can be monitored, sensed or determined by any suitable sensor or sensing methods such as (i) sensing or determining the difference in conductivity, pH, ion specific electrode, or specific gravity of the algae slurry retentate or permeate relative to the initial value of the of the in the algae slurry retentate or permeate, or (ii) sensing or determining the level of media replacement through total volumetric throughput of rinse water or solution, measured, for example, by a rinse feed flow meter or permeate flow meter, relative to the total volume of treatment tank 10. Once the desired or predetermined media replacement level has been reached, then the rinsed algae slurry retentate can be removed from treatment tank 10 through an outlet or conduit via operation of pump 16 (and in some embodiments via operation of a valve on the conduit with which pump 16 operates).

It should be appreciated that the system of FIG. 5 can in various embodiments include one or more controller, which can be programmed or configured to operate with one or more of the valves, the pump, any sensors and/or any other system components so as to perform various functions of the system including valving, pumping, backwashing, rinsing, filtration, permeate flow, chemical cleaning or any other system functions. In an embodiment, the one or more controller can include at least one processor and at least one memory device which stores instructions, which when executed by the at least one processor, cause the at least one processor to operate with one or more of the valves, the pump, and sensors or any other components to perform operations of the filtration system. It should additionally be appreciated that certain embodiments of the FIG. 5 system can include at least one input device and/or at least one display device, and the one or more controller can be programmed or configured to operate with the at least at least one input device and/or at least one display device.

As mentioned above, each of the filtration systems illustrated in the embodiments of FIGS. 1 to 5 can be arranged into groups such that modules, cassettes consisting of multiple modules, or banks of cassettes can be backwashed simultaneously and/or sequentially. In addition, in certain embodiments of the systems illustrated in FIGS. 1 and 2, a separate backwash/permeate system can be utilized for each group of modules (e.g., each cassette or banks of cassettes), while in certain embodiments of the systems illustrated in FIGS. 3 to 5, the groups can be individually isolated for backwash or permeate flow via valves and valving functions. In some embodiments of the present disclosure, a separate backwash and permeate system is not required for each group. If the groups are backwashed sequentially, then permeate and backwash pumps can be operated continuously while certain embodiments of the present systems step through the different groups. In other embodiments, the backwashing can be assisted via one or more of chemical addition, air addition, mechanical pulses, ultrasonic waves, and any other suitable methods that help remove fouling material. The hollow fiber membrane modules can alternatively or additionally be rinsed or chemically cleaned periodically to remove fouling material that was not removed during backwashing. Each of the systems of the present disclosure that are arranged into groups such as modules, cassettes and banks of cassettes can likewise be controlled via one or more controller as discussed above.

Figure 6:
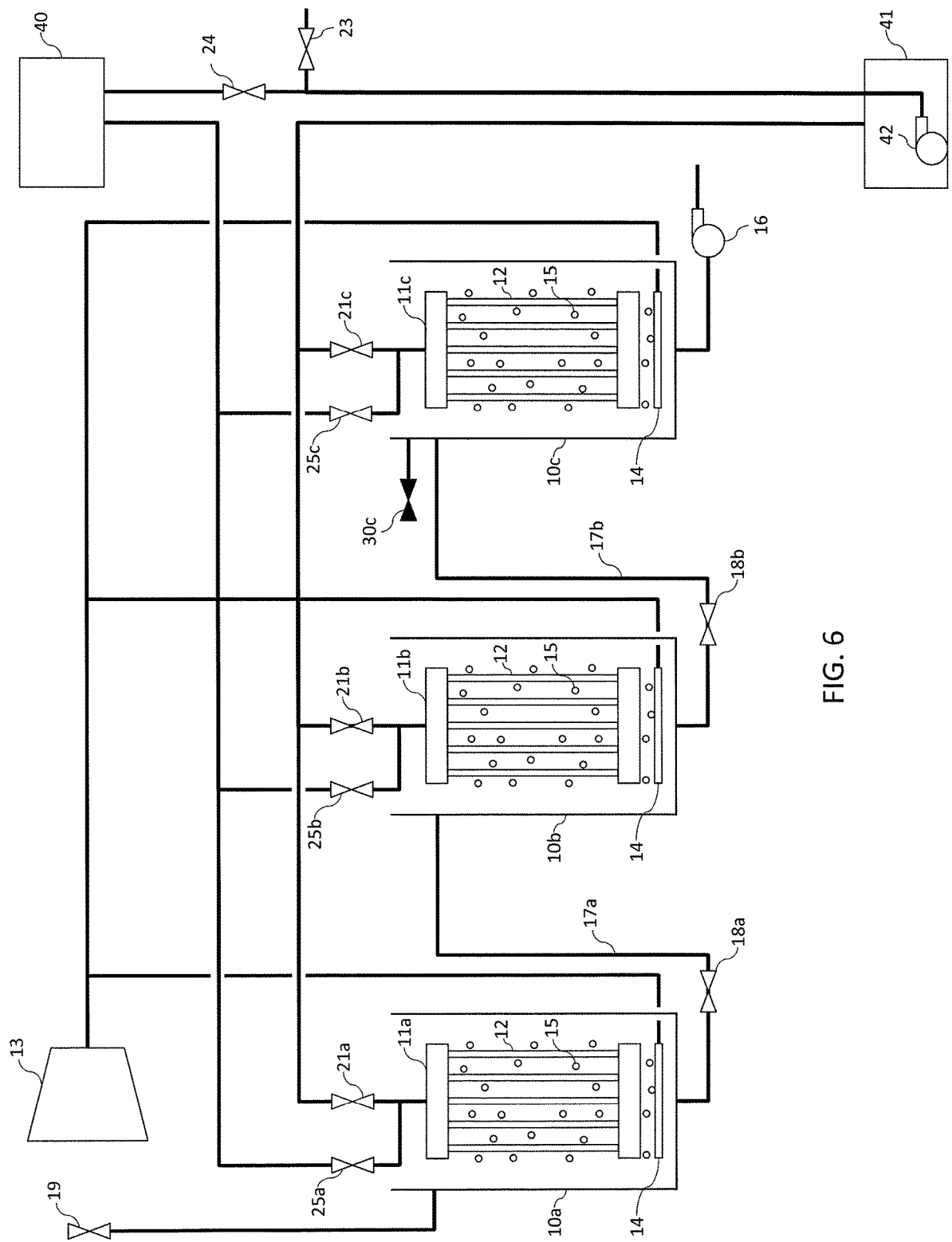
FIG. 6 is a schematic diagram illustrating an embodiment of a multistage hollow fiber dead-end filtration system of the present disclosure having gravity backwash and permeate siphoning.

Referring now to FIG. 6, another non-limiting embodiment of a membrane filtration system of the present disclosure is illustrated in which three separate treatment tanks 10a, 10b and 10c (referred to collectively as treatment tanks 10) are arranged so as to define multiple stages that are connected in series by conduits 17. The multistage filtration system of FIG. 6 includes some of the same components described above in connection with FIGS. 1 to 5. Those components in FIG. 6 are marked with the same or similar element numbers as used in FIGS. 1 to 5. The description of those elements including each of the alternatives discussed above in connection with FIGS. 1 to 5 apply in many respects to like element numbers in FIG. 6.

The treatment tanks 10 in the system of FIG. 6, similar to the tanks 10 for the systems of FIGS. 1 to 5, are structured and arranged for treating a liquid feed containing suspended solids to produce a filtered permeate substantially free of suspended solids and a retentate with a higher suspended solids content than the liquid feed. Each of the treatment tanks 10, which can define separate stages of the multistage system, contain submerged hollow fiber membranes 12 arranged into one or more module 11. The one or more module 11 can be arranged into cassettes. Each one or more module 11 can be contained in a respective one of the treatment tanks 10. The one or more modules 11 can include headers attached to each hollow fiber membrane 12 to create a watertight connection between the outside of the membranes 12 and a permeate channel in the header. The outer surface of the hollow fiber membranes 12 is in contact with the liquid feed and retentate. It should be appreciated that in certain embodiments, instead of having multiple separate treatment tanks defining each stage of the multistage system, a single treatment tank includes, for example, dividers in the tank which separate and define each of the multiple stages of the multistage filtration system.

To perform dead-end filtration in the multistage system of FIG. 6, the permeate is pumped or pulled through pores of the hollow fiber membranes in each stage of the system so that the permeate is withdrawn through the inside of the lumens of the hollow fiber membranes in each stage and a retentate is produced outside the lumens of the hollow fiber membranes in each stage. A blower 13 can be utilized to push air through at least one conduit to distributer 14 to create air bubbles 15 that are released below the hollow fibers to create fluid movement and movement of the hollow fibers, which aids in reducing fouling and improving backwash efficiency. The air bubbles can be released continuously, intermittently, or only during the backwash cycles.

During filtration, the liquid feed enters treatment tank 10a (e.g., the first filtration stage) through at least one conduit and/or inlet via operation of valve 19 (e.g., receiving fluid from an algae source or container). Permeate is withdrawn from treatment tank 10a through an outlet, through valve 21a and through a conduit into permeate siphon tank 41. The retentate in treatment tank 10a travels through an outlet of tank 10a, through valve 18a, and through conduit 17a to an inlet of treatment tank 10b (e.g., the second filtration stage). Permeate is withdrawn from treatment tank 10b through an outlet, through valve 21b, through a conduit and into permeate siphon tank 41. The retentate in treatment tank 10b travels through an outlet in tank 10b, through valve 18b, through conduit 17b to treatment tank 10c (e.g., the third filtration stage). Permeate is withdrawn from treatment tank 10c through an outlet of tank 10c, through valve 21c through a conduit into the permeate siphon tank 41. The retentate in treatment tank 10c is withdrawn through a conduit via pump 16 (which conduit can include a valve operating with the conduit to allow or disallow the retentate to be withdrawn). The liquid level in treatment tank 10a is controlled by intermittent opening of the feed valve 19. The liquid level in treatment tanks 10b and 10c is maintained by gravity at the same level as treatment tank 10a, less the pressure drop to move through conduits 17a and 17b. It should be appreciated that the permeate withdrawn from each of treatment tank 10a, 10b, 10c can flow through a common conduit or permeate line to the permeate or permeate siphon tank 41.

During filtration, valves 21a, 21b, 21c (referred to collectively as valves 21) and 23 are open, valves 25a, 25b, 25c (referred to collectively as valves 25) are closed, and permeate is pulled or withdrawn into the permeate siphon tank 41 through at least one conduit. The suction or negative pressure is controlled by the height difference between the liquid in each of treatment tanks 10 and the permeate level in permeate siphon tank 41. In an embodiment, tank 10a can include a level sensor which can be used to sense or control the level of fluid for tank 10a. Pump 42 is operated intermittently to maintain the level in siphon tank 41. Valve 24 is opened and valve 23 is closed intermittently to maintain the fluid level in the elevated permeate gravity feed tank 40.

Each stage or tank in the system of FIG. 6 can be backwashed separately from each of the other stages or at the same time as any of the other stages. A backwash sequence can be initiated for each stage in the same manner, namely by closing valve 21 for that respective stage, and opening valve 25 for that respective stage. The backwash pressure is controlled by the difference in height of the permeate gravity feed tank 40 and the liquid level in whichever treatment tank 10a, 10b and/or 10c is being backwashed. Once the backwash flow time is complete, withdrawal of permeate is resumed by closing respective valve(s) 25 and opening respective valve(s) 21, depending upon which stages are being backwashed.

In one non-limiting example of the system of FIG. 6, the backwash off-line period includes the time between stopping permeate flow from at least one of the modules 11 and restarting permeate flow from at least one of the modules 11. In various embodiments, the backwash off-line period includes one or more of: (i) the time to open and close valves 21 and 25 to stop permeate flow from module 11 and to start backwash flow to module 11; (ii) the time for the backwash flow; and (iii) the time to open and close valves 21 and 25 to stop backwash flow and resume permeate flow for filtration. In one particular non-limiting embodiment of the system of FIG. 6, the backwash off-line period includes the time for each of (i) to (iii) above. The backwash interval in an embodiment is the time between the start of one backwash cycle and the start of the next backwash cycle. It should be appreciated that the backwash off-line period and interval for the multistage systems and methods illustrated by FIG. 6 can be (a) an interval or period for one stage or tank of the plurality of tanks or stages in the system, or (b) an interval or period for multiple (including all or less than all) the stages or tanks of the plurality of stages or tanks.

It should be appreciated that in certain embodiments of FIG. 6: (i) different backwash intervals and/or periods can be utilized for each treatment tank or stage (e.g., one or more earlier stages have a longer period while one or more later stages have a shorter period, or one or earlier stages have a longer interval, while one or more later stages have a shorter interval), (ii) the hollow fiber membrane area in each treatment tank or stage can be different (e.g., one or more earlier stages have a higher area while one or more later stages have a lower area), and (iii) the permeate withdrawal rate of each treatment tank or stage can be allowed to vary. It should also be appreciated that the suspended solids content of the retentate in FIG. 6 is higher inside treatment tank 10b then it is in treatment tank 10a, and higher in treatment tank 10c then it is in treatment tank 10b, and that the suspended solids content in each tank 10a, 10b, 10c will reach a natural equilibrium based upon the in-feed rate, the permeate withdrawal rate from each treatment tank, and the retentate discharge rate due to the operation of pump 16.

It should be appreciated the multistage filtration system of FIG. 6 can operate at substantially the same maximum pressure drop or negative pressure at each stage (e.g., at each treatment tank 10a, 10b, 10c). In other words, the negative pressure used to pull permeate through the pores of the hollow fiber membranes 12 positioned in tank 10a can be substantially the same negative pressure that is used to pull permeate through the pores of the hollow fiber membranes 12 positioned in each of tanks 10b and 10c. It should be appreciated that the maximum pressure drop or negative pressure can be based upon physical limitations of the hollow fiber membranes, and that the flux can be lower in each successive stage in FIG. 6 (e.g., each successive treatment tank 10a, 10b, and 10c) due to the concentration of solid algae (due to the retentate produced) in each stage being higher while the pressure drop in each stage remains the same. The backwash period and intervals for each stage or treatment tank can be adjusted independently to provide the highest net flux in each stage based upon, for example, the concentration level in that stage and/or the fouling characteristics of the algae. For example, in one embodiment, the system is configured to automatically alter at least one of the backwash period or interval for one or more of the multiple stages based upon one or more solid algae concentration reading from at least one concentration sensor. The one or more algae concentration sensors can be located, for example, in treatment tanks 10a, 10b or 10c, or in any other suitable location. Alternatively or additionally, the system can be configured to determine the concentration attainment level based upon volumetric control, which can employ, for example a flow meter or any suitable flow and volumetric parameters. In other embodiments, the system is initially programmed or configured so that least one of the backwash period or interval of at least one of the stages is different from at least one of the other stages based upon known fouling characters of the algae in the algae slurry or in-feed.

In certain embodiments, when the system of FIG. 6 is first started or initiated, the system operates such that no retentate discharge occurs until a desired or predetermined suspended solids concentration level has been attained. In an embodiment, one or more algae concentration sensor can be utilized to determine when the predetermined or desired suspended concentration has been reached. Such one or more sensor be located, for example, in treatment tanks 10a, 10b or 10c, or in any other suitable location. Alternatively or additionally, the system can determine concentration by utilizing a flow meter and/or volumetric flow rate data, feed concentration data, and the tank volume.

In one non-limiting embodiment, once the desired or predetermined suspended concentration level has been attained, the system is configured to gradually withdraw retentate or material (e.g., concentrated algae slurry) from treatment tank 10c via operation of pump 16 (e.g., a conduit and valve operating with pump 16 and coupled to tank 10).

In an alternative non-limiting embodiment, once the desired or predetermined suspended concentration level has been attained, treatment tank 10c can be emptied, and optionally rinsed. To empty the tank, filtration is stopped by closing valves 25c, 21c, and 18b. The treatment tank 10c is then emptied via operation of pump 16 (e.g., a conduit and valve operating with pump 16 and coupled to tank 10). After tank 10c is emptied, a rinse can optionally be performed prior to restarting the filtration of tank 10c. To perform a rinse, treatment tank 10c is filled with water or cleaning solution, and cleaning valve 30c is opened so that water or solution can be added to tank 10c through valve 30c (e.g., the water or solution can come from a rinse source coupled fluidly with tank 10c via a conduit and valve 30c coupled to conduit 30c). Once the tank 10c is filled and optionally mixed via air bubbles from blower 13, the rinse water or cleaning solution can be removed through an outlet or conduit via operation of pump 16 (e.g., opening a valve on a conduit or outlet and operating pump 16). In some embodiments, the water used for the rinse can also contain cleaning chemicals to aid in rinsing the tank or cleaning the membranes. After the water has been emptied from tank 10c via operation of pump 16, valve 18b can be opened to refill tank 10c, and the system can be operated using valves 25c and 21c for filtration and backwash with no retentate discharge until the desired solids concentration level is attained again. This cycle of emptying the retentate and optionally rinsing the treatment tank 10c can be repeated one or more times. In an embodiment, one or more algae concentration sensor can again be utilized to determine when the desired concentration has been reached. Such one or more sensor be located, for example, in treatment tanks 10a, 10b or 10c, or in any other suitable location. Alternatively or additionally, the system can be configured to determine the concentration level attainment based upon volumetric control, which can utilize, for example, a flow meter or any known flow and/or volumetric parameters.

In another alternative non-limiting embodiment, once the desired or predetermined suspended concentration level has been attained, feed valve 18b can be closed and the liquid level in treatment tank 10c can be controlled by intermittent opening of feed valve 30c to add water or any other suitable replacement solution to replace the original media of the algae slurry (e.g., opening valve 30c coupled to a conduit or inlet, which conduit is also coupled to the water or solution source such as a container). The water or replacement solution entering treatment tank 10c dilutes the original media and eventually replaces at least most of the media. The media replacement level can be determined, monitored or sensed by any suitable sensor or sensing methods such as (i) sensing or determining the difference in conductivity, pH, ion specific electrode, or specific gravity of the algae slurry retentate or permeate relative to the initial value of the of the in the algae slurry retentate or permeate, or (ii) sensing or determining the level of media replacement through total volumetric throughput of rinse water or solution, measured, for example, by a rinse feed flow meter or permeate flow meter, relative to the total volume of treatment tank 10c. Once the desired or predetermined media replacement level has been reached, then the rinsed algae slurry retentate can be removed from treatment tank 10c through an outlet or conduit via operation of pump 16 (e.g., opening a valve coupled to the outlet or conduit and operating pump 16).

Like the embodiments of FIGS. 1 to 5, the system of FIG. 6 can include one or more controller, which can be programmed or configured to operate with one or more of the valves, the blower, one or more of the pumps, any sensors, any flow meters, and/or any other system components so as to perform various functions of the system including valving, pumping, backwashing, rinsing, filtration, permeate flow, or any other system functions. In an embodiment, the one or more controller can include at least one processor and at least one memory device which stores instructions, which when executed by the at least one processor, cause the at least one processor to operate with one or more of the valves, the pumps, any sensors and any other components to perform operations of the filtration system. Various embodiments of the FIG. 6 system can also include at least one input device and/or at least one display device, and the one or more controller can be programmed or configured to operate with the at least at least one input device and/or at least one display device.

Figure 7:
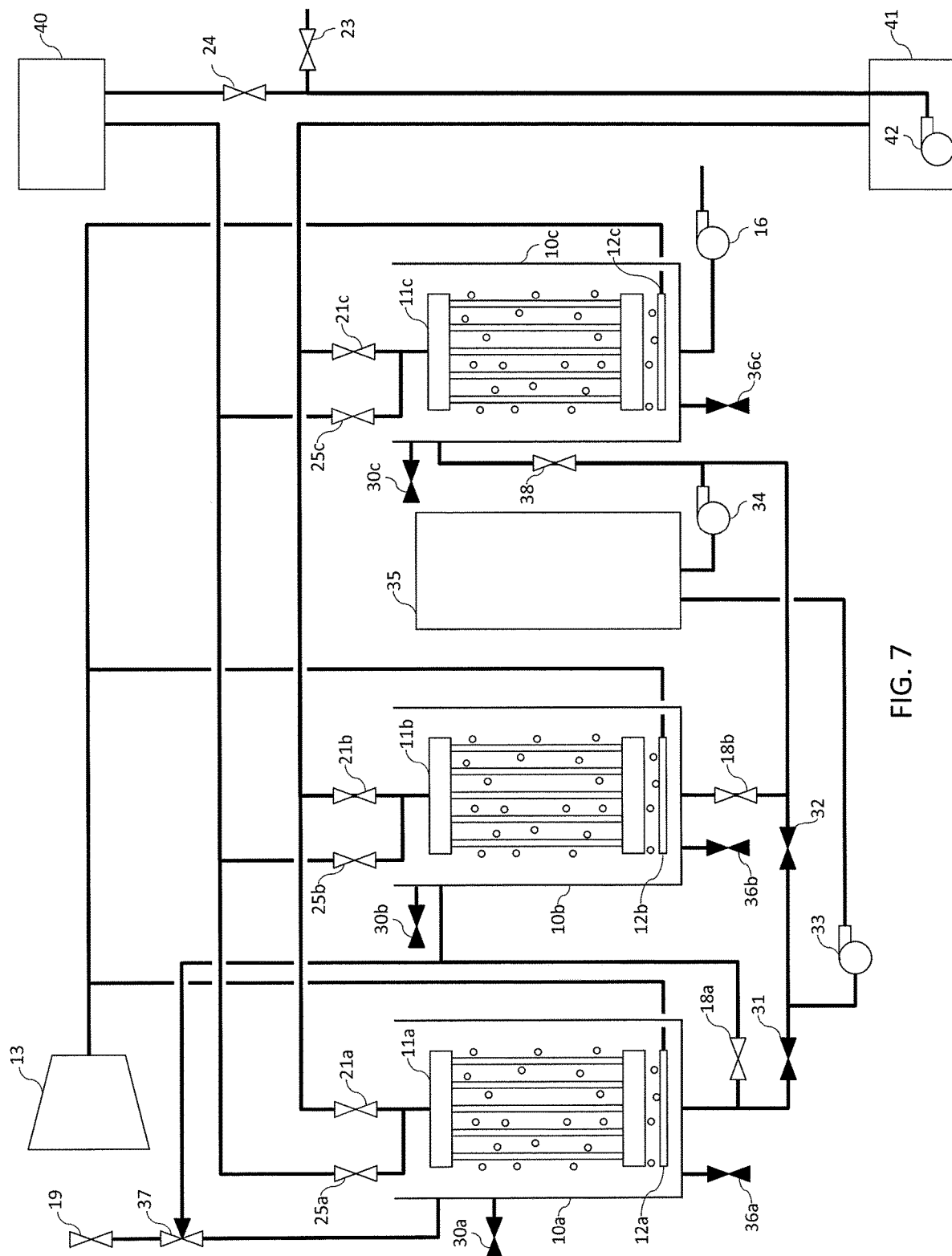
FIG. 7 is a schematic diagram illustrating an embodiment of a multistage hollow fiber dead-end filtration system of the present disclosure having gravity backwash, permeate siphoning, and a transfer tank.

FIG. 7 illustrates another embodiment of a multistage hollow fiber dead-end filtration system of the present disclosure in which the system includes a transfer tank that enables cleaning or isolation of one of the multiple stages or tanks while maintaining filtration or flow through the other stages or tanks. That is, the system of FIG. 7 illustrates a multistage hollow fiber dead-end filtration system for isolating individual treatment tanks or stages so that the isolated stage or tank, including its hollow fiber membranes, can be cleaned or rinsed while the other treatment tanks or stages remain on-line or in filtration mode.

The system of FIG. 7 operates in substantially the same manner as described above for FIG. 6 during filtration and backwashing with valves 31, 32, 36a, 36b, and 36c closed; pumps 33 and 34 off; and three-way valve 37 closed to treatment tank 10b. The system of FIG. 7 also includes many of the same components described above in connection with FIGS. 1 to 6. Those components in FIG. 6 are marked with the same or similar element numbers as used in FIGS. 1 to 6. The description of those elements including each of the alternatives discussed above in connection with FIGS. 1 to 6 apply in many respects to like element numbers in FIG. 7. In addition to the liquid level sensor in tank 10a, like the above embodiments, a liquid level sensor can also be included in each of tanks 10b and 10c (for the system of FIGS. 6 and 7). The system can utilize each sensor when a respective treatment tank 10a, 10b, or 10c receives in-feed so as to sense and control the level of liquid in the respective tank.

Turning now to the isolation and cleaning aspects of the system of FIG. 7, to clean treatment tank 10a while treatment tanks 10b and 10c remain in dead-end filtration or on-line, the system of FIG. 7 operates according to the following sequence: close valves 18a and 21a, turn three-way valve 37 from treatment tank 10a to treatment tank 10b; open valve 31 and utilize pump 33 to transfer retentate from treatment tank 10a to a transfer tank 35 through at least one conduit; close valve 31 and add water with or without cleaning chemicals to treatment tank 10a through at least one inlet or conduit via operation of valve 30a (e.g., opening valve 30a and allowing fluid to flow from a source or container through a conduit to tank 10a); soak the membrane in treatment tank 10a for a desired or predetermined cleaning time with continuous, intermittent, or no air bubbling through diffuser 12a; drain treatment tank 10a through an outlet or conduit via operation of valve 36a; close valve 36a, turn three-way valve 37 from treatment tank 10b to treatment tank 10a to fill treatment tank 10a with liquid feed through a conduit via operation of valve 19; and open valve 18a and valve 21a to resume normal or filtration operation in which all three tanks 10a, 10b, and 10c are on-line. While treatment tank 10a is off-line, transfer tank 35 is processed to control the level in treatment tank 10b by allowing fluid to flow from treatment tank 10b through a conduit or outlet via operation of pump 34, and control the level in treatment tank 10c through operation of valve 38. Once transfer tank 35 is emptied, the level in treatment tank 10b is controlled through intermittent operation of valve 19, and three-way valve 37 is opened for normal operation of treatment tank 10b.

To clean treatment tank 10b while treatment tanks 10a and 10c remain in dead-end filtration or on-line, the system of FIG. 7 performs the following sequence: close valves 18a and 21b; close valve 37, open valve 32 and utilize pump 33 to transfer the retentate from treatment tank 10b to transfer tank 35 through at least one conduit; close valve 18b and add water with cleaning chemicals through to treatment tank 10b through operation of valve 30b (e.g., opening valve 30b and allowing fluid to flow from a source or container through a conduit to tank 10b); soak the membrane in treatment tank 10b for a predetermined or desired cleaning time with continuous, intermittent, or no air bubbling through diffuser 12b; drain treatment tank 10b through valve 36b; close valve 36b; open valve 18a and 21b, and close valves 31 and 32 to resume normal operation. While treatment tank 10b is off-line or being cleaned or rinsed, treatment tank 35 is processed by controlling the level in treatment tank 10c through operation of pump 34 with valve 38 open and valve 32 closed. Once transfer tank 35 is emptied, valves 31, 32 and 37 are opened for normal operation of treatment tank 10c.

It should be appreciated that like the system of FIG. 6, the multistage filtration system of FIG. 7 can operate at substantially the same maximum pressure drop or negative pressure at each stage (e.g., at each treatment tank 10a, 10b, 10C). In other words, the negative pressure used to pull permeate through the pores of the hollow fiber membranes 12 positioned in tank 10a can be substantially the same negative pressure used to pull permeate through the pores of the hollow fiber membranes 12 positioned in each of tanks 10b and 10c. It should be appreciated that the maximum pressure drop or negative pressure can be based upon physical limitations of the hollow fiber membranes, and that the flux is lower in each successive stage in FIG. 7 (e.g., each successive treatment tank 10a, 10b, 10c) due to the concentration of solid algae (due to the retentate produced) in each stage being higher while the pressure drop in each stage remains substantially the same. The backwash period and intervals for each stage or treatment tank can be adjusted independently to provide the highest net flux in each stage based upon, for example, the concentration level in that stage and/or the fouling characteristics of the algae. For example, in one embodiment, the system is configured to automatically alter at least one of the backwash period or interval for one or more of the multiple stages based upon one or more solid algae concentration reading from at least one concentration sensor. In another embodiment, the system is initially programmed or configured so that least one of the backwash period or interval of at least one of the stages is different from at least one of the other stages based upon known fouling characters of the algae in the algae slurry.

Like the system of FIG. 6, in certain embodiments, when the system of FIG. 7 is first started or initiated, the system operates in manner such that no retentate discharge occurs until a desired or predetermined suspended solids concentration level has been attained. In an embodiment, one or more concentration sensor can again be utilized to determine when the desired concentration has been reached. Such one or more sensor be located, for example, in treatment tanks 10a, 10b or 10c, or in any other suitable location.

Alternatively or additionally, the system of FIG. 7 can be configured to determine the concentration level attainment based upon volumetric control, which can utilize, for example, a flow meter or any known flow and/or volumetric parameters. Once the desired or predetermined suspended concentration level has been attained, the system is configured to gradually withdraw retentate or material (e.g., concentrated algae slurry) from treatment tank 10c via operation of pump 16 so as to maintain the predetermined level of concentration (e.g., opening a valve on a conduit with which pump 16 operates).

In an alternative non-limiting embodiment, once the desired or predetermined suspended concentration level has been attained, treatment tank 10c can be emptied and optionally rinsed. To empty the tank, filtration is stopped by closing valves 25c, 21c and 18b. Treatment tank 10c can then emptied via operation of pump 16 (e.g., opening a valve on a conduit with which pump 16 operates). After tank 10c is emptied, a rinse can optionally preformed prior to restarting the filtration of tank 10c. To perform a rinse, treatment tank 10c is filled with water or cleaning solution by opening cleaning valve 30c so that the water or solution can be added to tank 10c through valve 10c (e.g., allowing fluid to flow from a source or container through at least one conduit or inlet via opening valve 10c). Once the tank is filled and optionally mixed with air bubbles via blower 13, the rinse water or cleaning solution can be removed via pump 16. In some embodiments, the water used for the rinse can also contain cleaning chemicals to aid in rinsing the tank or cleaning the membranes. After the water or cleaning solution has been emptied from tank 10c via operation of pump 16 (e.g., opening a valve to allow fluid to flow through a conduit or outlet with which pump 16 operates), valve 18b can be opened to refill tank 10c, and then the system can be operated using valves 25c and 21c for filtration and backwash with no retentate discharge until the desired solids concentration level is attained again. In an embodiment, one or more concentration sensor can again be utilized to determine when the desired concentration has been reached. Such one or more sensor be located, for example, in treatment tanks 10a, 10b or 10c, or in any other suitable location. Alternatively or additionally, the system can be configured to determine the concentration level attainment based upon volumetric control, which can utilize, for example, a flow meter or any known flow and/or volumetric parameters.

In another alternative non-limiting embodiment, once the desired or predetermined suspended concentration level has been attained, feed valve 18b can be closed and the liquid level in treatment tank 10c can be controlled by intermittent opening of the feed valve 30c to add water or any other suitable replacement solution to replace the original media of the algae slurry. The water or replacement solution entering treatment tank 10c dilutes the original media and eventually replaces at least most of the media. The media replacement level can be monitored, sensed or determined by any suitable sensor or sensing methods such as (i) sensing or determining the difference in conductivity, pH, ion specific electrode, or specific gravity of the algae slurry retentate or permeate relative to the initial value of the of the in the algae slurry retentate or permeate, or (ii) sensing or determining the level of media replacement through total volumetric throughput of rinse water or solution, measured, for example, by a rinse feed flow meter or permeate flow meter, relative to the total volume of treatment tank 10c. Examples of media sensor include (i) a conductivity meter in the algae slurry in the at least one treatment tank or in the permeate leaving the at least one permeate conduit, (ii) a pH meter for the algae slurry in the at least one treatment tank or in the permeate leaving the through the at least one permeate conduit, (iii) a flow meter for the rinse fluid entering the at least one treatment tank, or (iv) a flow meter for the permeate leaving the at least one treatment tank. Once the desired or predetermined media replacement level has been reached, then the rinsed algae slurry retentate can be removed from treatment tank 10c through and outlet or conduit via operation of pump 16.

Like the embodiments of FIGS. 1 to 6, the system of FIG. 7 can also include one or more controller, which can be programmed or configured to operate with one or more of the valves, the blower, one or more of the pumps, any sensors and/or any other system components so as to perform various functions of the system including valving, pumping, backwashing, rinsing, filtration, permeate flow or any other system functions. In an embodiment, the one or more controller can include at least one processor and at least one memory device which stores instructions, which when executed by the at least one processor, cause the at least one processor to operate with one or more of the valves, the pumps, any sensors and any other components to perform operations of the filtration system. Various embodiments of the system of FIG. 7 can also include at least one input device and/or at least one display device, and the one or more controller can be programmed or configured to operate with the at least at least one input device and/or at least one display device.

It should be appreciated that in certain embodiments of FIG. 7, (as with the system of FIG. 6): (i) different backwash intervals and/or periods can be utilized for each treatment tank(s) or stage(s) (e.g., one or more earlier stages have a longer period, while one or more later stages have a shorter period, or one or more earlier stages have a longer interval, while one or more later stages have a shorter interval), (ii) the hollow fiber membrane area in each treatment tank(s) or stage(s) can be different (e.g., one or more earlier stages have a higher area, while one or more later stages have a lower area), and (iii) the permeate withdrawal rate of each treatment tank or stage can be allowed to vary. It should also be appreciated that the suspended solids content of the retentate in FIG. 7 is higher inside treatment tank 10b then it is in treatment tank 10a, and higher in treatment tank 10c then it is in treatment tank 10b, and that the suspended solids content in each tank 10a, 10b, 10c will reach a natural equilibrium based upon the in-feed rate, the permeate withdrawal rate from each treatment tank, and the retentate discharge rate due to the operation of pump 16.

While three stages are illustrated in the embodiments of FIGS. 6 and 7 (in the form of three differed treatment tanks), it should be appreciated that in various other embodiments, additional or fewer stages can be utilized (e.g., additional or fewer tanks). For example, in some systems, more than three stages can be utilized by adding additional treatment tanks with associated piping and valves. In one particular embodiment, two stages can be used by eliminating treatment tank 10b, along with its associated piping and valves. In certain multistage system embodiments, the system can include a single treatment tank having multiple stages defined by one or more divider separating the single treatment tank into different spaces or stages, rather than multiple separate tanks.

In various embodiments, the systems of FIGS. 6 and 7 can be arranged into groups such that modules, cassettes of modules, or banks of cassettes can be operated together as a single unit, and one or more stages can include two or more treatment tanks operated in parallel. A media rinse can also be incorporated into stages other than the final stage by adding isolation or bypass valves and a water inlet valve. Backwash can be assisted in various embodiments with the addition of chemicals, air, mechanical pulses, ultrasonic waves, and any other suitable methods. Modules or cassettes can also be rinsed or chemically cleaned periodically so that any fouling material that is not removed by backwashing is removed.

Figure 8:
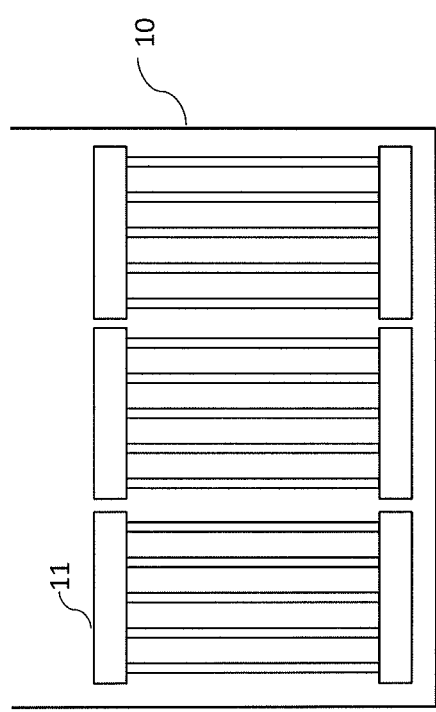
FIG. 8 illustrates an embodiment of a treatment tank for a hollow fiber dead-end filtration system of the present disclosure in which the treatment tank has generally vertical side walls.
Figure 9:
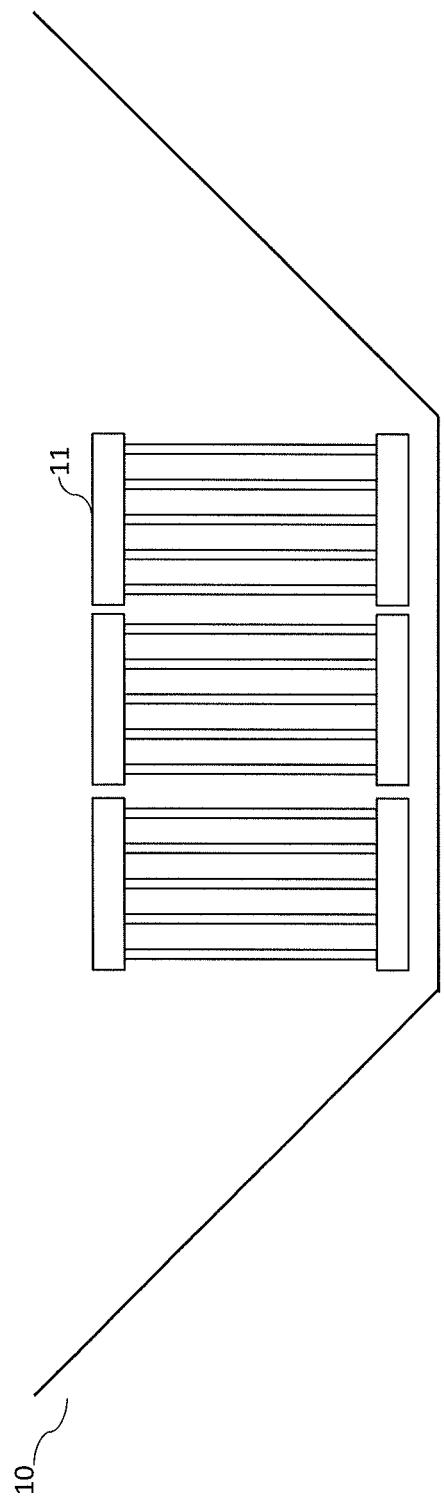
FIG. 9 illustrates another embodiment of a treatment tank for a hollow fiber dead-end filtration system of the present disclosure in which the treatment tank is an earthen lined tank or pond having angled side walls.

FIGS. 8 and 9 illustrate embodiments of treatment tanks 10 for use with any of the hollow fiber membrane filtration systems of the present disclosure (e.g., the multi-stage hollow fiber membrane filtration systems of FIGS. 6 and 7). Tanks 10 each include a plurality of modules 11 contained within the tanks 10. Each module 11 has a plurality of hollow fiber membranes. Each of the modules 11 can be arranged or grouped into cassettes (as discussed above), and the cassettes can be grouped into banks as discussed above. Each tank 10 can include a single module or multiple modules arranged into multiple cassettes.

Tank 10 of FIG. 8 can include one or more of plastic, metal, concrete and has generally vertical side walls extending from a generally horizontal base wall. Tank 10 of FIG. 9 is an earthen lined tank or pond having generally angled side walls extending from a generally horizontal base wall, each wall formed by the earth. In one embodiment, each of the side walls of earthen tank 10 extends at an angle from a vertical axis (e.g., 45 degrees from a vertical axis), and can include a lining to aid in containing or holding the in-feed algae or biological slurry inside the treatment tank 10. The lining of the earthen tank or pond 10 in FIG. 9 in one example includes plastic such as high-density polyethylene. The angled side walls formed by the earth allow a greater volume of liquid in-feed (e.g., and algae or biological slurry) to be contained within the earthen treatment tank 10, which can be detrimental in a single stage system, but can be suitable in multistage systems, as discussed below. The lined earthen treatment tank 10 is advantageous in that it is generally less expensive than concrete, plastic and/or metal treatment tanks. It should be appreciated that the packing density of the hollow fiber membranes in FIG. 8 (i.e., the area of the hollow fiber membranes relative to the total volume of tank 10 or the volume of fluid that is contained within tank 10) is greater than the packing density of the hollow fiber membranes in FIG. 9. In other words, the concrete, metal or plastic tank 10 of FIG. 8 includes tighter tolerances than the lined earthen tank 10 of FIG. 9.

Figure 10:
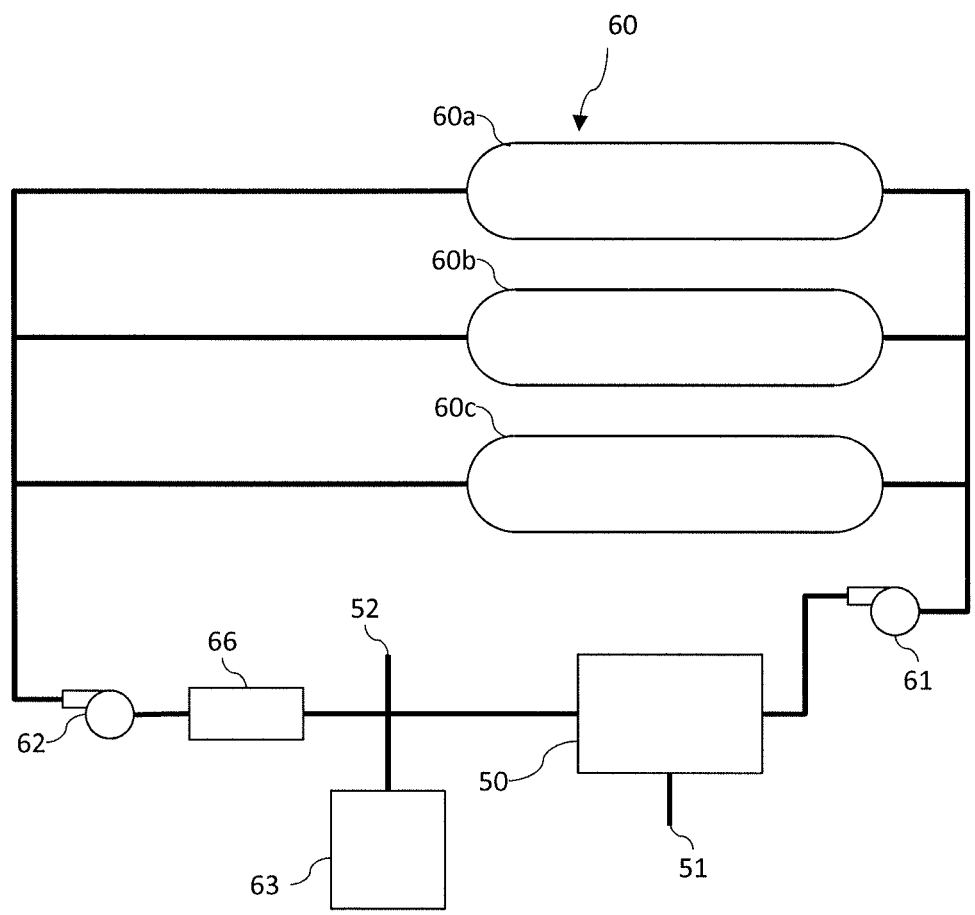
FIG. 10 is a schematic diagram illustrating an embodiment of an algae harvesting and cultivation system of the present disclosure in which carbon dioxide can be added, permeate can be re-used for cultivation, and live algae retentate can be attained.

Referring now to FIG. 10, one non-limiting embodiment of an algae harvesting and cultivation system of the present disclosure is illustrated in which carbon dioxide can be added, permeate can be re-used for cultivation, and live algae retentate can be attained. The system of FIG. 10 includes an algae cultivator 60 having one or more algae cultivation device 60a, 60b, 60c, such as one or more open raceway, closed photobioreactor, heterotrophic reactor, or a combination of open raceway closed photobioreactors, or heterotrophic reactors, or any other suitable algae cultivation devices. Nutrients, make-up water, carbon dioxide, and other material for cultivation of the algae can be added to algae cultivator 60 as needed to attain desired growth conditions. When a portion or all of the algae from cultivator 60 is ready to be harvested, the media containing algae can flow or otherwise be transferred from cultivator 60 (e.g., allowing the fluid to flow from the cultivator through one or more conduit via gravity, or in some embodiments pumping the fluid to the cultivator through the at least one conduit using pump 61) into a hollow fiber dead-end filtration system 50, such as one or more of the dead-end filtration systems described herein. In one particular embodiment, the dead-end filtration system includes a plurality of filtration stages (e.g., the systems of FIGS. 6 and 7). A recycled media hold-up reservoir 63 in fluid communication with the dead-end filtration system (e.g., via one or more conduit) can receive and store recycled media from the dead-end filtration system 50*a*, at least until the media is needed again in the algae cultivator 60. If a portion or all of the media needs to be replaced, then the media can be discharged through a drain outlet or conduit 52 (e.g., via operating a valve on the conduit), and the new media can be added to the cultivator 60. Nutrients such as carbon dioxide can be mixed with the recycled media in a nutrient supply contactor 66 that can be in fluid communication with the hold-up reservoir 63 or the dead-end filtration system 50 (e.g., through one or more conduit for each). Non-limiting examples of nutrient supply contactor 66 include a mixing nozzle in the recycled media conduit, a two-phase static mixer or a packed bed absorber. The permeate can then flow or otherwise be transferred or recycled back to the cultivation system 60 (e.g., flowing the permeate through at least one conduit, which in some embodiments can be achieved via gravity or via pump 62).

Before removing the concentrated algae slurry from hollow fiber dead-end filtration system 50, the retentate can be rinsed, for example, according to any of the rinsing procedures or sequences described herein. In various embodiments, rinsing can be performed by stopping the liquid in-feed to filtration system 50 (or stopping the feed to a last stage of filtration system 50 in a multistage filtration system such as the systems illustrated by FIG. 6 or 7), and feeding water to the filtration system 50 (or feeding water to the last stage of filtration system 50 in a multistage filtration system such as the systems of FIG. 6 or 7) to displace the media. The permeate recovered during the rinsing can added to the recycled media or discharged from the system. Once a sufficient quantity of water has been fed to reduce the media content of the retentate to the desired level, the rinsed, concentrated algae slurry obtained from the hollow fiber dead-end filtration system 50 can then be discharged for further treatment, re-cultivation, or storage. If pre-treatment is used, the type of pre-treatment can depend upon the algae and the algae product.

The concentrated algae slurry retentate from the hollow fiber dead-end filtration system 50 can be removed via an outlet or conduit 51 where the algae slurry can be held or stored in, for example, an algae container. The algae in the retentate is typically viable and can be re-cultivated or stored and then re-cultivated.

If cultivator 60 needs to be temporarily stopped, for example, to avoid dilution in a large rain event or to avoid overheating in high temperature event, or if the media needs to be replaced, for example because of dissolved organics or inorganics, then the all of the algae can be harvested by transferring all of the media containing the algae via pump 61 from algae cultivator 60 to the dead-end filtration system 50. The permeate can be discharged through drain outlet or conduit 52, or stored in the recycled permeate hold-up reservoir 63 (e.g., via the permeate flowing or otherwise being transferred to the at least one cultivator through for example at least one conduit). The retentate can optionally be rinsed as described herein, and then re-cultivated in algae cultivator 60 with new media. If the algae is to be stored before re-cultivation then the algae slurry retentate removed via outlet or conduit 51 can be packaged and stored at a cold temperature, e.g. less than 4° C., until the retentate will be used for re-cultivation.

If the algae needs to be stored for re-cultivation at a later time, for example, to supply the algae to a separate cultivation facility, to use the algae as live feed at a separate aquaculture facility, or to provide storage of algae for inoculation if the algae cultivator 60 needs to be restarted, all or a portion of the algae can be harvested by transferring or allowing all of the media containing the algae to flow or otherwise be transferred (e.g., via pumping the algae from cultivator 60 through at least one conduit via pump 61) to the dead-end filtration system 50. The permeate can be stored in a recycled permeate hold-up reservoir 63, which can be in fluid communication with the hollow fiber filtration system 50 via at least one conduit, and recycled. The retentate can optionally be rinsed according to any rinse procedure described herein, and re-cultivated in cultivator 60 with new media. If the algae is to be stored before re-cultivation, then the algae slurry retentate can be removed via an outlet or conduit 51 to, for example, at least one algae container, and can be packaged and stored at cold temperatures, e.g. less than 4° C., until re-cultivation.

Figure 11:
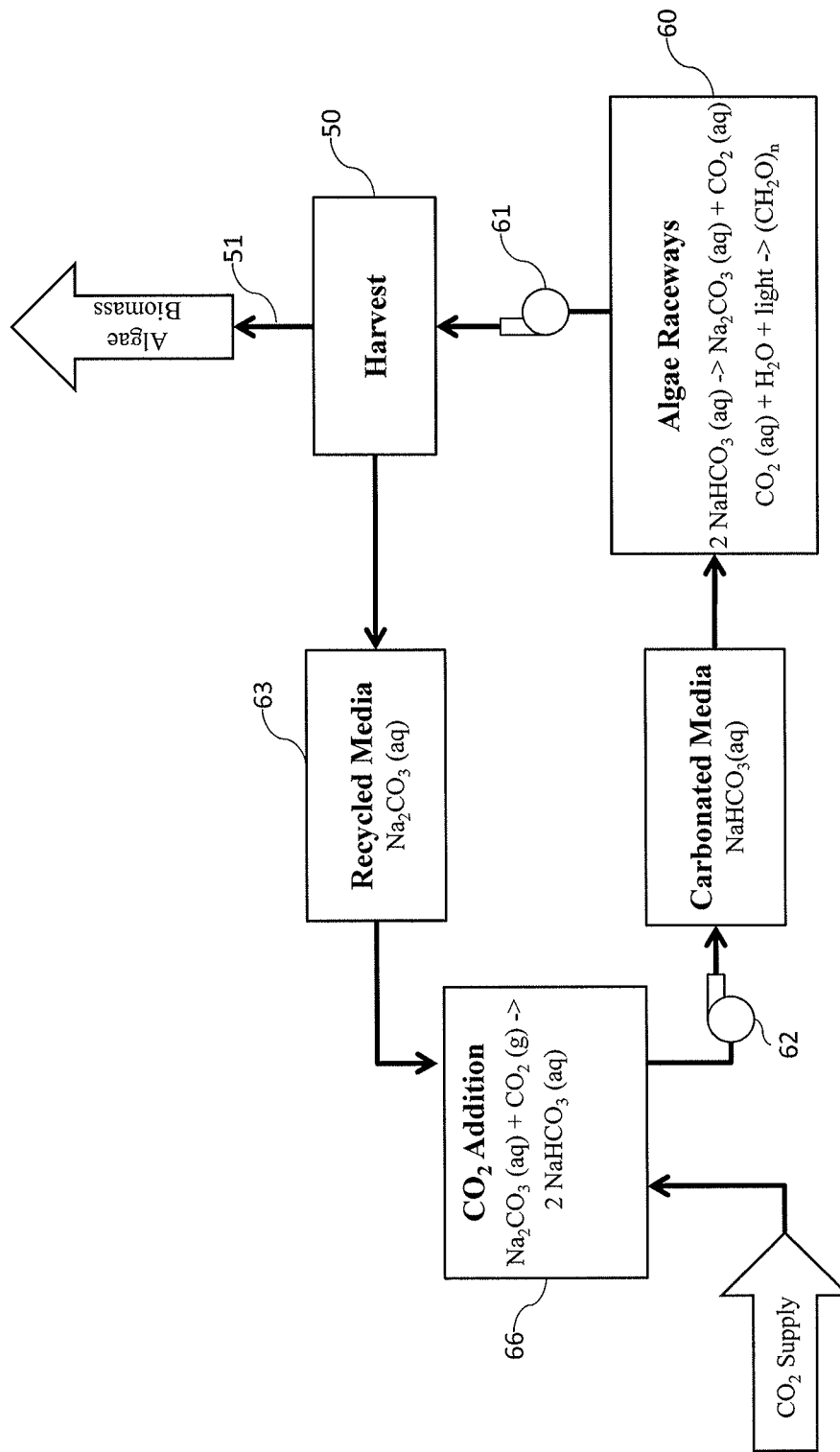
FIG. 11 is a flow chart illustrating an embodiment of utilizing a carbonate-bicarbonate shuttle for a carbon dioxide cycle in the system of FIG. 10.

Referring now to FIG. 11, one non-limiting method for utilizing a carbonate-bicarbonate shuttle for a carbon dioxide cycle in the system of FIG. 10 is illustrated. The media for algae cultivator 60 contains sodium bicarbonate and sodium carbonate. As the algae undergoes photosynthesis, carbon dioxide is consumed to make biomass. As carbon dioxide is consumed, sodium bicarbonate is converted to sodium carbonate. When a portion or all of the algae is ready to be harvested, the media containing algae flows or is transferred (e.g., pumping the algae through at least one conduit via pump 61) from algae cultivator 60 to hollow fiber dead-end filtration system 50, such as one or more of the dead-end filtration systems described herein including any of the systems having multiple stages or treatment tanks. A permeate is obtained from the hollow fiber dead-end filtration system 50 and can be transferred or stored in a recycled media hold-up reservoir 63 (e.g., via the permeate flowing or otherwise being transferred or pumped through at least one conduit to the reservoir 63) until the recycled media is needed for cultivation. Carbon dioxide can be mixed with the recycled media in a nutrient or carbon dioxide adder or supply contactor 66 that is in fluid communication with the reservoir 63 (e.g., via one or more fluid conduit). Non-limiting examples of a contactor include a mixing nozzle in the recycled media conduit, a two-phase static mixer or a packed bed absorber. When the carbon dioxide dissolves in the media, sodium carbonate is converted back to sodium bicarbonate. The carbonated recycled media can flow or otherwise be transferred back to the algae cultivator 60 (e.g., by pumping the media through at least one conduit via pump 62 or via gravity flowing the media) and the above cycle can be repeated. It should be recognized that the carbon dioxide can be added before or after pump 62, and that a carbonated media hold-up reservoir 63 could be added to store the carbonated media prior to transferring the media to the cultivator 60.

Figure 12:
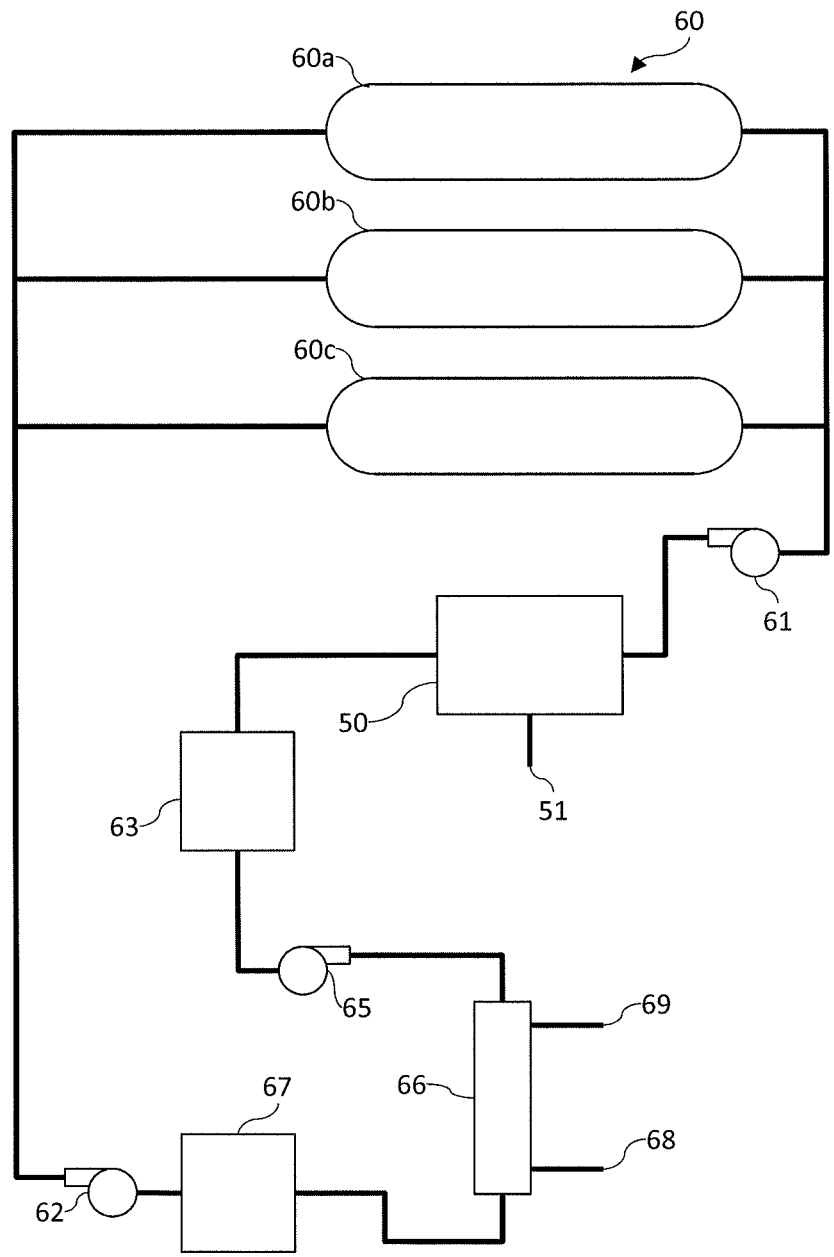
FIG. 12 is a schematic diagram illustrating an embodiment of a harvesting and cultivation system of the present disclosure having dead-end filtration and in which the media is recharged with carbon dioxide through an absorber prior to recycling the media to an algae cultivator.

Referring now to FIG. 12, one non-limiting embodiment of a harvesting and cultivation system is illustrated in which the media is recharged with carbon dioxide through an absorber 69 prior to recycling the media to algae cultivator 60. Absorber 69 of FIG. 12 and any other absorbers of the present disclosure can operate via a blower or via a pressure difference between an inlet and outlet of absorber 69. The system of FIG. 12 includes many of the same components described above in connection with FIGS. 10 and 11. Those components in FIG. 12 are marked with the same or similar element numbers as used in FIGS. 10 and 11. The description of those elements including each of the alternatives discussed above in connection with FIGS. 10 and 11 apply in many respect to like element numbers in FIG. 12.

The system of FIG. 12 operates such that when a portion or all of the algae is ready to be harvested after cultivating in algae cultivator 60, the media containing algae and sodium carbonate can flow or otherwise be transferred from algae cultivator 60 to hollow fiber dead-end filtration system 50 (e.g., flowing the algae through at least one conduit, which in an embodiment can be achieved via gravity or pump 61). The dead-end filtration system can be one or more of the dead-end filtration systems described herein including the multistage systems such as FIGS. 6 and 7. The permeate obtained from hollow fiber dead-end filtration system 50 (e.g., any of the dead-end filtration systems described herein including the multistage systems such as FIGS. 6 and 7) can flow or otherwise be transferred (e.g., via the permeate flowing through at least one conduit which in an embodiment can be achieved via gravity) and stored in a recycled media hold-up reservoir 63 until the media is needed in the packed bed absorber 66. The recycled media can flow or otherwise be transferred from reservoir 63 to packed bed absorber 66 (e.g., the media flowing through at least one conduit, which in an embodiment can be achieved via gravity or via pump 65). The recycled media can flow through the packed bed absorber 66 (e.g., via gravity). The recycled media contacts a gas containing carbon dioxide in the packed bed absorber 66, where the sodium carbonate in the media is converted to sodium bicarbonate resulting in a carbonated media. The carbon dioxide containing gas can enter the absorber 66 through a gas inlet or conduit 68, which in an embodiment can be located at the bottom of packed bed absorber 66. The carbon dioxide absorbed by the recycled media in the packed bed absorber 66 reduces the concentration of carbon dioxide in the gas. The carbon dioxide depleted gas can exit the absorber 66 through a gas outlet or conduit 69, which in an embodiment can be located at the top of the absorber 66. The carbonated media can flow or otherwise be transferred from the absorber to a storage carbonate media hold-up reservoir 67 (e.g., via the fluid flowing through at least one conduit, which in an embodiment can be achieved via gravity). The reservoir 67 can be covered with a carbon dioxide retaining lid or cover so that the carbon dioxide does not escape into the atmosphere. When the carbonated media is needed in algae cultivator 60, the carbonated media can flow or otherwise be transferred from the carbonated media hold-up reservoir 67 back to the algae cultivator 60 (e.g., via flowing the carbonated media through at least one conduit, which in one embodiment can be achieved via gravity or via pump 62). It should be appreciated that any conduit between the hold-up reservoir 67 and algae cultivator 60 can be enclosed so that the carbon dioxide does not escape to the atmosphere. Examples of enclosed conduits include a pipe or a covered, lined aqueduct. It should further be appreciated that the absorber 66 can include multiple packed bed columns instead of a single packed bed column. If multiple packed bed columns are used, the gas and liquid fluid can flow through the columns in series or in parallel.

Figure 13:
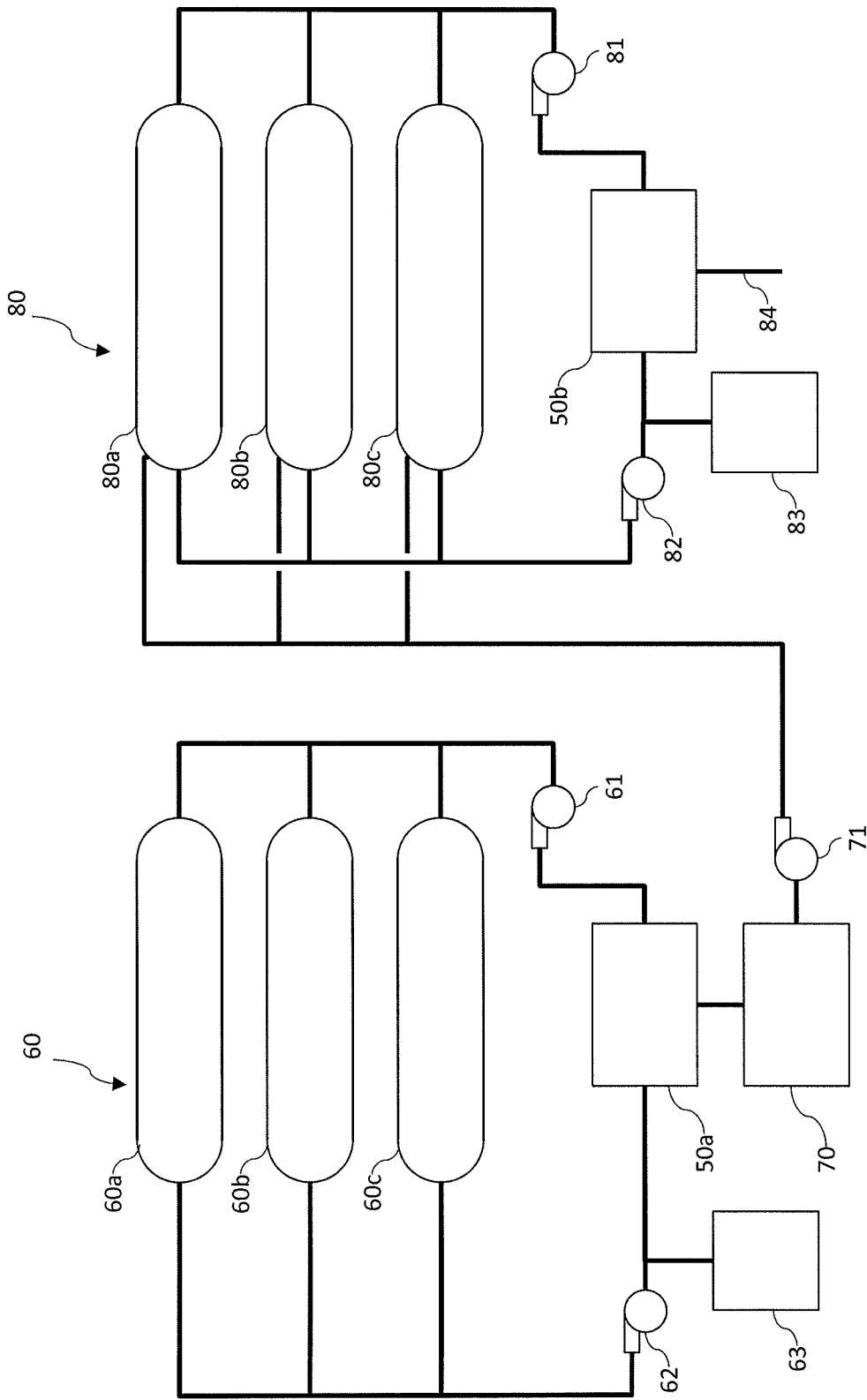
FIG. 13 is a schematic diagram illustrating an embodiment of a multi- or two-stage cultivation and harvesting system of the present disclosure having separate media in each cultivation stage.

Referring now to FIG. 13, one non-limiting embodiment of a harvesting and cultivation system of the present disclosure is illustrated in which separate media is used in each cultivation stage. The system of FIG. 13 cultivates algae in a first algae cultivator 60 which defines a first cultivation stage, and a separate second algae cultivator 80 which defines a second cultivation stage. The cultivation and harvesting system of FIG. 13 includes many of the same components described above in connection with FIG. 10-12. Those components in FIG. 13 are marked with the same or similar element numbers as used in FIGS. 10-12.

First cultivation stage 60 can include one or more algae cultivation device 60a, 60b, 60c, such as one or more open raceway, closed photobioreactor, heterotrophic reactor, or a combination of open raceway closed photobioreactors, or heterotrophic reactors, or any other suitable algae cultivation devices. Nutrients, make-up water, carbon dioxide, and other material for cultivation of the algae can be added to first cultivation stage 60 as needed to attain desired growth conditions. When a portion or all of the algae is ready to be moved to the second stage 80 of the two-stage cultivation and harvesting system, the first stage media containing algae can flow or otherwise be transferred from first cultivation stage 60 to a first hollow fiber dead-end filtration system 50a, such as one or more of the dead-end filtration systems described herein including the multi-stage systems of FIGS. 6 and 7. The first stage media containing algae can flow or otherwise be transferred through at least one conduit, which in an embodiment can be achieved via gravity flow through at least one conduit or via pumping the media through the at least one conduit via pump 61. The permeate obtained from the first hollow fiber dead-end filtration system 50a can flow or otherwise be transferred and recycled back to the first cultivation stage 60 (e.g., flowing the permeate through at least one conduit to the first cultivation stage 60, which in an embodiment can be achieved via gravity or pump 62). A recycled media hold-up reservoir 63 for the first stage recycled media can be in fluid communication with the first filtration system 50a (e.g., at least one conduit via gravity) and be used to store the recycled media until the media is needed in the first cultivation stage 60. In this regard, it should be appreciated that the permeate from the first filtration system 50a can flow or otherwise be transferred from filtration system 50a to the reservoir 63 through at least one conduit which can be achieved via gravity in an embodiment, and then recycled media held in the reservoir 63 can be transferred or otherwise flow from the reservoir back to the first cultivation stage 60 through at least one other conduit, which in an embodiment can be achieved via gravity or pump 62. If the elevation of the permeate outlet of filtration system 50a is higher than the elevation of reservoir 63, then the recycled media can flow from filtration system 50a to the reservoir 63 by gravity. If the elevation of the reservoir 63 is higher than the elevation of the inlet section of the first cultivation stage 60, then the recycled media can also flow from reservoir 63 to first cultivation stage 60 by gravity.

Before removing the concentrated algae slurry from hollow fiber dead-end filtration system 50a, the first stage media can be rinsed according to any rinse method or sequence described herein. Rinsing can be performed by stopping the liquid in-feed to the filtration system (or stopping the last stage of filtration in a multi-stage filtration system), and feeding water or other suitable rinsing solution to the system to displace the first cultivation stage media (e.g. feeding water or solution from a source or container). The permeate recovered during the rinsing can be added to the first stage recycled media or discharged from the system. Once a sufficient quantity of water has been fed to reduce the first stage media to the desired level, the rinsed, concentrated algae slurry obtained from the hollow fiber dead-end filtration system 50a can flow or otherwise be transferred (e.g., flow through at least one conduit which in an embodiment can be achieved via gravity) to a pre-treatment system 70 to be pretreated as described herein. The type of pre-treatment can depend upon the algae and the algae product. For example, chemical treatment, ozone, low concentration of bleach, an acid or a base can be used to stress the algae to induce oil formation in the second algae cultivation stage. In one example embodiment, the algae is mixed with a chemical in a tank for a short period of time (e.g., less than 1 hour) prior to algae flowing or otherwise being transferred to the second cultivation stage 80 and dilution in the second stage media.

The rinsed, concentrated algae slurry can then flow or otherwise be transferred to second cultivation stage 80 (e.g., flowing the rinsed concentrated algae slurry through at least one conduit, which in an embodiment can be achieved via gravity or pump 71), where additional algae can be cultivated in a second cultivation stage media, which can be different from the first cultivation stage media. Like the first cultivation stage 60, the second cultivation stage 80 also includes one or more algae cultivation devices 80*a*, 80*b*, 80*c*, such as an open raceway, a closed photobioreactor, a combination of open raceways and closed photobioreactors, a heterotrophic reactor, or any other suitable algae cultivation devices. If the treatment tank in filtration system 50*a* is lower in elevation than the outlet of cultivation stage 60, then the algae slurry can flow from cultivation stage 60 to filtration system 50*a* by gravity. If the outlet of the recycled media from filtration system 50*a* is higher in elevation than the inlet of cultivation stage 60, then the recycled media can flow back to cultivation stage 60 from the filtration system 50*a* by gravity. If the retentate outlet of filtration system 50*a* is higher in elevation than the inlet section of cultivation stage 80, then the retentate algae slurry can flow by gravity from filtration system 50*a* to cultivation stage 80.

When a portion or all of the additional algae is ready to be harvested, the second stage media containing the additional algae can flow or otherwise be transferred (e.g., flowing the additional algae through at least one conduit, which in an embodiment can be achieved via gravity or pump 81) from the second cultivation stage 80 to a hollow fiber dead-end filtration system 50*b*, such as one or more of the hollow fiber dead-end filtration systems described herein including the multistage systems. The permeate obtained from hollow fiber dead-end filtration system 50*b* can flow or otherwise be transferred or recycled back to second cultivation stage 80 (e.g., flowing the permeate through at least one conduit, which in an embodiment can be achieved via gravity or pump 82). A recycled media hold-up reservoir 83, like the reservoir 63 in the first cultivation stage 60, can be in fluid communication with the hollow fiber dead-end filtration system 50*b* and can be used to store the recycled media until the recycled media is needed in the second cultivation stage 80. In this regard, it should be appreciated that the permeate from second filtration system 50*b* can flow or otherwise be transferred from system 50*b* to reservoir 83 through at least one conduit, and the recycled media held in the reservoir 83 can be transferred or otherwise flow from reservoir 83 back to second cultivation stage 80 through at least one other conduit, which in an embodiment can be achieved via gravity or pump 82. The concentrated algae slurry product obtained from the dead end filtration system 50*b* can be rinsed according to any rinsing method or sequence described herein prior to removal of the concentrated algae through an outlet or conduit 84. In an embodiment, the permeate obtained during the rinsing can either be added to the second stage recycled media or discharged from the system.

Figure 14:
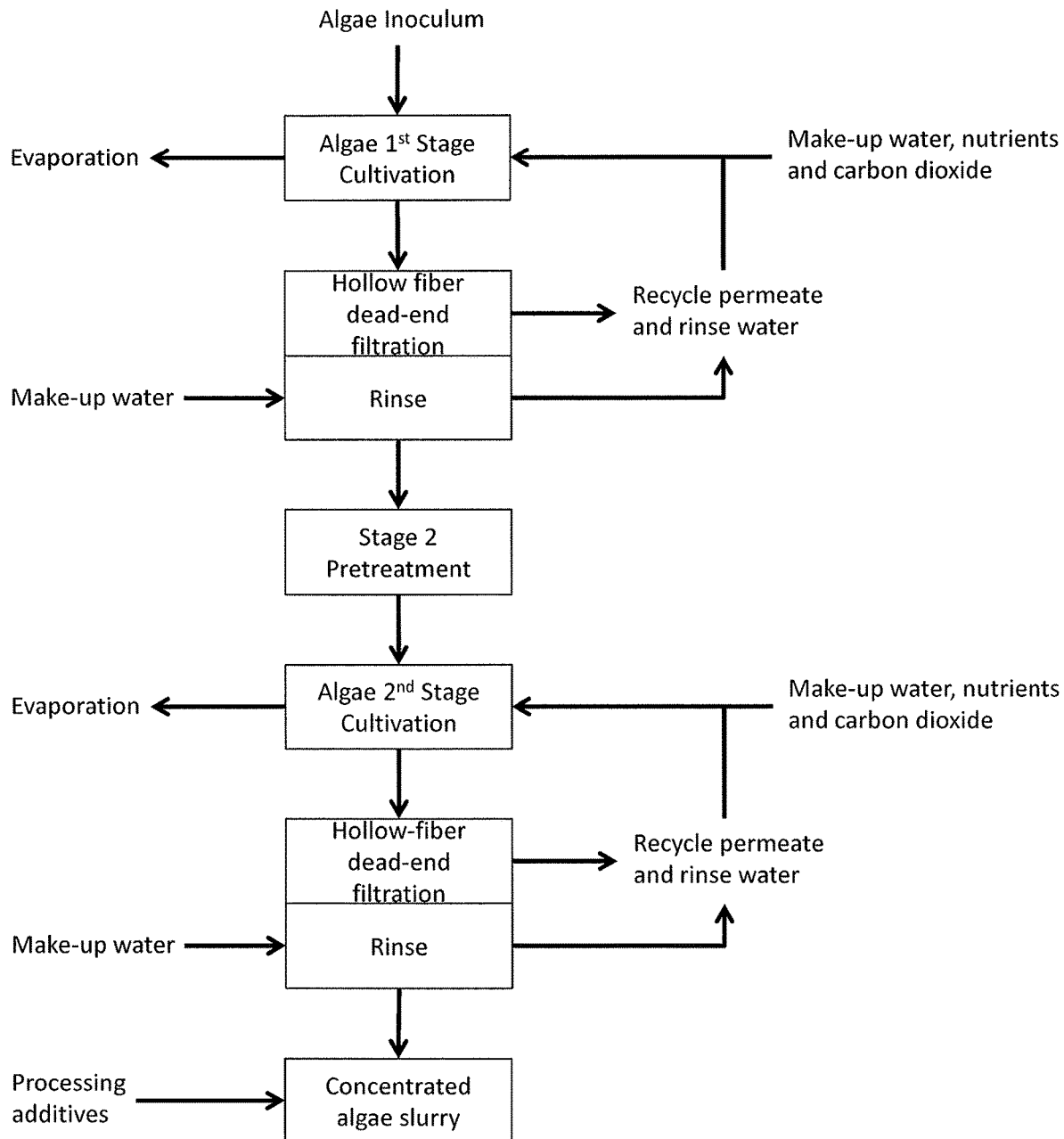
FIG. 14 is a flow chart illustrating an embodiment of a multi- or two-stage cultivation and harvesting system and method of the present disclosure that incorporates hollow fiber dead-end filtering, rinsing, second stage pre-treating as well as recycling and recovering of separate media for each stage.

Referring now to FIG. 14, a non-limiting embodiment of a process or method for cultivating and harvesting algae in an algae harvesting and cultivation system of the present disclosure is illustrated in which separate media is used for each stage of cultivation. In the first cultivation stage shown in FIG. 14, media, nutrients, and/or carbon dioxide can be added to support algae growth of, for example, an algae inoculum. The media can contain water with any desired dissolved solids. Evaporation of liquid can take place during the first cultivation stage, so make-up water can be added to maintain the media composition.

The algae cultivated in the first stage can be harvested through a first hollow fiber dead-end filtration system, such as one or more of the systems described herein in which there is low shear stress so that the algae remains intact, and viable algae cells can be recovered in the retentate. Permeate from the first dead-end filtration system can be recycled back to the first cultivation stage of the system. At least a portion of the make-up water needed to maintain the media concentration in the cultivation stage can be used to rinse the algae, and the rinse permeate can also be recycled back to the first cultivation stage so that substantially all of the dissolved components are recovered in the recycled permeate and rinse water. The retentate produced from the first dead-end filtration system can therefore be free or substantially free of any components from the first cultivation stage.

The algae produced from the first cultivation stage and the first hollow fiber dead-end filtration system can then be pretreated to impart stress, and a chemical trigger can be added for secondary metabolite formation. Other adjustments can also be made to induce algae product formation in the second algae cultivation. At the second stage of cultivation, media, nutrients, and carbon dioxide can again be added to support additional algae product formation. Evaporation of liquids can also take place during the second cultivation stage. The algae from the second cultivation stage can be harvested through a second hollow fiber dead-end filtration system, such as one or more of the systems described herein with low shear stress on the algae. The permeate from the second dead-end filtration system can be recycled to the second cultivation stage. Water can again evaporate from the system, so make-up or additional water can be added to maintain the media composition. At least a portion of the make-up water can be used to rinse the additional algae, and the rinse permeate can be recycled back to the second cultivation stage so that all or substantially all of the dissolved components are recovered in the recycled permeate and rinse water. Any needed processing additives such as acids, bases, salts or polymers can be added to the concentrated slurry, and the algae slurry can be processed to recover algae products.

The systems and methods discussed above with respect to FIGS. 13 and 14 enable algae to be cultivated and harvested using two separate media that can have different osmotic strength, pH, nutrient loading, and/or chemical triggers without contaminating one media with the other media or needing the first stage media to be treated prior to entering the second stage of cultivation. The systems and methods also enable a rapid change from the first media to the second media without requiring large chemical additions to change the first stage media composition to the second stage media composition. Still further, the systems and methods allow adjustments to be made for processing the algae slurry into a product, such as a pH change, without requiring large chemical additions to change the second stage media composition. The process and systems also enable recovery of substantially all of the dissolved solids in each media, and substantially eliminates the dissolved solids content in the harvested algae slurry.

Figure 15:
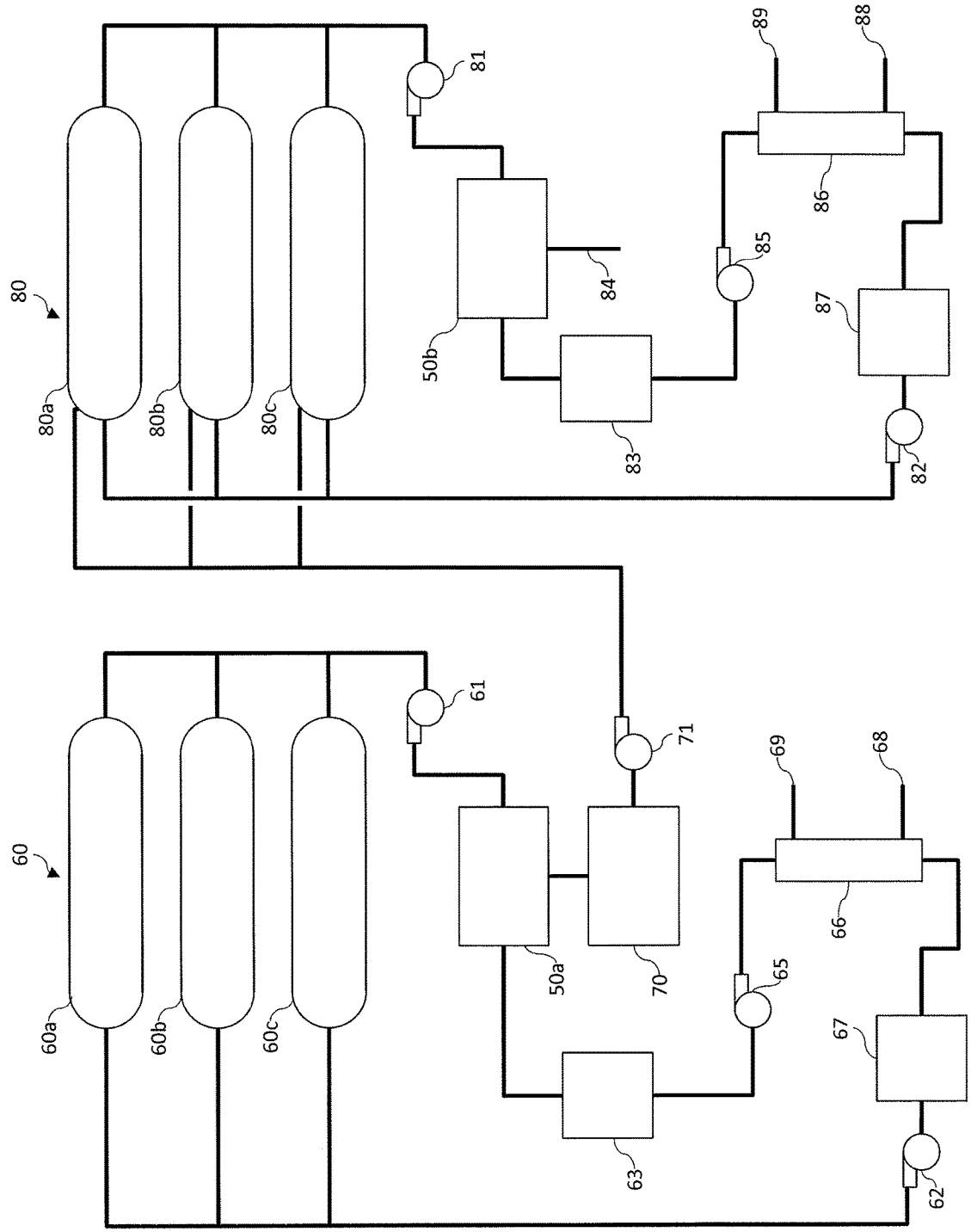
FIG. 15 is a schematic diagram illustrating an embodiment of a multi- or two-stage cultivation and harvesting system of the present disclosure having dead-end filtration and in which carbon dioxide can be added and separate media can be used in each cultivation stage.

Referring now to FIG. 15, one non-limiting embodiment of an algae harvesting and cultivation system of the present disclosure is illustrated in which carbon dioxide can be added and separate media can be used in each cultivation stage. The system of FIG. 15 cultivates algae in a first algae cultivator 60 defining a first cultivation stage, and a separate second algae cultivator 80 defining a second cultivation stage. The system of FIG. 15 also includes a first dead-end hollow fiber filtration system 50*a*, a carbon dioxide absorber 66, and a second dead-end hollow fiber filtration system 50*b* and another carbon dioxide absorber 86. FIG. 15 includes many of the same components described above in connection with FIGS. 12 and 13. Those components in FIG. 15 are marked with the same or similar element numbers as used in FIGS. 12 and 13. The description of those elements including each of the alternatives discussed above in connection with FIGS. 12 and 13 apply in many respect to like element numbers in FIG. 15.

The system of FIG. 15 operates in an embodiment such that when a portion or all of the algae is ready to be harvested after cultivating in algae cultivator 60, the media containing algae and sodium carbonate can flow or otherwise be transferred from algae cultivator 60 to hollow fiber dead-end filtration system 50*a* (e.g., flowing the algae from cultivator 60 to dead-end filtration system 50*a* through at least one conduit, which in an embodiment can be achieved via gravity or pump 61). The dead-end filtration system 50*a* can be one or more of the dead-end filtration systems described herein including the multi-stage systems such as FIGS. 6 and 7. The permeate obtained from hollow fiber dead-end filtration system 50*a* can flow or otherwise be transferred (e.g., the permeate flowing through at least one conduit which in an embodiment can be achieved via gravity) and stored in a recycled media hold-up reservoir 63 until the media is needed in a packed bed absorber 66. The recycled media in reservoir 63 can flow or otherwise be transferred from reservoir 63 to packed bed absorber 66 (e.g., flowing the recycled media through at least one conduit, which in an embodiment can be achieved via gravity or pump 65). The recycled media can flow through packed bed absorber 66 (e.g., via gravity) where the media contacts a gas containing carbon dioxide in the absorber 66 and sodium carbonate in the media can be converted to sodium bicarbonate resulting in a carbonated media. The carbon dioxide containing gas can enter the absorber 66 through a gas inlet or conduit 68, which in an embodiment can be located at the bottom of packed bed absorber 66. The carbon dioxide absorbed by the recycled media in the packed bed absorber 66 reduces the concentration of carbon dioxide in the gas. The carbon dioxide depleted gas can exit the absorber 66 through a gas outlet or conduit 69, which in an embodiment can be located at the top of absorber 66. The carbonated media can flow or otherwise be transferred from absorber 66 to a storage carbonate media hold-up reservoir 67 (e.g., via the fluid flowing through at least one conduit, which can be achieved in an embodiment via gravity). The reservoir 67 can be covered with a carbon dioxide retaining lid or cover so that the carbon dioxide does not escape into the atmosphere.

When the carbonated media is needed in algae cultivator 60, the carbonated media can flow or otherwise be transferred from the carbonated media hold-up reservoir 67 back to the algae cultivator 60 (e.g., flowing the carbonated media through at least one conduit, which in an embodiment can be achieved via gravity or pump 62). It should be appreciated that any conduit between the hold-up reservoir 67 and first algae cultivator or stage 60 can be enclosed so that the carbon dioxide does not escape to the atmosphere. Examples of enclosed conduits include a pipe or a covered, lined aqueduct. It should further be appreciated that in certain embodiments absorber 66 can include multiple packed bed columns instead of a single packed bed column. If multiple packed bed columns are used, the gas and liquid fluid can flow through the columns in series or in parallel.

First algae cultivator or stage 60, can include one or more algae cultivation device 60*a*, 60*b*, 60*c*, such as one or more open raceway, closed photobioreactor, heterotrophic reactor, or a combination of open raceway closed photobioreactors, or heterotrophic reactors, or any other suitable algae cultivation devices. Nutrients, make-up water, carbon dioxide, and other material for cultivation of the algae can be added to first cultivation stage 60 as needed to attain desired growth conditions.

Before removing the concentrated algae slurry from hollow fiber dead-end filtration system 50*a*, the first stage media can be rinsed according to any rinse method or sequence described herein. Rinsing can be performed by stopping the liquid in-feed to the filtration system (or stopping the last stage of filtration in a multi-stage filtration system), and feeding water or other suitable rinsing solution to the system to displace the first cultivation stage media. The permeate recovered during the rinsing can be added to the first stage recycled media or discharged from the system. Once a sufficient quantity of water has been fed to reduce the first stage media to the desired level, the rinsed, concentrated algae slurry obtained from the hollow fiber dead-end filtration system 50*a* can flow or otherwise be transferred (e.g., flow through at least one conduit, which in an embodiment can be achieved via gravity) to a pre-treatment system 70 to be pretreated as described herein. The type of pre-treatment can depend upon the algae and the algae product. For example, chemical treatment, ozone, low concentration of bleach, an acid or a base can be used to stress the algae to induce oil formation in the second algae cultivation stage. In one example embodiment, the algae is mixed with a chemical in a tank for a short period of time (e.g., less than 1 hour) prior to algae flowing or otherwise being transferred to the second cultivation stage 80 and dilution in the second stage media. The rinsed, concentrated algae slurry can flow or otherwise be transferred to second algae cultivator or cultivation stage 80 (e.g., flowing the rinsed concentrated algae slurry through at least one conduit, which in an embodiment can be achieved via gravity or pump 71), where additional algae can be cultivated in a second cultivation stage media, which can be different from the first cultivation stage media. Like first cultivation stage 60, the second cultivator or cultivation stage 80 also includes one or more algae cultivation devices 80*a*, 80*b*, 80*c*, such as an open raceway, a closed photobioreactor, a combination of open raceways and closed photobioreactors, a heterotrophic reactor, or any other suitable algae cultivation devices.

When a portion or all of the additional algae is ready to be harvested from second cultivator or cultivation stage 80, the second stage media containing the additional algae can flow or otherwise be transferred (e.g., flowing the additional algae through at least one conduit, which in an embodiment can be achieved via gravity or pump 81) from second cultivation stage 80 to another or second hollow fiber dead-end filtration system 50*b*, such as one or more of the hollow fiber dead-end filtration systems described herein including the multistage systems of FIGS. 6 and 7. A recycled media hold-up reservoir 83, like the reservoir 63 in the first cultivation stage 60, can be in fluid communication with hollow fiber dead-end filtration system 50*b*, and can be used to store the recycled media until the recycled media is needed in the second cultivation stage 80. In this regard, it should be appreciated that the permeate from second filtration system 50*b* can flow or otherwise be transferred from filtration system 50*b* to reservoir 83 through at least one conduit.

The concentrated algae slurry product obtained from dead end filtration system 50*b* can be rinsed according to any rinsing method or sequence described herein prior to removal of the concentrated algae through an outlet or conduit 84. In an embodiment, the permeate obtained during the rinsing can either be added to the second stage recycled media or discharged from the system. Rinsing can be performed by stopping the liquid in-feed to the filtration system (or stopping the last stage of filtration in a multi-stage filtration system), and feeding water or other suitable rinsing solution to the system to displace the second cultivation stage media. The permeate recovered during the rinsing can be added to the second stage recycled media or discharged from the system.

The permeate obtained from hollow fiber dead-end filtration system 50*b* that is stored in a recycled media hold-up reservoir 83 can be stored until the media is needed in a packed bed absorber 86. The recycled media can flow or otherwise be transferred from reservoir 83 to packed bed absorber 86 (e.g., flowing the recycled media through at least one conduit, which in an embodiment can be achieved via gravity or pump 85). The recycled media can flow through absorber 86 (e.g., via gravity) where the media contacts a gas containing carbon dioxide in the absorber 86, and sodium carbonate in the media can be converted to sodium bicarbonate resulting in a carbonated media. The carbon dioxide containing gas can enter absorber 86 through a gas inlet or conduit 88, which in an embodiment can be located at the bottom of packed bed absorber 86. The carbon dioxide absorbed by the recycled media in absorber 86 reduces the concentration of carbon dioxide in the gas. The carbon dioxide depleted gas can exit absorber 86 through a gas outlet or conduit 89, which in an embodiment can be located at the top of absorber 86. The carbonated media can flow or otherwise be transferred from absorber 86 to a storage carbonate media hold-up reservoir 87 (e.g., via the fluid flowing through at least one conduit, which in an embodiment can be achieved via gravity). The reservoir 87 can be covered with a carbon dioxide retaining lid or cover so that the carbon dioxide does not escape into the atmosphere.

When the carbonated media is needed in algae cultivator or stage 80, the carbonated media can flow or otherwise be transferred from the carbonated media hold-up reservoir 67 back to second algae cultivator or cultivation stage 80 (e.g., via flowing the carbonated media through at least one conduit, which in an embodiment can be achieved via gravity or pump 82). It should be appreciated that any conduit between the hold-up reservoir 87 and algae cultivator 80 can be enclosed so that the carbon dioxide does not escape to the atmosphere. Examples of enclosed conduits include a pipe or a covered, lined aqueduct. It should further be appreciated that the absorber 86 can include multiple packed bed columns instead of a single packed bed column. If multiple packed bed columns are used, the gas and liquid fluid can flow through the columns in series or in parallel.

It should be appreciated that like the systems and methods illustrated by the embodiments of FIGS. 1 to 9, each of the algae harvesting and cultivation systems and methods illustrated by the embodiments of FIGS. 10 to 15 can include one or more controller, which can be programmed or configured to operate with one or more of the system components so as to perform various functions of the system including valving, cultivating, harvesting, pumping, backwashing, rinsing, filtration, permeate flow, chemical cleaning, storing, flowing or any other system functions. In an embodiment, the one or more controller can include at least one processor and at least one memory device which stores instructions, which when executed by the at least one processor, cause the at least one processor to operate with any of the system components. It should additionally be appreciated that certain embodiments the systems of FIGS. 10 to 15 can include at least one input device and/or at least one display device, and the one or more controller can be programmed or configured to operate with the at least at least one input device and/or at least one display device.

Figure 16:
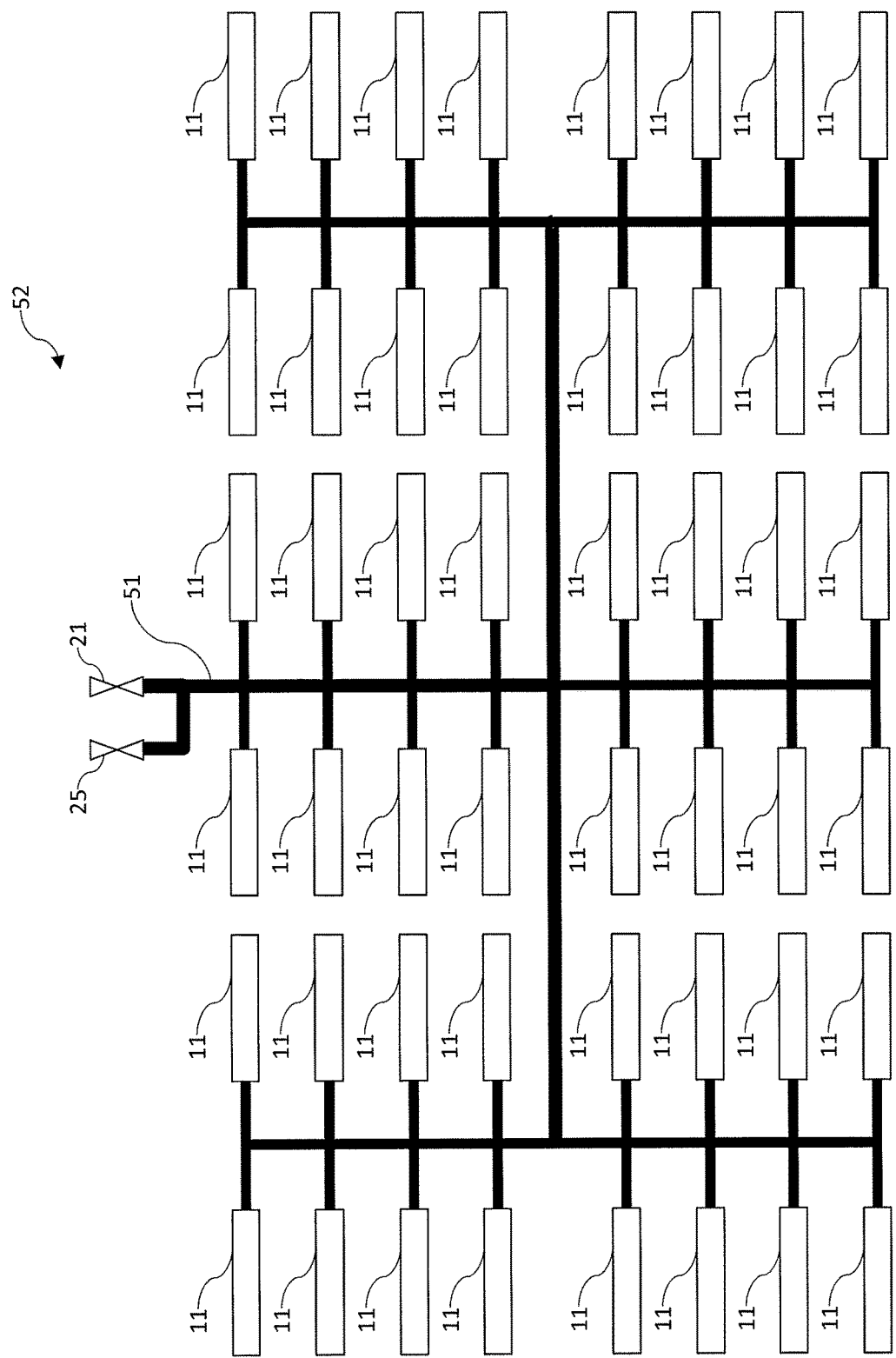
FIG. 16 is a schematic diagram illustrating an embodiment of a filtration system of the present disclosure in which multiple modules are connected or coupled fluidly in parallel within a cassette, and in which backwash, filtration and other systems operations can be performed through a single set of valves.

Referring now to FIG. 16, FIG. 16 is a schematic diagram illustrating an embodiment of a hollow fiber dead-end filtration system of the present disclosure in which multiple modules are connected or coupled fluidly in parallel within a cassette, and in which backwash, filtration and other systems operations can be performed through a single set of valves. The example illustrated in FIG. 16 includes a single cassette 52 having forty-eight modules 11. Modules 11 are structured and arranged to be held or positioned in at least one treatment tank (according to any of the one or more treatment tanks described herein), and thus cassette 52 is also positioned or held in the at least one treatment tank. Each of the forty-eight modules 11 is connected fluidly in parallel via a cassette header 51. The entire cassette 52 can perform filtration, backwash, and other system functions such as cleaning through a single set of permeate and backwash valves 25 and 21, respectively (e.g., only one permeate valve and only one backwash valve). That is, a backwash sequence and a dead-end filtration process can be performed via opening and closing permeate and backwash valves 25 and 21.

In one particular embodiment, the system of FIG. 16 includes at least one treatment tank and a cassette positioned in the treatment tank. The cassette includes a plurality of membrane filtration modules 11 coupled fluidly in parallel via a cassette header 51. In particular embodiment, the number of modules can be 48 or more. Each of the plurality of membrane filtration modules 11 includes hollow fiber membranes defining lumens, and the total outside surface area of all of the hollow fiber membranes of the cassette 52 in an embodiment can range from 500 m$^2$ to 2200 m$^2$. A single permeate valve 25 (e.g., only one permeate valve) is coupled fluidly to the cassette header, and a single backwash valve 21 (e.g., only one backwash valve) is likewise coupled fluidly to header. The system is configured to perform dead-end filtration of an algae slurry contained in the at least one treatment tank so that permeate is pulled through pores of the hollow fiber membranes and flows inside the lumens of the hollow fiber membranes and retentate is produced outside the lumens of the hollow fiber membranes. The system is also configured to perform a backwash sequence in which a backwash fluid (e.g., at least one of a fluid and a gas) flows inside the lumens of the hollow fiber membranes and is pushed through the pores of the hollow fiber membranes so as to remove any foulants that have accumulated on the hollow fiber membranes. In an embodiment, the single backwash valve for the backwash sequence can have an actuation time of three seconds or less, and the actuation time for the singe backwash valve can include the time to open or close the single backwash valve. In an embodiment, the single permeate valve for the backwash sequence can have an actuation time of three seconds or less, and the actuation time for the singe permeate valve can include the time to open or close the single permeate valve.

Figure 17:
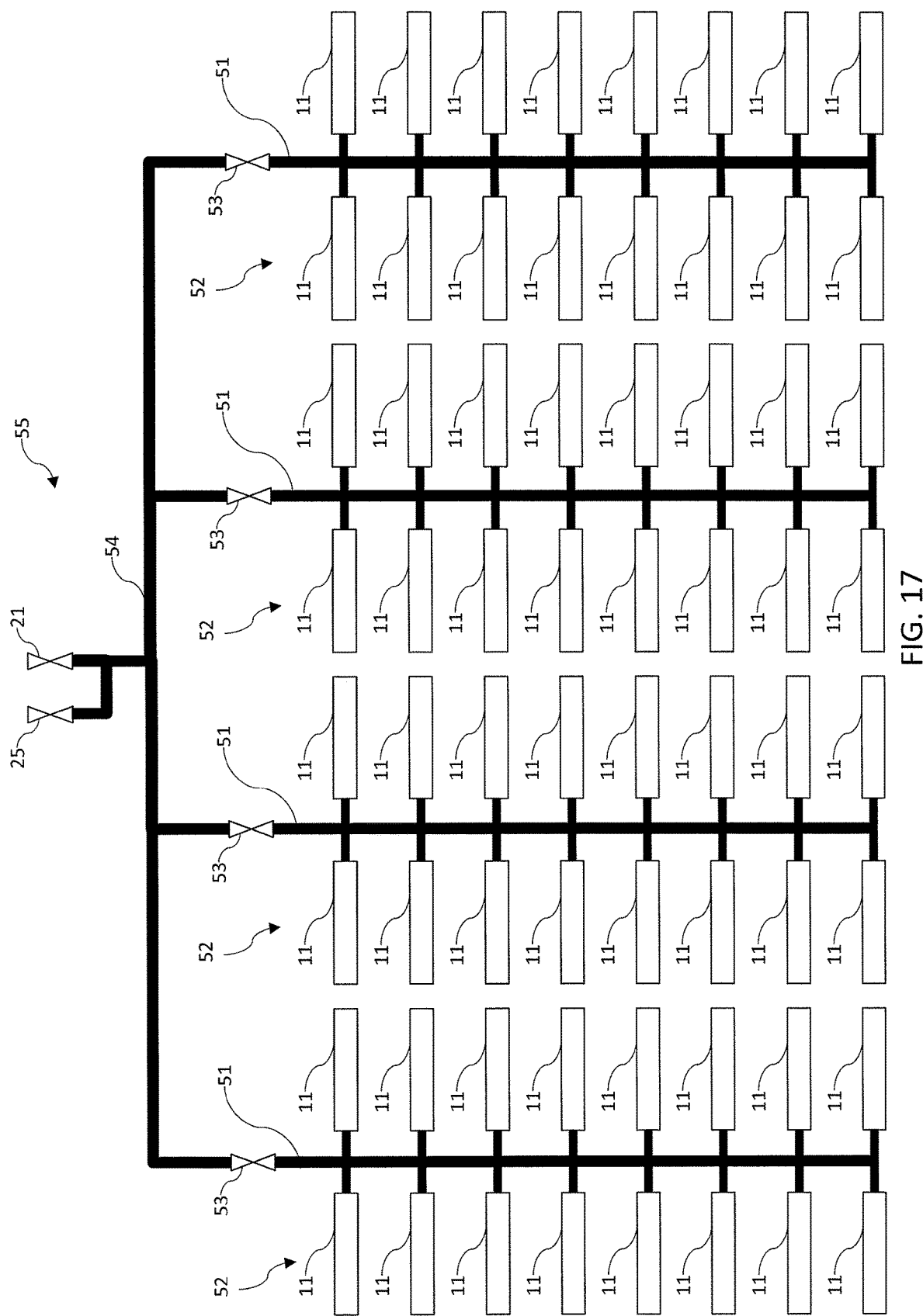
FIG. 17 is a schematic diagram illustrating an embodiment of a hollow fiber dead-end filtration system of the present disclosure in which multiple cassettes having modules are connected or coupled fluidly in parallel within a bank, and in which backwash, filtration and other system operations can be performed through a single set of valves.

Turning to FIG. 17, FIG. 17 is a schematic diagram illustrating an embodiment of a hollow fiber dead-end filtration system of the present disclosure in which multiple cassettes having modules are connected or coupled fluidly in parallel in a bank, and in which backwash, filtration and other system operations can be performed through a single set of valves. The example illustrated in FIG. 17 includes four cassettes 52, each of which has sixteen modules 11. Modules 11 are structured and arranged to be held or positioned in at least one treatment tank (as described herein), and thus each of cassettes 52 is also positioned or held in the at least one treatment tank. Each cassette 52 is connected or coupled fluidly in a single bank 55, which bank 55 is therefore also structured and arranged to be held in the at least one treatment tank. Each module 11 is connected or coupled fluidly in parallel via a cassette header 51. Each cassette 52 is connected fluidly in parallel via a bank header 54. The entire bank 55 can perform filtration, backwash, and other system functions such as cleaning through a single set of permeate and backwash valves 25 and 21, respectively. That is, a backwash sequence and dead-end filtration process can be performed via opening and closing backwash valves 25 and 21. Each of the cassettes 52 can be isolated from the permeate 25 and backwash 21 valves for maintenance, cleaning, or other operations by closing isolation valve 53.

In one particular embodiment, the system of FIG. 17 includes at least one treatment tank and a bank positioned inside the at least one treatment tank. The bank includes at least a first cassette and a second cassette. The first and second cassettes are coupled fluidly in parallel via a bank header. The first cassette includes a first plurality of membrane filtration modules coupled fluidly in parallel via a first cassette header. The second cassette includes a second plurality of membrane filtration modules coupled fluidly in parallel via a second cassette header. Each of the first and second plurality of plurality of membrane filtration modules include hollow fiber membranes defining lumens. The total outside surface area of all of the hollow fiber membranes of the bank in one embodiment can range from 500 $m^2$ to 10,000 $m^2$. The system further includes a single permeate valve (e.g., only one permeate valve) coupled fluidly to the bank header, and a single backwash valve (e.g., only one backwash valve) coupled fluidly to the bank header. The system is configured to (a) perform dead-end filtration of an algae slurry contained in the at least one treatment tank by pulling permeate through pores of the plurality hollow fiber membranes and flows inside the lumens of the hollow fiber membranes and retentate is produced outside the lumens of the hollow fiber membranes, and (b) perform a backwash sequence in which a backwash fluid (e.g., at least one of a fluid or a gas) flows inside the lumens of the hollow fiber membranes and is pushed through the pores of the plurality of hollow fiber membranes so as to remove any foulants that have accumulated on the hollow fiber membranes. In an embodiment, the single backwash valve for the backwash sequence can have an actuation time of three seconds or less, and the actuation time can include the time to open or close the single backwash valve. In an embodiment, the single permeate valve for the backwash sequence can have an actuation time of three seconds or less, and the actuation time can include the time to open or close the single permeate valve.

It should be appreciated that like the systems and methods of FIGS. 1 to 15, each of systems and methods illustrated by the embodiments of FIGS. 16 and 17 can also include one or more controller, which can be programmed or configured to operate with one or more of the system components so as to perform various functions of the system including cultivating, harvesting, valving, pumping, backwashing, rinsing, filtration, permeate flow, chemical cleaning, storing, flowing or any other system functions. In an embodiment, the one or more controller can include at least one processor and at least one memory device which stores instructions, which when executed by the at least one processor, cause the at least one processor to operate with any of the system components. It should additionally be appreciated that certain embodiments the systems of FIGS. 16 and 17 also can include at least one input device and/or at least one display device, and the one or more controller can be programmed or configured to operate with the at least at least one input device and/or at least one display device It should be appreciated from the foregoing that any suitable hollow fiber membranes, cassette and/or modules having such hollow fiber membranes can be utilized in any one or more of the filtration systems of the present disclosure. For example, commercially available and suitable cassettes and/or modules having hollow fiber membranes include ZeeWeed™ ultra filter technologies including ZW 500D modules and ZW 500 Cassettes. It should additionally be appreciated that in certain embodiments of the present disclosure, one or more concentration sensor can be included in any the systems described herein. For example, one or more concentration sensor can be included in one or more of tanks or stages (including the earthen lined tank), and one or more conduit so that the system can, for example, determine whether concentration of the in-feed, algae or biological slurry and/or the retentate has reached or attained a predetermined or specified level. Such predetermined level can be determined by sensing the concentration using one or more concentration sensor or by knowing the volumetric flow rate.

Various example embodiments, examples and/or simulations of the systems and methods of the present disclosure are discussed below.

Example 1

In one example of the present disclosure, it was demonstrated that high concentration solid slurries (e.g., 0.5% to 2%) can be attained using short backwash intervals (e.g., three minutes or less), and shorter backwash off-line periods, and with minimal energy input. For example, in one demonstration, a hollow-fiber dead-end membrane system was operated utilizing a reversing flow pump as illustrated in FIG. 2 so as to filter a 0.08% *Chlorella* sp. slurry from an open raceway algae cultivation system. The flow pump was fast acting, so the backwash off-line period was only one second longer than the backwash flow period. The system was initially operated under a ten second backwash off-line period and a 15 minute backwash interval. Under these conditions, it was observed that the permeate flux was reduced by 75% with at a volumetric concentration factor (VCF) of 6, i.e., increasing the algae concentration to 0.48%. A shorter backwash interval of eight minutes, with the same backwash off-line period to backwash interval ratio, i.e., a five second backwash off-line period, resulted in a permeate flux reduction of 65% at a VCF of 6. Maintaining an eight minute backwash interval, but increasing the backwash off-line period to 15 seconds resulted in a 20% reduction in permeate flux at a VCF of 6, which indicated that attaining concentrations of greater than 1% in biological slurries (e.g., algae slurries) requires increasing the backwash off-line period and decreasing the backwash interval. It was surprisingly discovered that a three minute backwash interval with a five second backwash off-line period resulted in a 7% reduction in permeate flux at a VCF of 6, and that reducing the backwash interval to one minute with a two second backwash off-line resulted in only a 5% reduction in permeate flow at VCF of 6. These results demonstrate that at backwash intervals above five minutes, longer backwash off-line periods are required to reach concentrations of up to 0.5% to 2% solids in biological slurries. It was therefore illustrated that at very short backwash intervals, such as three minutes or less, 0.5% to 2% solids slurries are attained using very short backwash off-line periods with only a small reduction in permeate flux. It was additionally demonstrated in this example system that minimal energy is required to attain such high concentration solids slurries. In one simulation, the dead end filtration system of the present disclosure required 0.04 kWh/m$^3$ to 0.16 kWh/m$^3$ of energy to obtain such high concentrations of solids algae, while a ceramic cross-flow filtration system utilizing the same algae and media required significantly more energy—4 to 7 kWh/m$^3$.

Example 2

In another example of the present disclosure, it was demonstrated, using permeability data, that a shorter backwash period (e.g., three seconds or less) with a very short backwash interval (e.g., one minute), results in a 15 fold increase in the final concentration of a solid slurry in a hollow-fiber dead-end membrane filtration system. In particular, a dead-end hollow fiber filtration system was operated with a reversing flow pump as illustrated in FIG. 2 to filter a 0.08% Chlorella sp. slurry to high concentration, e.g., greater than 3%, from an open raceway algae cultivation system. The pump was again fast acting, so the backwash off-line period was only one second longer than the backwash flow period. When the system was operated at eight minute backwash intervals with a 12 second backwash off-line period, the final VCF of 15 was achieved, i.e., the final retentate algae concentration was 1.2%, which was generally expected for non-flocculated biological slurries. When the system was operated with a one minute backwash interval and three second backwash off-line period, a final VCF of 225 was achieved, i.e., the final retentate algae concentration was 18%. It was therefore illustrated that using a short backwash interval, such as one minute, with a short backwash period, such as three seconds, resulted in a 15-fold improvement in the final concentration attained with a hollow fiber dead-end membrane system. It was additionally demonstrated in this example system that minimal energy is required to attain such high concentration solids slurries. In one simulation, the dead end filtration system required 0.04 to 0.16 kWh/m$^3$ of energy to obtain such high concentrations of solids algae, while a ceramic cross-flow filtration system utilizing the same algae and media required significantly more energy—4 to 7 kWh/m$^3$.

Example 3

In another example embodiment, it was demonstrated that there is a significant advantage to a variable flux, decreasing area multistage system over either a single stage system or an equal area, constant flux multistage system. As the concentration of algae slurries increases in a hollow fiber dead-end filtration system, the permeate flux decreases. And achieving a high concentration in a single stage system requires removal of a substantial portion of the permeate at high concentration. For algae harvesting, the algae is typically the product, so the retentate solids concentration is very important. A decreasing area, variable flux system operated according to the embodiment of FIG. 6, for example, results in a large improvement in the average flux for the system compared to typical multistage or to typical single stage systems.

Table 1 below provides a comparison of the average flux for different system configurations to concentrate algae slurries based upon a permeability concentration curve for Chlorella sp. with a one minute backwash interval and a three second backwash off-line period. In each case, the total membrane area is the same, but the configuration is different, i.e., all in one stage (single stage), equally divided among multiple stages (equal area multistage), and decreasing area in each successive stage (decreasing area multistage). Another difference in the configuration is the operational control, i.e., the same flux in each stage (i.e., the same or substantially the same constant flux), or variable flux in each stage, independent of the other stages (i.e., variable flux). For a very low concentration algae slurry, i.e., 0.02 g/l, concentrated to 10% suspended solids, the equal area and variable flux two-stage system has twice the throughput of a single stage system or an equal area, constant flux multistage system. Similarly, for a low concentration algae slurry, i.e., 0.02 g/l, concentrated to 10% suspended solids, the variable area and variable flux three-stage system has triple the throughput of a single stage system or an equal area, constant flux multistage system. A decreasing area, variable flux three-stage system provides a 15% throughput improvement over a decreasing area, variable flux two stage system.

For a higher concentration algae slurry feed and a higher concentration end point, i.e., 1 g/l to 18%, a decreasing area and variable flux to multistage system has a greater impact on throughput. A variable flux, decreasing area two-stage system has six times the throughput of a single stage system or equal area, constant flux multistage system. Additionally, a decreasing area, variable flux three-stage system has a 25% higher throughput than a decreasing area, variable flux two-stage system. These results illustrate a significant advantage of decreasing area, variable flux multistage systems over either single stage systems or equal area and constant flux multistage systems. The results also demonstrate that the optimal number of stages in certain embodiments is two or more depending upon the specific feed and retentate concentrations, as well as the flux versus concentration curve for the algae and cultivation conditions.

TABLE 1

| System Configuration (same total membrane area in each case) | Average flux to concentrate Chlorella sp. from 0.02 g/l to 100 g/l (l/m$^2$/h/bar) | Average flux to concentrate Chlorella sp. from 1 g/l to 180 g/l (l/m$^2$/h/bar) |
| --- | --- | --- |
| Single stage or Multistage equal area and constant flux | 94 | 30 |
| Two-stage, equal area and variable flux | 209 | 157 |
| Three-stage, equal area and variable flux | 240 | 194 |
| Two-stage, decreasing area and variable flux | 241 | 190 |
| Three-stage, decreasing area and variable flux | 277 | 242 |

Example 4

In yet another example embodiment of the present disclosure, a three-stage variable flux hollow fiber dead-end filtration system configured according to the embodiment of FIG. 7 was used to harvest and dewater an approximately 0.05% *Nannochloropsis* sp. slurry. In this simulation, a backwash off-line period of three seconds was used, and the backwash valve actuation time was approximately 0.25 seconds. The backwash flow started immediately since the gravity backwash system of FIG. 7 was used, so the backwash flow period was 2.5 seconds. Utilizing the system of FIG. 7 under these parameters, a final retentate concentration of 15% was achieved by using a backwash interval of one minute in the first two stages and thirty seconds in the third stage.

Example 5

In yet another example embodiment of the present disclosure, the advantage of using a purge valve to increase the acceptable flux range while increasing the throughput or reducing the energy consumption is illustrated. Table 2 below compares the flux range for three example hollow fiber dead-end filtration systems: (1) a system configured according to the embodiment of FIG. 5; (2) a system configured according to the embodiment of FIG. 5 with the purge valve 26 eliminated; and (3) a system configured according to the embodiment of FIG. 4. In the first system, the permeate conduit is sized for minimal pressure drop. In System 1 and System 2 there is no purge valve, so the permeate conduit is sized so that air is entrained in the liquid permeate flow and removed from the conduit. In the first two systems, the height between the liquid in treatment tank 10 and permeate level in permeate siphon tank 41 is such that a seven p.s.i. suction or pulling force is used on the membranes at no flow. In System 3, the system maintains 6 p.s.i. (±1 p.s.i.) pulling or suction force across the membranes, and the pressure at the pump is reduced to maintain this pressure as flow is increased. The suction pressure is lower in System 3 because some margin is needed to avoid over-pressurization as the controls adjust to changing flow; whereas in Systems 1 and 2, it is impossible to draw more suction than the change in elevation. Comparing the first two systems with systems using gravity suction and backwash, using a purge valve resulted in a 140% increase in maximum flux and a 50% reduction in energy use. Comparing System 1 with System 3, which has a more complicated pumped system with controls, using System 1 with the purge valve resulted in a 120% increase in maximum flux and a 20% reduction in energy use.

TABLE 2

| | Units | System 1 | System 2 | System 3 |
|---|---|---|---|---|
| Air removal | | Purge valve | Entrain in liquid | Entrain in liquid |
| Minimum flux | l/m²h | 24 | 24 | 24 |
| Maximum flux | l/m²h | 120 | 50 | 100 |
| Energy use | kWh/m³ | 0.04 | 0.08 | 0.05 |

Example 6

In another example, it was demonstrated that for relatively larger filtration plants, designing a hollow fiber membrane filtration system such that the modules of hollow fiber membranes are grouped for shorter backwash times offers significant advantages over designing groupings to minimize the number of valves. Assuming approximately 30 m² hollow-fiber surface area for each module of an algae harvesting system, a modest algae harvest and dewatering plant (e.g., 25 million gallons per day) will contain approximately 1000 modules, and a large algae harvest and dewatering plant (e.g., 700 million gallons per day) will contain approximately 28,000 modules. It is clear that the modules in this example should be grouped so that automatic valves are not required for each module.

Table 3 below illustrates the cost per module as function of grouping for a 250 million gallon per day algae harvest and dewatering plant containing 10,000 modules. The installed cost of small automatic valves used for individual modules (including the cost of the valve, the cost of wiring and plumbing air to the valve and the cost of controls for the valve) is assumed to be between the installed cost of a module and twice the installed cost of a module. The larger valves used for groups of modules are assumed to be 50% more expensive than the smaller valves used for single modules. The first column illustrates the approach of using a set of valves for each module. The second column illustrates the approach of grouping a system into 20 racks of 500 modules each to minimize the number of automatic valves. In the second case, the valve actuation time is 15 seconds. The third column illustrates an approach according to one embodiment of the present disclosure in which the modules are grouped into 200 cassettes of 50 modules each, such that the valve actuating time is three seconds (rather than minimizing the number of valves). It should be appreciated that Table 3 illustrates that minimizing the number of valves minimizes the cost of the filtration plant for a fixed number of modules.

However, the cost per quantity of permeate removed is more relevant than the cost of the filtration plant for a fixed number of modules. Table 4 examines the cost of per quantity of permeate removed in terms of net filtration time per cycle per module divided by the module cost including valves from Table 3. In Table 4, the full backwash flow rate is assumed to be twice the permeate flow rate during filtration, and the average backwash flow rate during the time the valves are opening and closing is assumed to be half of the full backwash flow rate. The time at full backwash flow is assumed to be three seconds. The backwash recovery time is the time to re-filter the permeate that was pushed back into the retentate during the backwash. Backwash intervals of four minutes and two minutes are considered for each of the three grouping options. In all cases, grouping modules is less costly than using a single set of valves for each module, and grouping modules so that the maximum valve actuation time is three seconds is less costly than grouping the modules to minimize the number of valves. For the shorter backwash time, flow per module cost is 87% higher for grouping so that the maximum actuation time (e.g., the time to open or close valves) is three seconds or less compared to grouping modules to minimize the number of valves. For the longer backwash time, the flow per module cost is 22% higher for grouping so that the maximum actuation time is three seconds or less. It should therefore be appreciated from the foregoing that in relatively large filtration plants, a hollow fiber membrane filtration system designed such that modules are grouped so that there is a short valve actuation time offers significant savings over designs in which modules are grouped to minimize the number of valves.

TABLE 3

|  | Case 1: No module grouping | Case 2: Minimize number of valves | Case 3: Valve actuation time of 3-seconds |
|---|---|---|---|
| No. of modules | 10,000 | 10,000 | 10,000 |
| No. of cassettes or racks | None | 20 | 200 |
| No. of automatic valves | 20,000 | 40 | 400 |
| Single valve cost relative to a module cost | 100-200% | 150-300% | 150-300% |
| Valve cost per module | 200 to 400% | 0.6-1.2% | 4.0-8.0% |
| Module cost including valves relative to a single module cost | 300% to 500% | 100.6% to 101.2% | 106% to 112% |

TABLE 4

| | Backwash interval | | | | | |
|---|---|---|---|---|---|---|
| | 2-minutes | | | 4-mintues | | |
| | Backwash full flow | | | | | |
| | 5-seconds | | | 15-seconds | | |
| Case | 1 | 2 | 3 | 1 | 2 | 3 |
| Valve actuation time (sec) | 0.25 | 15 | 3 | 0.25 | 15 | 3 |
| Backwash full flow (sec) | 5 | 5 | 5 | 15 | 15 | 15 |
| Backwash off-line time (sec) | 5.5 | 35 | 11 | 15.5 | 45 | 21 |
| Backwash recovery time (sec) | 10.5 | 40 | 16 | 30.5 | 60 | 36 |
| Net Filtration time per cycle (sec) | 104 | 45 | 93 | 194 | 135 | 183 |
| Module cost including valves | 500% | 101.2% | 112% | 500% | 101.2% | 112% |
| Net filtration time per cycle/module cost per cycle | 21 | 44 | 83 | 39 | 133 | 163 |

Example 7

In another example embodiment of the present disclosure, a two-stage cultivation and harvesting process, such as the systems and methods described in FIGS. 14 and 15, was used to grow *Nitszchia* sp. to a produce an algal lipid oil product. The algae were cultivated under nutrient replete conditions during the first stage of cultivation to attain high biomass productivity. In the second stage of the cultivation, lipid oil accumulation was induced by limiting the silica and nitrogen in the media. First, this process was implemented by growing the algae in nutrient replete conditions, and then stopping the addition of nitrogen and silica in the fertilizer. After the addition of nitrogen and silica was stopped, the algae continued to grow in exponential phase for a day, and then the algae accumulated lipid oil, reaching 24% oil after 5 days of nutrient limitation. Then, this process was repeated using the system and methods illustrated in FIGS. 10 and 11 and utilizing the algae harvesting and dewatering system illustrated in the embodiment of FIG. 6 to concentrate and rinse the algae media. The algae were then cultivated in media (i.e., a second different media) with no nitrogen or silica fertilizer. In this case, the algae accumulated 36% oil in 3 days of nutrient limitation. Using the two-stage cultivation process with a hollow fiber dead-end harvest and rinse step between the stages as discussed in the system and methods of FIGS. 10 and 11, caused 50% increase in the lipid oil product and a 40% decrease in the accumulation time.

Example 8

Another example embodiment of the present disclosure is the use of a multi-stage cultivation and harvesting method and system (e.g., the systems and methods of FIGS. 13 and 14) along with a chemical trigger of caffeine. Caffeine has been used as a trigger to induce a response in genetically engineered algae. The concentration of caffeine required to induce the response is 100 mg/l. In a typical two-stage algae production process, the algae is grown without caffeine in the first stage and then caffeine is added in the second stage. If the algae are grown at 1 g/liter, then caffeine equivalent to 10% of the weight of the algae must be added in the second stage, which is prohibitively expensive. Furthermore, unless all of the caffeine is consumed or degraded during the second stage, then once the algae is harvested from the second stage, the recycled media must be treated to remove the caffeine prior to re-use the first stage.

Adding a hollow fiber dead-end filtration step after the first stage of the process, as illustrated in FIGS. 13 and 14, can remove all of the media so that permeate can be recycled to the first stage without treatment to remove the caffeine. Additionally, concentrating the algae to 10% in the hollow fiber dead-end filtration system and adding the caffeine to the concentrate prior to re-cultivation, can reduce the amount of caffeine required by 100-fold. Also, the media from the second stage cultivation can be recycled, so no treatment is needed to remove caffeine that remains in the second stage media.

Example 9

In yet another example embodiment, the diatom *Thalassiosira weissflogii* was cultivated for use in a shrimp larval feed. In one particular example, the diatom was cultivated to approximately 0.5 g/l and the algae slurry was added to a vessel containing shrimp larva. In a second example case, the diatom was cultivated to approximately 0.5 g/l and the algae slurry was harvested and dewatered to a 5% slurry of live diatoms in a hollow fiber dead-end filtration system configured as illustrated in FIG. 6. In the second case, the 5% live diatom slurry was stored at 4° C. for two weeks and then diluted to 0.5 g/l and added to a vessel containing shrimp larva. The viability and health of the shrimp larva was similar for both the larva that were fed freshly grown algae as well as the larva that were fed algae that had been concentrated in a hollow fiber dead-end filtration system, stored for two weeks, and then reconstituted into dilute slurry.

Example 10

In still another example, it was demonstrated that a hollow-fiber dead end filtration system that utilizes a rinse step can reduce the dissolved solids by orders of magnitude. In one simulation, *Chlorella* sp. was cultivated at 0.7 g/l in a bicarbonate/carbonate media at a pH of 9.5 and the algae were harvested using a centrifuge to attain a 15% slurry. The algae needs to be processed at a pH of less than 7, which would require the addition of 125 g of sulfuric acid per kilogram of algae to neutralize the dissolved bicarbonate/carbonate in the slurry prior to the extraction process. In a second example simulation, *Chlorella* sp. was cultivated at 0.7 g/l in a bicarbonate/carbonate media at a pH of 9.5 and was harvested in a hollow fiber dead-end filtration system configured as illustrated in FIG. 6. In this case, after an algae concentration of 15% was attained, the feed was stopped, and water was added to displace the sodium bicarbonate and sodium carbonate ions while maintaining the algae concentration at 15%. The algae needs to be processed at a pH of less than 7, which requires only 1 g of sulfuric acid per kilogram of algae. It should therefore be appreciated that utilizing a hollow fiber dead-end filtration system according to FIG. 6 and having a rinse step reduced the dissolved solids by two orders of magnitude.

Example 11

In yet another example, it was demonstrated that a lower cost lined earthen pond can be used as a treatment tank in a multistage hollow fiber membrane filtration system, for example, as described in FIG. 6. In a single stage filtration system, attaining a high algae concentration in a short amount of time typically requires maximizing the packing density of the hollow fiber membranes. Using permeability curves measured for *Chlorella* sp. generated in a system with a packing density of 15 ft$^2$ of membrane area per gallon, it was demonstrated that the residence time to achieve a 15% algae slurry from a 0.05% concentration feed in a single stage system increases by 33 hours if the packing density is reduced to 7.5 ft$^2$ of membrane area per gallon, which illustrates why membrane filtration systems use concrete, metal, and/or plastic tanks so that a tight tolerance can be maintained between the walls and the hollow-fiber modules.

On the other hand, the hydraulic residence time can be much lower in multistage hollow fiber membrane filtration systems, such as the system illustrated in FIG. 6 because of the higher average flux in the first few stages, and the effect of reducing packing density is much less pronounced. For example, if the packing density is reduced from 15 ft$^2$ to 7.5 ft$^2$ of membrane area per gallon in the first two stages of a three stage system, then the residence time to achieve a 15% slurry from 0.05% concentration feed increases by 12 minutes. It should therefore be appreciated that in one example, a lower cost earthen lined pond can be used as the containment or treatment tank for one or more of the first few stages of a multistage system, or for the first stage only in a multistage system, thereby substantially decreasing the packing density without having a major impact on the algae residence time in the system.

What is claimed is:

1. An algae harvesting method comprising:
   in a dead end filtration process operating at or below atmospheric pressure, pulling a substantially algae-free permeate from an algae slurry through pores of a plurality of hollow fiber membranes positioned inside at least one treatment tank so that the permeate flows inside lumens of the plurality of hollow fiber membranes and a retentate of the algae slurry is produced outside the lumens of the plurality of hollow fiber membranes; and
   in a backwash sequence, pushing a backwash fluid through pores of the plurality of hollow fiber membranes to remove any foulants that have accumulated on the plurality of hollow fiber membranes,
   wherein the method includes (i) an interval of less than about three minutes, the interval defined as the time between the start of one backwash cycle and the start of a next backwash cycle and (ii) an off-line period of less than about twelve seconds, the off-line period defined as the time between an end of the dead end filtration process and a start of a next dead end filtration process.

2. The algae harvesting method of claim 1, wherein (i) the algae slurry is a non-flocculated algae slurry having a first concentration of suspended solid algae, and (ii) the retentate has a second concentration of suspended solid algae that is greater than the first concentration, the second concentration equal to at least three percent solids content.

3. The algae harvesting method of claim 1, wherein (i) the algae slurry is a non-flocculated algae slurry having a first concentration of suspended solid algae, and (ii) the retentate has a second concentration of suspended solid algae that is about fifty times greater than the first concentration.

4. The algae harvesting method of claim 1, wherein at least about seventy-five percent of the suspended algae in the retentate is alive.

5. The algae harvesting method of claim 1, wherein said pulling during the dead-end filtration process includes siphoning.

6. The algae harvesting method of claim 5, wherein said pushing during the backwash sequence includes pushing gas accumulated in a siphon conduit through a purge conduit coupled fluidly to the siphon conduit.

7. The algae harvesting method of claim 1, where said pushing during the backwash sequence includes gravity feeding the backwash fluid.

8. The algae harvesting method of claim 1, wherein the backwash fluid includes at least one of a liquid and a gas.

9. The algae harvesting method of claim 1, wherein the plurality of hollow fiber membranes are positioned in at least one treatment tank, and the at least one treatment tank includes (a) a plurality of treatment tanks in which each of the treatment tanks defines one stage of a plurality of filtration stages and contains at least one of the plurality of membrane filtration modules, or (b) at least one divider separating the at least one treatment tank into a plurality of filtration stages, each of the plurality of filtration stages containing at least one of a plurality of membrane filtration modules.

10. An algae harvesting method comprising:
    isolating, using a first valve, a permeate suction source from a permeate outlet, the permeate outlet in fluid communication with an inside of lumens of a plurality of hollow fiber membranes positioned inside at least one treatment tank,
    isolating, using a second valve, a backwash supply source from the permeate outlet, the backwash supply source configured to maintain a positive backwash pressure when the second valve is closed,
    in a dead end filtration process operating at or below atmospheric pressure, pulling a substantially algae-free permeate from an algae slurry through pores of a plurality of hollow fiber membranes positioned inside at least one treatment tank so that the permeate flows inside lumens of the plurality of hollow fiber membranes and a retentate of the algae slurry is produced outside the lumens of the plurality of hollow fiber membranes; and
    in a backwash sequence:
       closing the first valve,
       opening the second valve and immediately applying a backwash pressure to the permeate outlet and the lumens, and pushing a backwash fluid through pores of the plurality of hollow fiber membranes to remove any foulants that have accumulated on the plurality of hollow fiber membranes, wherein the method includes (i) an interval of less than about three minutes, the interval defined as the time between the start of one backwash cycle and the start of a next backwash cycle and (ii) an off-line period of less than about twelve seconds, the off-line period defined as the time between an end of the dead end filtration process and a start of a next dead end filtration process.

11. The algae harvesting method of claim 10, wherein the permeate suction source is configured to maintain a permeate suction pressure when the first valve is closed, the method further comprising, at an end of the backwash sequence:
closing the second valve, and
opening the first valve and immediately applying a negative suction pressure to the permeate outlet and the lumens.

12. The algae harvesting method of claim 10, wherein (i) the algae slurry is a non-flocculated algae slurry having a first concentration of suspended solid algae, and (ii) the retentate has a second concentration of suspended solid algae that is greater than the first concentration, the second concentration equal to at least three percent.

13. The algae harvesting method of claim 10, wherein (i) the algae slurry is a non-flocculated algae slurry having a first concentration of suspended solid algae, and (ii) the retentate has a second concentration of suspended solid algae that is about fifty times greater than the first concentration.

14. The algae harvesting method of claim 10, wherein at least about seventy-five percent of the suspended algae in the retentate is alive.

15. The algae harvesting method of claim 10, wherein the backwash supply source includes a siphon.

16. The algae harvesting method of claim 15, wherein said pushing during the backwash sequence includes pushing gas accumulated in a siphon conduit through a purge conduit coupled fluidly to the siphon conduit.

17. The algae harvesting method of claim 10, where said pushing during the backwash sequence includes gravity feeding the backwash fluid.

18. The algae harvesting method of claim 10, wherein the backwash fluid includes at least one of a liquid and a gas.

19. The algae harvesting method of claim 10, wherein the plurality of hollow fiber membranes are positioned in at least one treatment tank, and the at least one treatment tank includes (a) a plurality of treatment tanks in which each of the treatment tanks defines one stage of a plurality of filtration stages and contains at least one of the plurality of membrane filtration modules, or (b) at least one divider separating the at least one treatment tank into a plurality of filtration stages, each of the plurality of filtration stages containing at least one of a plurality of membrane filtration modules.

20. The algae harvesting method of claim 10, wherein the backwash supply source comprises a pump.

21. The algae harvesting method of claim 10, wherein the permeate suction source comprises a pump.

22. The algae harvesting method of claim 10, wherein the permeate suction source comprises an elevated tank, the elevated tank being elevated relative to the at least one treatment tank.

* * * * *